US010449236B2

(12) United States Patent
Marozsan et al.

(10) Patent No.: US 10,449,236 B2
(45) Date of Patent: Oct. 22, 2019

(54) TREATING SEIZURE WITH RECOMBINANT ALKALINE PHOSPHATASE

(71) Applicant: Alexion Pharmaceuticals, Inc., New Haven, CT (US)

(72) Inventors: Andre Marozsan, New Haven, CT (US); Denise Devore, New Haven, CT (US); Susan Liu-Chen, New Haven, CT (US)

(73) Assignee: Alexion Pharmaceuticals, Inc., Boston, MA (US)

(*) Notice: Subject to any disclaimer, the term of this patent is extended or adjusted under 35 U.S.C. 154(b) by 204 days.

(21) Appl. No.: 15/532,203

(22) PCT Filed: Dec. 4, 2015

(86) PCT No.: PCT/US2015/064003
§ 371 (c)(1),
(2) Date: Jun. 1, 2017

(87) PCT Pub. No.: WO2016/090251
PCT Pub. Date: Jun. 9, 2016

(65) Prior Publication Data
US 2017/0360899 A1 Dec. 21, 2017

Related U.S. Application Data

(60) Provisional application No. 62/259,307, filed on Nov. 24, 2015, provisional application No. 62/088,025, filed on Dec. 5, 2014.

(51) Int. Cl.
A61K 38/46 (2006.01)
A61K 45/06 (2006.01)

(52) U.S. Cl.
CPC ........... A61K 38/465 (2013.01); A61K 45/06 (2013.01); C12Y 301/03001 (2013.01)

(58) Field of Classification Search
CPC combination set(s) only.
See application file for complete search history.

(56) References Cited

U.S. PATENT DOCUMENTS

| 5,336,759 A | 8/1994 | Matsuo et al. |
| 5,338,830 A | 8/1994 | Matsuo et al. |
| 5,340,920 A | 8/1994 | Matsuo et al. |
| 5,352,770 A | 10/1994 | Matsuo |
| 5,428,130 A | 6/1995 | Capon et al. |
| 5,434,133 A | 7/1995 | Tanaka et al. |
| 5,583,108 A | 12/1996 | Wei et al. |
| 5,665,704 A | 9/1997 | Lowe et al. |
| 5,714,147 A | 2/1998 | Capon et al. |
| 5,767,239 A | 6/1998 | Immer et al. |
| 5,846,932 A | 12/1998 | Lowe et al. |
| 5,948,761 A | 9/1999 | Seilhamer et al. |
| 5,973,134 A | 10/1999 | Matsuo et al. |
| 6,020,168 A | 2/2000 | Matsuo et al. |
| 6,028,055 A | 2/2000 | Lowe et al. |
| 6,034,231 A | 3/2000 | Tanaka et al. |
| 6,290,952 B1 | 9/2001 | Poelstra et al. |
| 6,406,697 B1 | 6/2002 | Capon et al. |
| 6,407,211 B1 | 6/2002 | Burnett, Jr. et al. |
| 6,420,384 B2 | 7/2002 | Weigele et al. |
| 6,436,386 B1 | 8/2002 | Roberts et al. |
| 6,455,495 B1 | 9/2002 | Orgel et al. |
| 6,458,579 B2 | 10/2002 | Hopwood et al. |
| 6,525,022 B1 | 2/2003 | Lowe et al. |
| 6,541,610 B1 | 4/2003 | Smith |
| 6,743,425 B2 | 6/2004 | Nakao |
| 6,790,649 B1 | 9/2004 | Crine et al. |
| 6,818,619 B2 | 11/2004 | Burnett, Jr. et al. |
| 6,830,885 B1 | 12/2004 | Lanctot et al. |
| 6,849,714 B1 | 2/2005 | Bridon et al. |
| 6,887,470 B1 | 5/2005 | Bridon et al. |
| 6,905,689 B2 | 6/2005 | Schneidinger et al. |
| 6,946,484 B2 | 9/2005 | Adams et al. |
| 7,026,293 B2 | 4/2006 | Kitakaze |
| 7,033,997 B2 | 4/2006 | Forssmann et al. |
| 7,070,974 B1 | 7/2006 | Desgroseillers et al. |
| 7,105,539 B2 | 9/2006 | Gravel et al. |
| 7,179,903 B2 | 2/2007 | McArthur et al. |
| 7,256,253 B2 | 8/2007 | Bridon et al. |
| 7,271,149 B2 | 9/2007 | Glaesner et al. |
| 7,276,481 B2 | 10/2007 | Golembo et al. |
| 7,341,838 B2 | 3/2008 | Buechler et al. |
| 7,365,091 B2 | 4/2008 | Gravel et al. |
| 7,384,917 B2 | 6/2008 | Burnett, Jr. et al. |

(Continued)

FOREIGN PATENT DOCUMENTS

| EP | 0478797 B1 | 4/1995 |
| EP | 0769554 A2 | 4/1997 |

(Continued)

OTHER PUBLICATIONS

De Roo et al., "Infantile hypophosphatasia without bone deformities presenting with severe pyridoxine-resistant seizures," Molecular Genetics and Metabolism 111(3):404-7 (2014).

Hofmann et al., "Clinical aspects of hypophosphatasia: an update," Clinic Rev Bone Miner Metab. 11(2):60-70 (2013).

Hofmann et al., "Compound heterozygosity of two functional null mutations in the ALPL gene associated with deleterious neurological outcome in an infant with hypophosphatasia," Bone. 55:150-7 (2013).

Matsumoto et al., "Rescue of severe infantile hypophosphatasia mice by AAV-mediated sustained expression of soluble alkaline phosphatase," Hum Gene Ther. 22(11):1355-64 (2011).

Millán et al., "Enzyme replacement therapy for murine hypophosphatasia," J Bone Miner Res. 23(6): 777-87 (2008).

(Continued)

Primary Examiner — Kagnew H Gebreyesus
(74) Attorney, Agent, or Firm — Clark & Elbing LLP

(57) ABSTRACT

The present disclosure provides a method of treating seizure in a subject having aberrant alkaline phosphatase activities, comprising administering a therapeutically effective amount of at least one recombinant alkaline phosphatase to the subject.

20 Claims, 14 Drawing Sheets
Specification includes a Sequence Listing.

(56) References Cited

U.S. PATENT DOCUMENTS

| | | |
|---|---|---|
| 7,399,466 B2 | 7/2008 | Boileau |
| 7,414,107 B2 | 8/2008 | Larsen |
| 7,425,531 B2 | 9/2008 | Lanctot et al. |
| 7,427,498 B2 | 9/2008 | Crine et al. |
| 7,470,668 B2 | 12/2008 | Lanctot et al. |
| 7,488,713 B2 | 2/2009 | Vesely |
| 7,527,939 B2 | 5/2009 | Davey et al. |
| 7,563,769 B2 | 7/2009 | Bogin et al. |
| 7,625,564 B2 | 12/2009 | Wang et al. |
| 7,642,243 B2 | 1/2010 | Nakao et al. |
| 7,648,962 B2 | 1/2010 | James et al. |
| 7,662,773 B2 | 2/2010 | James et al. |
| 7,678,391 B2 | 3/2010 | Graham et al. |
| 7,732,406 B2 | 6/2010 | Mitrovic et al. |
| 7,736,653 B2 | 6/2010 | Kim et al. |
| 7,754,852 B2 | 7/2010 | Burnett, Jr. et al. |
| 7,763,712 B2 | 7/2010 | Crine et al. |
| 7,803,769 B2 | 9/2010 | Sullivan et al. |
| 7,803,901 B2 | 9/2010 | Burnett, Jr. et al. |
| 7,825,092 B2 | 11/2010 | Vesely |
| 7,846,900 B2 | 12/2010 | Vesely |
| 7,858,560 B2 | 12/2010 | Koster et al. |
| 7,919,591 B2 | 4/2011 | Sheffer et al. |
| 7,943,126 B2 | 5/2011 | Tomatsu et al. |
| 7,960,529 B2 | 6/2011 | Crine et al. |
| 8,058,242 B2 | 11/2011 | Alewood et al. |
| 8,691,208 B2 | 4/2014 | Tomatsu et al. |
| 9,266,939 B2 | 2/2016 | Crine et al. |
| 9,988,620 B2 | 6/2018 | Crine et al. |
| 10,000,532 B2 | 6/2018 | Crine et al. |
| 2002/0183276 A1 | 12/2002 | Millan et al. |
| 2003/0158132 A1 | 8/2003 | Kovesdi |
| 2004/0023916 A1 | 2/2004 | Millan et al. |
| 2004/0077537 A1 | 4/2004 | Schreiner |
| 2004/0234518 A1 | 11/2004 | Crine et al. |
| 2005/0113286 A1 | 5/2005 | Schreiner et al. |
| 2005/0142217 A1 | 6/2005 | Adams et al. |
| 2005/0202442 A1 | 9/2005 | Morris et al. |
| 2005/0244904 A1 | 11/2005 | Ng |
| 2005/0276796 A1 | 12/2005 | Tomatsu et al. |
| 2006/0014687 A1 | 1/2006 | Crine et al. |
| 2006/0019890 A1 | 1/2006 | Kapoun et al. |
| 2006/0074009 A1 | 4/2006 | James et al. |
| 2006/0110359 A1 | 5/2006 | Sanchez-Ramos et al. |
| 2006/0172929 A1 | 8/2006 | Rappold-Hoerbrand et al. |
| 2006/0228710 A1 | 10/2006 | Morris et al. |
| 2007/0041972 A1 | 2/2007 | Rother et al. |
| 2007/0042957 A1 | 2/2007 | Burnett et al. |
| 2007/0081984 A1 | 4/2007 | Tomatsu et al. |
| 2007/0081986 A1 | 4/2007 | Tomatsu et al. |
| 2007/0197434 A1 | 8/2007 | Nakao et al. |
| 2007/0281887 A1 | 12/2007 | Pan |
| 2007/0292966 A1 | 12/2007 | Prickett et al. |
| 2007/0293418 A1 | 12/2007 | Larsen |
| 2008/0032933 A1 | 2/2008 | Burnett et al. |
| 2008/0081768 A1 | 4/2008 | Watt et al. |
| 2008/0085862 A1 | 4/2008 | Kim et al. |
| 2008/0113411 A1 | 5/2008 | Sheffer et al. |
| 2008/0113412 A1 | 5/2008 | Sheffer et al. |
| 2008/0125574 A1 | 5/2008 | Sheffer et al. |
| 2008/0153747 A1 | 6/2008 | Alewood et al. |
| 2008/0161243 A1 | 7/2008 | Rosen et al. |
| 2008/0181903 A1 | 7/2008 | Bhaskar et al. |
| 2008/0182299 A1 | 7/2008 | Colocaru et al. |
| 2008/0194481 A1 | 8/2008 | Rosen et al. |
| 2008/0194682 A1 | 8/2008 | Golembo et al. |
| 2008/0227713 A1 | 9/2008 | Protter |
| 2008/0293632 A1 | 11/2008 | Rappold-Hoerbrand et al. |
| 2008/0312142 A1 | 12/2008 | Nakao et al. |
| 2009/0011997 A1 | 1/2009 | Peri et al. |
| 2009/0053192 A1 | 2/2009 | Millan et al. |
| 2009/0069243 A1 | 3/2009 | Burnett, Jr. et al. |
| 2009/0092582 A1 | 4/2009 | Bogin et al. |
| 2009/0142347 A1 | 6/2009 | Millan |
| 2009/0170756 A1 | 7/2009 | Burnett, Jr. et al. |
| 2009/0221803 A1 | 9/2009 | Dall'Acqua et al. |
| 2009/0238814 A1 | 9/2009 | Tomatsu et al. |
| 2009/0240031 A1 | 9/2009 | Immer et al. |
| 2009/0247462 A1 | 10/2009 | Bogin et al. |
| 2009/0252729 A1 | 10/2009 | Farrington et al. |
| 2009/0258018 A1 | 10/2009 | Medich et al. |
| 2009/0275506 A1 | 11/2009 | Bakis et al. |
| 2009/0325195 A1 | 12/2009 | Davey et al. |
| 2010/0008979 A1 | 1/2010 | Tomatsu et al. |
| 2010/0055150 A1 | 3/2010 | Golembo et al. |
| 2010/0093678 A1 | 4/2010 | Della-Fera et al. |
| 2010/0160212 A1 | 6/2010 | Sheffer et al. |
| 2010/0168443 A1 | 7/2010 | Geysen |
| 2010/0184680 A1 | 7/2010 | Bevec |
| 2010/0197574 A1 | 8/2010 | Chen et al. |
| 2010/0204094 A1 | 8/2010 | Simari et al. |
| 2010/0204109 A1 | 8/2010 | Bevec |
| 2010/0204446 A1 | 8/2010 | Forssmann |
| 2010/0209958 A1 | 8/2010 | Nakao et al. |
| 2010/0216714 A1 | 8/2010 | James et al. |
| 2010/0221234 A1 | 9/2010 | Crine et al. |
| 2010/0240125 A1 | 9/2010 | Crine et al. |
| 2010/0249017 A1 | 9/2010 | Bevec et al. |
| 2010/0260706 A1 | 10/2010 | Bogin et al. |
| 2010/0261248 A1 | 10/2010 | Kim et al. |
| 2010/0297021 A1 | 11/2010 | Wendt et al. |
| 2010/0297119 A1 | 11/2010 | Crine et al. |
| 2010/0305031 A1 | 12/2010 | Wakabayashi et al. |
| 2010/0305051 A1 | 12/2010 | Burnett, Jr. et al. |
| 2010/0310561 A1 | 12/2010 | Canada et al. |
| 2010/0311660 A1 | 12/2010 | Simari et al. |
| 2010/0317600 A1 | 12/2010 | Immer et al. |
| 2010/0331256 A1 | 12/2010 | Wendt et al. |
| 2011/0152194 A1 | 6/2011 | Burnett, Jr. et al. |
| 2011/0250187 A1 | 10/2011 | Tomatsu et al. |
| 2011/0269684 A1 | 11/2011 | Burnett, Jr. et al. |
| 2011/0300143 A1 | 12/2011 | Sly et al. |
| 2012/0088771 A1 | 4/2012 | Millan |
| 2012/0164142 A1 | 6/2012 | Crine et al. |
| 2013/0108635 A1 | 5/2013 | Crine et al. |
| 2013/0323244 A1 | 12/2013 | Crine et al. |
| 2014/0193388 A1 | 7/2014 | Velders et al. |
| 2014/0194484 A1 | 7/2014 | Coats et al. |
| 2015/0353633 A1 | 12/2015 | Kakkis et al. |
| 2016/0052968 A1 | 2/2016 | Crine et al. |
| 2017/0175094 A1 | 6/2017 | Hatch |
| 2017/0360899 A1 | 12/2017 | Marozsan et al. |
| 2018/0230445 A1 | 8/2018 | Jaluria et al. |

FOREIGN PATENT DOCUMENTS

| | | |
|---|---|---|
| EP | 0771875 B1 | 5/1997 |
| EP | 0466174 B1 | 6/1997 |
| EP | 0475394 B1 | 6/1997 |
| EP | 0466175 B1 | 1/1998 |
| EP | 0477971 B1 | 1/1998 |
| EP | 0475290 B1 | 12/1998 |
| EP | 0475291 B1 | 12/1998 |
| EP | 0497368 B1 | 6/2002 |
| EP | 1492567 | 9/2003 |
| EP | 1502604 A1 | 2/2005 |
| EP | 1623994 A2 | 2/2006 |
| EP | 1759001 B1 | 3/2007 |
| EP | 1759710 A1 | 3/2007 |
| EP | 2158319 | 3/2010 |
| EP | 2158319 B1 | 12/2011 |
| JP | H0870875 A | 3/1996 |
| JP | 2000-327583 A | 11/2000 |
| JP | 2002-541776 A | 12/2002 |
| JP | 2007-511209 A | 5/2007 |
| JP | 2010-501026 A | 1/2010 |
| JP | 2010-526543 A | 8/2010 |
| JP | 2010-530222 A | 9/2010 |
| JP | 2011-504506 A | 2/2011 |
| WO | WO-92/20371 A1 | 11/1992 |
| WO | WO-94/20534 A1 | 9/1994 |
| WO | WO-95/05456 A1 | 2/1995 |
| WO | WO-95/13296 A1 | 5/1995 |
| WO | WO-95/33769 A1 | 12/1995 |

(56) References Cited

FOREIGN PATENT DOCUMENTS

| | | |
|---|---|---|
| WO | WO-98/17690 A1 | 4/1998 |
| WO | WO-98/35703 A2 | 8/1998 |
| WO | WO-99/46283 A1 | 9/1999 |
| WO | WO-00/18954 A2 | 4/2000 |
| WO | WO-00/50580 A2 | 8/2000 |
| WO | WO-00/53755 A2 | 9/2000 |
| WO | WO-00/64486 A2 | 11/2000 |
| WO | WO-00/69900 A2 | 11/2000 |
| WO | WO-01/36620 A2 | 5/2001 |
| WO | WO-01/44284 A2 | 6/2001 |
| WO | WO-01/80890 A2 | 11/2001 |
| WO | WO-02/15918 A2 | 2/2002 |
| WO | WO-02/47871 A1 | 6/2002 |
| WO | WO-02/067639 A1 | 8/2002 |
| WO | WO-02/068579 A2 | 9/2002 |
| WO | WO-02/074234 A2 | 9/2002 |
| WO | WO-03/074082 A1 | 9/2003 |
| WO | WO-03/079979 A2 | 10/2003 |
| WO | WO-03/092581 A2 | 11/2003 |
| WO | WO-03/094835 A2 | 11/2003 |
| WO | WO-2004/011498 A2 | 2/2004 |
| WO | WO-2004/022579 A2 | 3/2004 |
| WO | WO-2004/046194 A2 | 6/2004 |
| WO | WO-2004/047871 A2 | 6/2004 |
| WO | WO-2004/062555 A2 | 7/2004 |
| WO | WO-2004/074320 A2 | 9/2004 |
| WO | WO-2004/094460 A2 | 11/2004 |
| WO | WO-2005/000095 A2 | 1/2005 |
| WO | WO-2005/007809 A2 | 1/2005 |
| WO | WO-2005/042034 A1 | 5/2005 |
| WO | WO-2005/047337 A1 | 5/2005 |
| WO | WO-2005/070446 A1 | 8/2005 |
| WO | WO-2005/072055 A2 | 8/2005 |
| WO | WO-2005/094890 A1 | 10/2005 |
| WO | WO-2005/098490 A1 | 10/2005 |
| WO | WO-2005/103263 A1 | 11/2005 |
| WO | WO-2006/005140 A2 | 1/2006 |
| WO | WO-2006/026663 A1 | 3/2006 |
| WO | WO-2006/039480 A2 | 4/2006 |
| WO | WO-2006/060641 A2 | 6/2006 |
| WO | WO-2006/110743 A1 | 10/2006 |
| WO | WO-2006/116260 A2 | 11/2006 |
| WO | WO-2007/041645 A2 | 4/2007 |
| WO | WO-2007/071295 A1 | 6/2007 |
| WO | WO-2007/097923 A2 | 8/2007 |
| WO | WO-2008/021872 A1 | 2/2008 |
| WO | WO-2008/030558 A2 | 3/2008 |
| WO | WO-2008/031045 A2 | 3/2008 |
| WO | WO-2008/053362 A2 | 5/2008 |
| WO | WO-2008/058016 A2 | 5/2008 |
| WO | WO-2008/079995 A2 | 7/2008 |
| WO | WO-2008/088422 A2 | 7/2008 |
| WO | WO-2008/109903 A1 | 9/2008 |
| WO | WO-2008/136611 A1 | 11/2008 |
| WO | WO-2008/138131 A1 | 11/2008 |
| WO | WO-2008/154226 A1 | 12/2008 |
| WO | WO-2009/006520 A1 | 1/2009 |
| WO | WO-2009/006732 A9 | 1/2009 |
| WO | WO-2009/015011 A1 | 1/2009 |
| WO | WO-2009/023270 A2 | 2/2009 |
| WO | WO-2009/033680 A2 | 3/2009 |
| WO | WO-2009/033724 A1 | 3/2009 |
| WO | WO-2009/033796 A1 | 3/2009 |
| WO | WO-2009/033807 A2 | 3/2009 |
| WO | WO-2009/034134 A2 | 3/2009 |
| WO | WO-2009/036448 A2 | 3/2009 |
| WO | WO-2009/040030 A1 | 4/2009 |
| WO | WO-2009/040031 A1 | 4/2009 |
| WO | WO-2009/040083 A2 | 4/2009 |
| WO | WO-2009/046861 A1 | 4/2009 |
| WO | WO-2009/058322 A1 | 5/2009 |
| WO | WO-2009/067639 A2 | 5/2009 |
| WO | WO-2009/086126 A2 | 7/2009 |
| WO | WO-2009/090553 A2 | 7/2009 |
| WO | WO-2009/142307 A1 | 11/2009 |
| WO | WO-2009/149161 A9 | 12/2009 |
| WO | WO-2009/156481 A1 | 12/2009 |
| WO | WO-2009/158035 A2 | 12/2009 |
| WO | WO-2010/002583 A2 | 1/2010 |
| WO | WO-2010/011096 A2 | 1/2010 |
| WO | WO-2010/048308 A2 | 4/2010 |
| WO | WO-2010/078325 A2 | 7/2010 |
| WO | WO-2010/082804 A2 | 7/2010 |
| WO | WO-2010/117760 A2 | 10/2010 |
| WO | WO-2010/129655 A2 | 11/2010 |
| WO | WO-2010/135541 A2 | 11/2010 |
| WO | WO-2011/134084 A1 | 11/2011 |
| WO | WO-2012/088608 A1 | 7/2012 |
| WO | WO-2012/099851 A2 | 7/2012 |
| WO | WO-2013/058833 A1 | 4/2013 |
| WO | WO-2013/059491 A1 | 4/2013 |
| WO | WO-2015/112015 A1 | 7/2015 |
| WO | WO-2016/007873 A1 | 1/2016 |
| WO | WO-2016/090251 A1 | 6/2016 |
| WO | WO-2016/123342 A2 | 8/2016 |
| WO | WO-2017/031114 A1 | 2/2017 |
| WO | WO-2017/058822 A1 | 4/2017 |
| WO | WO-2017/074466 A1 | 5/2017 |
| WO | WO-2017/155569 A1 | 9/2017 |
| WO | WO-2017/171871 A1 | 10/2017 |
| WO | WO-2017/173395 A1 | 10/2017 |
| WO | WO-2017/173413 A1 | 10/2017 |
| WO | WO-2017/214130 A1 | 12/2017 |
| WO | WO-2018/004517 A1 | 1/2018 |
| WO | WO-2018/035420 A1 | 2/2018 |

OTHER PUBLICATIONS

Taketani et al., "Clinical and genetic aspects of hypophosphatasia in Japanese patients," Arch Dis Child. 99(3):211-5 (2014) (6 pages).

Whyte, "Physiological role of alkaline phosphatase explored in hypophosphatasia," Ann N Y Acad Sci. 1192:190-200 (2010).

Whyte et al., "Alkaline phosphatase: placental and tissue-nonspecific isoenzymes hydrolyze phosphoethanolamine, inorganic pyrophosphate, and pyridoxal 5'-phosphate. Substrate accumulation in carriers of hypophosphatasia corrects during pregnancy," J Clin Invest. 95(4):1440-5 (1995).

International Search Report and Written Opinion for International Patent Application No. PCT/US2015/064003, dated Mar. 31, 2016 (13 pages).

Ali et al., "Isolation and characterization of calcifying matrix vesicles from epiphyseal cartilage," Proc Natl Acad Sci USA. 67(3):1513-1520 (1970).

Anderson et al., "Pyrophosphate stimulation of calcium uptake into cultured embryonic bones. Fine structure of matrix vesicles and their role in calcification," Dev Biol. 34:211-227 (1973).

Anderson et al., "Sustained osteomalacia of long bones despite major improvement in other hypophosphatasia-related mineral deficits in tissue nonspecific alkaline phosphatase/nucleotide pyrophosphatase phosphodiesterase 1 double-deficient mice," Am J Pathol. 166(6):1711-1720 (2005).

Anderson et al., "The role of matrix vesicles in growth plate development and biomineralization," Front Biosci. 10:822-837 (2005).

Beertsen et al., "Root development in mice lacking functional tissue non-specific alkaline phosphatase gene: Inhibition of acellular cementum formation," J Dent Res. 78(6):1221-1229 (1999) (10 pages).

Bennett et al., "Extracellular domain-IgG fusion proteins for three human natriuretic peptide receptors," J Biol Chem. 266(34):23060-23067 (1991).

Bernard, "Ultrastructural localization of alkaline phosphatase in initial intramembranous osteogenesis," Clin Orthop Relat Res. 135:218-225 (1978).

Bonilla, "Pharmacokinetics of immunoglobulin administered via intravenous or subcutaneous routes," Immunol Allergy Clin N Am. 28:803-819 (2008).

Byers et al., "Effect of enzyme replacement therapy on bone formation in a feline model of mucopolysaccharidosis type VI," Bone. 21(5):425-431 (1997).

Cameron et al., "Minireview: Natriuretic peptides during development of the fetal heart and circulation," Endocrinology. 144(6):2191-2194 (2003).

(56) References Cited

OTHER PUBLICATIONS

Clemens et al., "Pharmacokinetics and biological actions of subcutaneously administered human brain natriuretic peptide," J Pharmacol Exp Ther. 287(1):67-71 (1998).
Declaration of Dr. Philippe Crine for EP 08757088.3, executed Jan. 14, 2011 (6 pages).
Engel et al., "Characterization of the hormone binding site of natriuretic peptide receptor-C," FEBS Lett. 360:169-172 (1995).
Extended European Search Report for European Application No. 08757088.3, dated Jun. 21, 2010 (6 pages).
Farley et al., "Effects of tunicamycin, mannosamine, and other inhibitors of glycoprotein processing on skeletal alkaline phosphatase in human osteoblast-like cells," Calcif Tissue Int. 76:63-74 (2005).
Fedde et al., "Alkaline phosphatase knock-out mice recapitulate the metabolic and skeletal defects of infantile hypophosphatasia," available in PMC Mar. 7, 2011, published in final edited form as: J Bone Miner Res. 14(12):2015-2026 (1999) (19 pages).
Garg, Investigation of the role of FcRn in the absorption, distribution, and elimination of monoclonal antibodies. Dissertation: State University of New York at Buffalo, 2007 (Abstract only) (2 pages).
Greenberg et al., "A homoallelic $Gly^{317}$ to Asp mutation in ALPL causes the perinatal (lethal) form of hypophosphatasia in Canadian mennonites," Genomics. 17:215-217 (1993).
Harmey et al., "Concerted regulation of inorganic pyrophosphate and osteopontin by Akp2, Enpp1, and Ank," Am J Pathol. 164(4):1199-1209 (2004).
Harmey et al., "Elevated skeletal osteopontin levels contribute to the hypophosphatasia phenotype in $Akp2^{-/-}$ mice," J Bone Miner Res. 21(9):1377-1386 (2006).
Hawrylak et al., "The solubilization of tetrameric alkaline phosphatase from human liver and its conversion into various forms by phosphatidylinositol phospholipase C or proteolysis," J Biol Chem. 263(28):14368-14373 (1988).
Henthorn et al., "Different missense mutations at the tissue-nonspecific alkaline phosphatase gene locus in autosomal recessively inherited forms of mild and severe hypophosphatasia," Proc Natl Acad Sci USA. 89:9924-9928 (1992).
Hessle et al., "Tissue-nonspecific alkaline phosphatase and plasma cell membrane glucoprotein-1 are central antagonistic regulators of bone mineralization," Proc Natl Acad Sci USA. 99(14): 9445-9449 (2002).
Jansonius, "Structure, evolution and action of vitamin $B_6$-dependent enzymes," Curr Opin Struct Biol. 8:759-769 (1998).
Jin et al., "Novel analog of atrial natriuretic peptide selective for receptor-A produces increased diuresis and natriuresis in rats," J Clin Invest. 98(4):969-976 (1996).
Johnson et al., "Matrix vesicle plasma cell membrane glycoprotein-1 regulates mineralization by murine osteoblastic MC3T3 cells," J Bone Miner Res. 14(6):883-892 (1999).
Kochendoerfer, "Protein & peptide drug delivery—third international conference: Minimally invasive delivery methods," Sep. 22-23, Philadelphia, PA. IDrugs. 6(11):1043-1045 (2003).
Kostenuik et al., "Infrequent delivery of a long-acting PTH-Fc fusion protein has potent anabolic effects on cortical and cancellous bone," J Bone Miner Res. 22(10):1534-1547 (2007).
Mahmood et al., "Selection of the first-time dose in humans: comparison of different approaches based on interspecies scaling of clearance," J Clin Pharmacol. 43:692-697 (2003).
Millan, "Mammalian Alkaline Phosphatases," Wiley-WCH Verlag GmbH & Co., Weinheim, Germany, 1-322 (2006).
Morris et al., "Immunolocalization of alkaline phosphatase in osteoblasts and matrix vesicles of human fetal bone," Bone Miner. 19:287-298 (1992).
Nasu et al., "Aberrant interchain disulfide bridge of tissue-nonspecific alkaline phosphatase with an Arg433 to Cys substitution associated with severe hypophosphatasia," FEBS Journal. 273:5612-5624 (2006).
NCBI Protein Database Accession No. AAF64516. Retrieved on Apr. 16, 2013 (2 pages).
NCBI Protein Database Accession No. AAC33858. Retrieved on Apr. 16, 2013 (1 page).
NCBI Protein Database Accession No. AAH21289. Retrieved on Apr. 16, 2013 (2 pages).
NCBI Protein Database Accession No. AAH66116. Retrieved on Apr. 16, 2013 (2 pages).
NCBI Protein Database Accession No. AAH90861. Retrieved on Apr. 16, 2013 (2 pages).
NCBI Protein Database Accession No. AAI10910. Retrieved on Apr. 16, 2013 (2 pages).
NCBI Protein Database Accession No. AAI26166. Retrieved on Apr. 16, 2013 (2 pages).
NCBI Protein Database Accession No. AAI18209. Retrieved on Apr. 17, 2013 (2 pages).
NCBI Protein Database Accession No. AAN64273. Retrieved on Apr. 16, 2013 (1 page).
NCBI Protein Database Accession No. NP_000469. Retrieved on Apr. 16, 2013 (3 pages).
NCBI Protein Database Accession No. NP_001623. Retrieved on Apr. 16, 2013 (3 pages).
NCBI Protein Database Accession No. NP_001036028. Retrieved on Apr. 16, 2013 (2 pages).
NCBI Protein Database Accession No. NP_001253798.1, downloaded Apr. 17, 2013. (2 pages).
NCBI Protein Database Accession No. NP_112603. Retrieved on Apr. 16, 2013 (3 pages).
NCBI Protein Database Accession No. P05186. Retrieved on Apr. 16, 2013 (19 pages).
NCBI Protein Database Accession No. P05187. Retrieved on Apr. 16, 2013 (10 pages).
NCBI Protein Database Accession No. P08289. Retrieved on Apr. 16, 2013 (5 pages).
NCBI Protein Database Accession No. P09487. Retrieved on Apr. 16, 2013 (4 pages).
NCBI Protein Database Accession No. P09242. Retrieved on Apr. 16, 2013 (6 pages).
NCBI Protein Database Accession No. P09923. Retrieved on Apr. 16, 2013 (6 pages).
NCBI Protein Database Accession No. P10696. Retrieved on Apr. 16, 2013 (7 pages).
NCBI Protein Database Accession No. Q29486. Retrieved on Apr. 16, 2013 (3 pages).
NCBI Protein Database Accession No. Q9N0V0. Retrieved on Apr. 16, 2013 (1 page).
Nosjean et al., "Human tissue non-specific alkaline phosphatases: sugar-moiety-induced enzymic and antigenic modulations and genetic aspects," Biochem J. 321:297-303 (1997).
Ramachandran et al., "Treatment of an anabolic bone deficiency in neurofibromatosis with bone morphogenetic proteins and its potential application for congenital pseudarthrosis of the tibia," J Bone Joint Surg Br. 91-B (Suppl. 1), Abstract 137 (2009).
Srinivas et al., "Assessment of dose proportionality, absolute bioavailability, and immunogenicity response of CTLA4Ig (BMS-188667), a novel immunosuppressive agent, following subcutaneous and intravenous administration to rats," Pharmaceutical Res. 14(7): 911-916 (1997).
Tye et al., "Delineation of the hydroxyapatite-nucleating domains of bone sialoprotein," J Biol Chem. 278(10):7949-7955 (2003).
Urlaub et al., "Deletion of the diploid dihydrofolate reductase locus from cultured mammalian cells," Cell. 33:405-412 (1983).
Wang et al., "A mouse model for achondroplasia produced by targeting fibroblast growth factor receptor 3," Proc Natl Acad Sci USA. 96:4455-4460 (1999).
Wang et al., "Structure-based chemical modification strategy for enzyme replacement treatment of phenylketonuria," Mol Genet Metab. 86:134-140 (2005).
Weiss et al., "A missense mutation in the human liver/bone/kidney alkaline phosphatase gene causing a lethal form of hypophosphatasia," Proc Natl Acad Sci USA. 85:7666-7669 (1988).
Whyte et al., "Enzyme-replacement therapy in life-threatening hypophosphatasia," N Engl J Med. 366(10):904-13 (2012).

(56) References Cited

OTHER PUBLICATIONS

Whyte et al., "Markedly increased circulating pyridoxal-5'-phosphate levels in hypophosphatasia," J Clin Invest. 76:752-756 (1985).
Wroblewski et al., "Pharmacokinetics, metabolic stability, and subcutaneous bioavailability of a genetically engineered analog of DcR3, flint [DcR3(R218Q)], in cynomolgus monkeys and mice," Drug Metab Dispos. 31(4):502-507 (2003).
Yamamoto et al., "Long term phenotypic correction of severe infantile hypophosphatasia in a mouse model by neonatal injection of lentiviral vector," Mol Ther. 17:S67-S68, Abstract 171 (2009).
Zierhut et al., "Population PK-PD model for Fc-osteoprotegerin in healthy postmenopausal women," J Pharmacokinet Pharmacodyn. 35:379-399 (2008).
Zurutuza et al., "Correlations of genotype and phenotype in hypophosphatasia," Hum Mol Genet. 8(6):1039-1046 (1999).
International Preliminary Report on Patentability for International Patent Application No. PCT/CA2011/050258, dated Nov. 15, 2012 (9 pages).
International Search Report and Written Opinion for International Patent Application No. PCT/US2012/039004, dated Nov. 2, 2012 (22 pages).
Invitation to Pay Additional Fees for International Patent Application No. PCT/US2012/039004, dated Aug. 29, 2012 (2 pages).
Oikawa et al., "Enzyme replacement therapy on hypophosphatasia mouse model," J Inherit Metab Dis. 9 pages (2013).
Whyte et al., "Infantile hypophosphatasia: normalization of circulating bone alkaline phosphatase activity followed by skeletal remineralization. Evidence for an intact structural gene for tissue nonspecific alkaline phosphatase," J Pediatr. 108(1):82-8 (1986).
Achord et al., "Human beta-glucuronidase: in vivo clearance and in vitro uptake by a glycoprotein recognition system on reticuloendothelial cells," Cell 15(1):269-278 (1978).
Anderson et al., "Matrix vesicles in osteomalacic hypophosphatasia bone contain apatite-like mineral crystals," Am J Pathol. 151(6):1555-61 (1997).
Barton et al., "Replacement therapy for inherited enzyme deficiency—macrophage-targeted glucocerebrosidase for Gaucher's disease," N Engl J Med. 324(21):1464-70 (1991) (abstract only).
Bernardi, "Chromatography of proteins on hydroxyapatite," Methods Enzymol. 27:471-9 (1973).
Boskey et al., "Matrix vesicles promote mineralization in a gelatin gel," Calcif Tissue Int 60(3):309-15 (1997).
Ciancaglini et al., "Contribution of matrix vesicles and alkaline phosphatase to ectopic bone formation," Braz. J Med Biol Res. 39(5):603-10 (2006).
Crawley et al., "Enzyme replacement therapy in a feline model of Maroteaux-Lamy Syndrome," J Clin Invest. 97(8):1864-73 (1996).
Di Mauro et al., "Kinetic characterization of hypophosphatasia mutations with physiological substrates," J Bone Miner Res. 17(8):1383-91 (2002).
Dumont et al., "Monomeric Fc fusions: impact on pharmacokinetic and biological activity of protein therapeutics," BioDrugs. 20(3):151-60 (2006).
Eng et al., "Safety and efficacy of recombinant human alpha-galactosidase A—replacement therapy in Fabry's disease," N Engl J Med. 345(1):9-16 (2001).
Gilbert et al., "Chimeric peptides of statherin and osteopontin that bind hydroxyapatite and mediate cell adhesion," J Biol Chem. 275(21):16213-8 (2000).
Guo et al., "Protein tolerance to random amino acid change," Proc Natl Acad Sci USA. 101(25):9205-9210 (2004).
Henthorn et al., "Missense mutations of the tissue-nonspecific alkaline phosphatase gene in hypophosphatasia," Clin Chem. 38(12):2501-5 (1992).
Hosain et al., "Targeted delivery of antineoplastic agent to bone: biodistribution studies of technetium-99m-labeled gem-bisphosphonate conjugate of methotrexate," J Nucl Med. 37(1):105-7 (1996).
Kakkis et al., "Enzyme-replacement therapy in mucopolysaccharidosis I," N Engl J Med. 344(3):182-8 (2001).
Kaufmann et al., "Influence of low temperature on productivity, proteome and protein phosphorylation of CHO cells," Biotechnol Bioeng. 63(5):573-82 (1999).
Murray, "Lectin-specific targeting of lysosomal enzymes to reticuloendothelial cells," Methods Enzymol. 149:25-42 (1987).
Oda et al., "A general method for rapid purification of soluble versions of glycosylphosphatidylinositol-anchored proteins expressed in insect cells: an application for human tissue-nonspecific alkaline phosphatase," J Biochem. 126(4):694-9 (1999).
Pedersen et al., "Removal of N-terminal polyhistidine tags from recombinant proteins using engineered aminopeptidases," Protein Expr Purif. 15(3):389-400 (1999).
Salih et al., "Identification of the phosphorylated sites of metabolically 32P-labeled osteopontin from cultured chicken osteoblasts," J Biol Chem. 272(21):13966-73 (1997).
Sands et al., "Enzyme replacement therapy for murine mucopolysaccharidosis type VII," J Clin Invest. 93(6):2324-31 (1994).
Sekido et al., "Novel drug delivery system to bone using acidic oligopeptide: pharmacokinetic characteristics and pharmacological potential," J Drug Target. 9(2):111-21 (2001).
Sturtz et al., "A study of the delivery-targeting concept applied to antineoplasic drugs active on human osteosarcoma. I. Synthesis and biological activity in nude mice carrying human osteosarcoma xenografts of gem-bisphosphonic methotrexate analogues," Eur J Med Chemistry. 27:825-33 (1992).
Tomatsu, Declaration Under 37 C.F.R. § 1.132 for U.S. Appl. No. 11/484,870, dated Jun. 1, 2009 (3 pages).
Uludag et al., "Bone affinity of a bisphosphonate-conjugated protein in vivo," Biotechnol Prog. 16(6):1115-8 (2000).
Waymire et al., "Mice lacking tissue non-specific alkaline phosphatase die from seizures due to defective metabolism of vitamin B-6," Nat Genet. 11(1):45-51 (1995).
Weinberg, "An overview of infliximab, etanercept, efalizumab, and alefacept as biologic therapy for psoriasis," Clin Ther. 25(10):2487-505 (2003).
Weiss et al., "Isolation and characterization of a cDNA encoding a human liver/bone/kidney-type alkaline phosphatase," Proc Natl Acad Sci USA. 83(19):7182-6 (1986).
Weiss et al., "Structure of the human liver/bone/kidney alkaline phosphatase gene," J Biol Chem. 263(24):12002-10 (1988).
Weninger et al., "Biochemical and morphological effects of human hepatic alkaline phosphatase in a neonate with hypophosphatasia," Acta Paediatr Scand. Suppl. 360:154-160 (1989).
Whyte et al., "Infantile hypophosphatasia: enzyme replacement therapy by intravenous infusion of alkaline phosphatase-rich plasma from patients with Paget bone disease," J Pediatr. 101(3):379-86 (1982).
Whyte et al., "Enzyme replacement therapy for infantile hypophosphatasia attempted by intravenous infusions of alkaline phosphatase-rich Paget plasma: results in three additional patients," J Pediatr. 105(6):926-33 (1984).
Whyte et al., "Hypophosphatasia," in The Metabolic and Molecular Bases of Inherited Disease (8th ed.), pp. 5313-5329, 2001 (McGraw-Hill Book Company) (epub pp. 1-41).
Whyte et al., "Heritable Forms of Rickets and Osteomalacia," in Connective Tissues and Its Heritable Disorders, pp. 765-787, 2002 (eds. R.M. Royce and B. Steinmann, Wiley-Liss, Inc. Hoboken).
Whyte et al., "Marrow cell transplantation for infantile hypophosphatasia," J Bone Miner Res. 18(4):624-36 (2003).
Yamamoto et al., "Prolonged survival and phenotypic correction of Akp2(-/-) hypophosphatasia mice by lentiviral gene therapy," J Bone Miner Res. 26(1):135-42 (2011).
Communication from Examining Division for European Application No. EP 05 73 9065.0, dated Jun. 18, 2009 (6 pages).
Communication from Examining Division for European Application No. EP 05 73 9065.0, dated Jun. 11, 2010 (5 pages).
Office Action for U.S. Appl. No. 12/793,517, dated Aug. 16, 2010 (9 pages).
Office Action for U.S. Appl. No. 13/071,445, dated Feb. 6, 2012 (12 pages).

(56) References Cited

OTHER PUBLICATIONS

Supplementary European Search Report for European Application No. EP 05 73 9065 (date of completion of search Nov. 7, 2008, dated Dec. 2, 2008) (3 pages).
Choe et al., "Substrate profiling of cysteine proteases using a combinatorial peptide library identifies functionally unique specificities," J Biol Chem. 281(18):12824-12832 (2006).
Official Action for Japanese Application No. 2013-544989, dated Oct. 27, 2015 (3 pages).
Harris, "The human alkaline phosphatases: what we know and what we don't know," Clin Chim Acta. 186:133-50 (1989).
De la Croix Ndong et al., "Asfotase-alpha improves bone growth, mineralization and strength in mouse models of neurofibromatosis type-1," Nat Med. 20(8):904-10 (2014) (10 pages).
International Search Report and Written Opinion for International Patent Application No. PCT/US2016/047166, dated Nov. 7, 2016 (15 pages).
Ratner, "Alexion pays big for Synageva's rare disease drug candidate," Nat Biotechnol. 33(7):679 (2015).
Addison et al., "Pyrophosphate inhibits mineralization of osteoblast cultures by binding to mineral, up-regulating osteopontin, and inhibiting alkaline phosphatase activity," J Biol Chem. 282(21):15872-15883 (2007).
Advisory Action for U.S. Appl. No. 11/484,870, dated Dec. 20, 2007 (4 pages).
Altarescu et al., "The efficacy of enzyme replacement therapy in patients with chronic neuronopathic Gaucher's disease," J Pediatr. 138(4):539-547 (2001).
Anderson et al., "Impaired calcification around matrix vesicles of growth plate and bone in alkaline phosphatase-deficient mice," Am J Pathol. 164:841-847 (2004).
Barranger et al., "Lessons learned from the development of enzyme therapy for Gaucher disease," J Inherit Metab Dis. 24(Supp 2):89-96 (2001).
Bobé et al., "Fas-mediated liver damage in MRL hemopoietic chimeras undergoing lpr-mediated graft-versus-host disease," J Immunol. 159:4197-4204 (1997).
Boskey, "Amorphous calcium phosphate: the contention of bone," J Dent Res. 76:1433-1436 (1997).
Campbell et al., "Insulin-like growth factor (IGF)-binding protein-5-(201-218) region regulates hydroxyapatite and IGF-I binding," Am J Physiol. 273:E1005-1013 (1997).
Cleland et al., "Emerging protein delivery methods," Curr Opin Biotechnol. 12:212-219 (2001).
Communication from Examining Division for European Application No. EP 08 757 088.3, dated Apr. 20, 2011 (4 pages).
Data Sheet for pFUSE-SEAP-hFC "Plasmid designed for the expression of a SEAP-Fc Fusion protein," Invivogen, San Diego, CA (4 pages) (1989).
Extended European Search Report for European Application No. 11774253.6, dated Oct. 14, 2013 (8 pages).
Extended European Search Report for European Application No. EP 11 00 0196.3, dated Jun. 22, 2011 (6 pages).
Extended European Search Report for European Application No. EP 11 00 4496.3, dated Aug. 26, 2011 (7 pages).
Fujisaki et al., "Osteotropic Drug Delivery System (ODDS) based on bisphosphonic prodrug. IV effects of osteotropic estradiol on bone mineral density and uterine weight in ovariectomized rats," J Drug Target. 5(2):129-138 (1997) (11 pages).
Fujisawa et al., "Acidic amino acid-rich sequences as binding sites of osteonectin to hydroxyapatite crystals," Biochim Biophys Acta. 1292:53-60 (1996).
Furbish et al., "Uptake and distribution of placental glucocerebrosidase in rat hepatic cells and effects of sequential deglycosylation," Biochim Biophys Acta. 673:425-434 (1981).
Halling Linder et al., "Glycosylation differences contribute to distinct catalytic properties among bone alkaline phosphatase isoforms," available in PMC Nov. 1, 2010, published in final edited form as: Bone. 45(5):987-993 (2009) (17 pages).

Hardy et al., "Dissection of a carboxy-terminal region of the yeast regulatory protein RAP1 with effects on both transcriptional activation and silencing," Mol Cell Biol. 12(3):1209-1217 (1992).
Hult et al., "Engineered enzymes for improved organic synthesis," Curr Opin Biotechnol. 14:395-400 (2003).
Hunter et al., "Modulation of crystal formation by bone phosphoproteins: structural specificity of the osteopontin-mediated inhibition of hydroxyapatite formation," Biochem J. 300:723-728 (1994).
Ikezawa, "Glycosylphosphatidylinositol (GPI)-anchored proteins," *Biol Pharm Bull*. 25(4):409-417 (2002).
International Search Report and Written Opinion for International Patent Application No. PCT/CA2005/000615, dated Aug. 18, 2005 (14 pages).
International Search Report and Written Opinion for International Patent Application No. PCT/CA2008/000923, dated Sep. 12, 2008 (11 pages).
International Search Report and Written Opinion for International Patent Application No. PCT/CA2011/050258, dated Jul. 29, 2011 (14 pages).
Kasugai et al., "Selective drug delivery system to bone: small peptide $(Asp)_6$ conjugation," J Bone Miner Res. 15(5):936-943 (2000).
Leone et al., "Allosteric modulation of pyrophosphatase activity of rat osseous plate alkaline phosphatase by magnesium ions," Int J Biochem Cell Biol. 30:89-97 (1998).
Meyer, "Can biological calcification occur in the presence of pyrophosphate?" Arch Biochem Biophys. 231:1-8 (1984).
Michigami et al., "Common mutations F310L and T1559del in the tissue-nonspecific alkaline phosphatase gene are related to distinct phenotypes in Japanese patients with hypophosphatasia," Eur J Pediatr. 164:277-282 (2005).
Moss et al., "Association of inorganic-pyrophosphatase activity with human alkaline-phosphatase preparations," Biochem J. 102:53-57 (1967).
Murshed et al., "Unique coexpression in osteoblasts of broadly expressed genes accounts for the spatial restriction of ECM mineralization to bone," Genes Dev. 19:1093-1104 (2005).
Narisawa et al., "Abnormal vitamin B6 metabolism in alkaline phosphatase knock-out mice causes multiple abnormalities, but not the impaired bone mineralization," J Pathol. 193:125-133 (2001).
Narisawa et al., "Inactivation of two mouse alkaline phosphatase genes and establishment of a model of infantile hypophosphatasia," Dev Dyn. 208:432-446 (1997).
NCBI Protein Database Accession No. NP_001622. Retrieved on Apr. 16, 2013 (3 pages).
NCBI Protein Database Accession No. NP_031457. Retrieved on Apr. 16, 2013 (3 pages).
NCBI Protein Database Accession No. NP_037191. Retrieved on Apr. 16, 2013 (3 pages).
NCBI Protein Database Accession No. NP_776412. Retrieved on Apr. 17, 2013 (2 pages).
NCBI Protein Database Accession No. NP_789828. Retrieved on Apr. 16, 2013 (3 pages).
NCBI Protein Database Accession No. P01857. Retrieved on Apr. 18, 2013 (7 pages).
NCBI Protein Database Accession No. Q6PYX1. Retrieved on Oct. 15, 2013 (2 pages).
Ngo et al., Computational complexity, protein structure prediction, and the levinthal paradox. *The Protein Folding Problem and Tertiary Structure Prediction*. Merz et al. (ed.), 433, 492-495 (1994).
Nishioka et al., "Enhancement of drug delivery to bone: characterization of human tissue-nonspecific alkaline phosphatase tagged with an acidic oligopeptide," Mol Genet Metab. 88:244-255 (2006).
Office Action for U.S. Appl. No. 11/111,664, dated Dec. 4, 2008 (7 pages).
Office Action for U.S. Appl. No. 11/111,664, dated May 14, 2008 (8 pages).
Office Action for U.S. Appl. No. 11/111,664, dated Oct. 4, 2007 (11 pages).
Office Action for U.S. Appl. No. 11/484,870, dated Aug. 11, 2009 (15 pages).
Office Action for U.S. Appl. No. 11/484,870, dated Feb. 2, 2009 (16 pages).

(56) References Cited

OTHER PUBLICATIONS

Office Action for U.S. Appl. No. 11/484,870, dated Jan. 25, 2007 (15 pages).
Office Action for U.S. Appl. No. 11/484,870, dated Jul. 5, 2007 (13 pages).
Office Action for U.S. Appl. No. 11/484,870, dated Jun. 25, 2008 (16 pages).
Office Action for U.S. Appl. No. 11/484,870, dated Oct. 1, 2007 (12 pages).
Office Action for U.S. Appl. No. 12/405,920, dated Aug. 9, 2010 (7 pages).
Office Action for U.S. Appl. No. 12/405,920, dated Dec. 17, 2009 (14 pages).
Office Action for U.S. Appl. No. 13/071,445, dated May 25, 2012 (14 pages).
Official Notification and Search Report for Eurasian Patent Application No. 201291138, dated May 17, 2013 (3 pages).
Patti et al.,"Critical residues in the ligand-binding site of the *Staphylococcus aureus* collagen-binding adhesin (MSCRAMM)," J Biol Chem. 270(20):12005-12011 (1995).
Reply to Final Office Action for U.S. Appl. No. 13/071,445, dated Oct. 25, 2012 (14 pages).
Reply to Office Action for U.S. Appl. No. 11/111,664, dated Sep. 10, 2008 (32 pages).
Restriction Requirement for U.S. Appl. No. 12/599,679, dated Jun. 12, 2012 (5 pages).
Rezende et al., "Inorganic pyrophosphate-phosphohydrolytic activity associated with rat osseous plate alkaline phosphatase," Cell Mol Biol. 44(2):293-302 (1998).
Rowe et al., "MEPE, a new gene expressed in bone marrow and tumors causing osteomalacia," Genomics. 67:54-68 (2000).
Russell et al., "Inorganic pyrophosphate in plasma in normal persons and in patients with hypophosphatasia, osteogenesis imperfecta, and other disorders of bone," J Clin Invest. 50:961-969 (1971).
Sharom et al., "Glycosylphosphatidylinositol-anchored proteins: structure, function, and cleavage by phosphatidylinositol-specific phospholipase C," Biochem Cell Biol. 80:535-549 (2002).
Shull et al., "Enzyme replacement in a canine model of Hurler syndrome," Proc Natl Acad Sci USA. 91:12937-12941 (1994).
Spears et al., "Deoxyuridylate effects on thymidylate synthase-5-fluorodeoxyuridylate-folate ternary complex formation," Biochem Pharmacol. 38(18):2985-2993 (1989).
Stahl et al., "Evidence for receptor-mediated binding of glycoproteins, glycoconjugates, and lysosomal glycosidases by alveolar macrophages," Proc Natl Acad Sci USA. 75(3):1399-1403 (1978).
Extended European Search Report for European Application No. EP 08757088, date of completion Jun. 7, 2010 (6 pages).
Symersky et al., "Structure of the collagen-binding domain from a *Staphylococcus aureus* adhesin," Nat Struct Biol. 4(10):833-838 (1997).
Tomatsu, Declaration Under 37 C.F.R. § 1.132 for U.S. Appl. No. 11/484,870, dated Nov. 27, 2007 (2 pages).
Whyte, "Hypophosphatasia and the role of alkaline phosphatase in skeletal mineralization," Endocr Rev. 15(4):439-461 (1994).
Whyte, "Hypophosphatasia: Nature's window on alkaline phosphatase function in man," *Principles of Bone Biology*, 2nd ed., Bilezikian, Raisz, and Rodan. 2:1229-1248 (2002).
Yadav et al., "Dose response of bone-targeted enzyme replacement for murine hypophosphatasia," available in PMC Aug. 1, 2012, published in final edited form as: Bone. 49(2):250-6 (2011) (20 pages).
Yokogawa et al., "Selective delivery of estradiol to bone by aspartic acid oligopeptide and its effects on ovariectomized mice," Endocrinology. 142(3):1228-1233 (2001).
Young et al., "Structure, expression, and regulation of the major noncollagenous matrix proteins of bone," Clin Orthop Relat Res. 281:275-294 (1992).
Orimo, "The mechanism of mineralization and the role of alkaline phosphatase in health and disease," J Nippon Med Sch. 77(1):4-12 (2010).
Attwood, "The Babel of Bioinformatics," Genomics. 290(5491):471-3 (2000).
Skolnick et al., "From genes to protein structure and function: novel applications of computational approaches in the genomic era," Trends Biotechnol. 18(1):34-9 (2000).
Bocciardi et al., "Overexpression of the C-type natriuretic peptide (CNP) is associated with overgrowth and bone anomalies in an individual with balanced t(2;7) translocation," Hum Mutat. 28(7):724-731 (2007).
Brenner et al., "Diverse biological actions of atrial natriuretic peptide," Physiol Rev. 70(3):665-699 (1990).
Chen et al., "Gly369Cys mutation in mouse FGFR3 causes achondroplasia by affecting both chondrogenesis and osteogenesis," J Clin Invest. 104(11):1517-1525 (1999).
Chusho et al., "Dwarfism and early death in mice lacking C-type natriuretic peptide," Proc Natl Acad Sci USA. 98(7):4016-4021 (2001).
Daggubati et al., "Adrenomedullin, endothelin, neuropeptide Y, atrial, brain, and C-natriuretic prohormone peptides compared as early heart failure indicators," Cardiovasc Res. 36:246-255 (1997).
De Plater et al., "The natriuretic peptide (OVCNP-39) from platypus (*Ornithorhynchus anatinus*) venom relaxes the isolated rat uterus and promotes oedema and mast cell histamine release," Toxicon. 36(3):847-857 (1998).
Furuya et al., "Structural requirements of C-type natriuretic peptide for elevation of cyclic GMP in cultured vascular smooth muscle cells," Biochem Biophys Res Commun. 183(3):964-969 (1992).
Hagiwara et al., "Autocrine regulation of rat chondrocyte proliferation by natriuretic peptide C and its receptor, natriuretic peptide receptor-B," J Biol Chem. 269(14):10729-10733 (1994).
Hagiwara et al., "cGMP produced in response to ANP and CNP regulates proliferation and differentiation of osteoblastic cells," Am J Physiol. 270:C1311-C1318 (1996).
Horton et al., "Achondroplasia," Lancet. 370:162-172, 2007.
Inoue et al., "Four functionally distinct C-type natriuretic peptides found in fish reveal evolutionary history of the natriuretic peptide system," Proc Natl Acad Sci USA. 100(17):10079-10084 (2003).
International Search Report and Written Opinion for International Patent Application No. PCT/CA2011/050807, dated Apr. 13, 2012 (18 pages).
International Search Report for International Patent Application No. PCT/US2012/060869, dated Mar. 25, 2013 (5 pages).
Invitation to Pay Additional Fees for International Patent Application No. PCT/CA2011/050807, dated Feb. 13, 2012 (2 pages).
Kalra et al., "The role of C-type natriuretic peptide in cardiovascular medicine," Eur Heart J. 22:997-1007 (2001).
Lo et al., "High level expression and secretion of Fc-X fusion proteins in mammalian cells," Protein Eng. 11(6):495-500 (1998).
Mericq et al., "Regulation of fetal rat bone growth by C-type natriuretic peptide and cGMP," Pediatr Res. 47(2):189-193 (2000) (9 pages).
Miyazawa et al., "Cyclic GMP-dependent protein kinase II plays a critical role in C-type natriuretic peptide-mediated endochondral ossification," Endocrinology. 143(9):3604-3610 (2002).
Nakao et al., "The pharmacokinetics of alpha-human atrial natriuretic polypeptide in healthy subjects," Eur J Clin Pharmacol. 31:101-103 (1986).
NCBI Protein Database Accession No. XP_001109717. Retrieved on Apr. 17, 2013 (1 page).
Pfeifer et al., "Intestinal secretory defects and dwarfism in mice lacking cGMP-dependent protein kinase II," Science. 274:2082-2086 (1996).
Potter et al., "Natriuretic peptides, their receptors, and cyclic guanosine monophosphate-dependent signaling functions," Endocr Rev. 27(1):47-72 (2006).
Shukla et al., "RNA interference and inhibition of MEK-ERK signaling prevent abnormal skeletal phenotypes in a mouse model of craniosynostosis," Nat Genet. 39(9):1145-1150 (2007).
Suda et al., "C-type natriuretic peptide as an autocrine/paracrine regulator of osteoblast: evidence for possible presence of bone natriuretic peptide system," Biochem Biophys Res Commun. 223:1-6 (1996).

(56) References Cited

OTHER PUBLICATIONS

Takano et al., "Molecular evolution of shark C-type natriuretic peptides," Zoolog Sci. 11:451-454 (1994).
Tamura et al., "Critical roles of the guanylyl cyclase B receptor in endochondral ossification and development of female reproductive organs," Proc Natl Acad Sci USA. 101(49):17300-17305 (2004).
Teixeira et al., "Nitric oxide, C-type natriuretic peptide and cGMP as regulators of endochondral ossification," Dev Biol. 319:171-178 (2008).
Tsuji et al., "A loss-of-function mutation in natriuretic peptide receptor 2 (Npr2) gene is responsible for disproportionate dwarfism in cn/cn mouse," J Biol Chem. 280(14):14288-14292 (2005).
Wang et al., "Mice lacking Nf1 in osteochondroprogenitor cells display skeletal dysplasia similar to patients with neurofibromatosis type 1," Hum Mol Genet. 20(20):3910-3924 (2011).
Williams et al., "Solute transport in growth plate cartilage: in vitro and in vivo," Biophys J. 93(3):1039-1050 (2007).
Yasoda et al., "Natriuretic peptide regulation of endochondral ossification. Evidence for possible roles of the C-type natriuretic peptide/guanylyl cyclase-B pathway," J Biol Chem. 273(19):11695-11700 (1998).
Yasoda et al., "Systemic administration of C-type natriuretic peptide as a novel therapeutic strategy for skeletal dysplasias," Endocrinology. 150(7):3138-3144 (2009).
Yoder et al., "Reduced ability of C-type natriuretic peptide (CNP) to activate natriuretic peptide receptor B (NPR-B) causes dwarfism in lbab -/- mice," Peptides. 29(9):1575-1581 (2008).
Farnum et al., "In vivo delivery of fluoresceinated dextrans to the murine growth plate: imaging of three vascular routes by multiphoton microscopy," available in PMC Oct. 28, 2008, published in final edited form as: Anat Rec A Discov Mol Cell Evol Biol. 288(1):91-103 (2006) (22 pages).
Husain et al., "Fc site-specific labeling of immunoglobulins with calf intestinal alkaline phosphatase," Bioconjug Chem. 5(5):482-90 (1994).
Mayer, "Microbiology and immunology on-line: Immunoglobulins: structure and function" <http://pathmicro.med.sc.edu/mayer/IgStruct2000.htm>, University of South Carolina School of Medicine, 12 pages (2009).
Yasoda et al., "Overexpression of CNP in chondrocytes rescues achondroplasia through a MAPK-dependent pathway," Nat Med. 10(1):80-86 (2004).
EBI Blast for Accession No. ATD17216. Entered Oct. 16, 2008 (1 page).
Supplementary European Search Report for European Patent Application No. 11853820.6, dated Mar. 25, 2014 (3 pages).
International Preliminary Report on Patentability for International Patent Application No. PCT/US2012/060869, dated Apr. 22, 2014 (7 pages).
International Preliminary Report on Patentability for International Patent Application No. PCT/US2012/039004, dated Apr. 22, 2014 (8 pages).
Siris et al., "Paget's disease of bone," Trends Endocrinol Metab. 2(6):207-12 (1991).
European Search Report for European Patent Application No. 12842640.0, dated Mar. 13, 2015 (7 pages).
Lee et al., "Disturbed osteoblastic differentiation of fibrous hamartoma cell from congenital pseudarthrosis of the tibia associated with neurofibromatosis type I," Clin Orthop Surg. 3(3):230-7 (2011).
Schindeler et al., "Modeling bone morphogenetic protein and bisphosphonate combination therapy in wild-type and Nf1 haploinsufficient mice," J Orthop Res. 26(1):65-74 (2008).
Nahabet et al., "Postnatal Pancraniosynostosis in a Patient With Infantile Hypophosphatasia," Cleft Palate Craniofac J. 53(6):741-4 (2016).
International Search Report and Written Opinion for International Patent Application No. PCT/US2015/058498, dated Jan. 22, 2016 (12 pages).
Kosnik-Infinger et al., "Enzyme replacement therapy for congenital hypophosphatasia allows for surgical treatment of related complex craniosynostosis: a case series," Neurosurg Focus. 38(5):E10 (2015) (8 pages).
Mornet et al., "Identification of fifteen novel mutations in the tissue-nonspecific alkaline phosphatase (TNSALP) gene in European patients with severe hypophosphatasia," Eur J Hum Genet. 6(4):308-14 (1998).
Alexion Pharma International, "Strensiq Product Monograph," <http://alexionpharma.ca/documents/Strensiq-PM-asfotase-alfa-14Aug2015.aspx>, Prepared Aug. 14, 2015 (32 pages).
Madson et al., "Asfotase alfa: sustained efficacy and tolerability in children with hypophosphatasia treated for 5 years," ESPE Abstracts. 84:FC2.4 (2015) (2 pages).
International Search Report and Written Opinion for International Patent Application No. PCT/US2016/025721, dated Aug. 17, 2016 (18 pages).
Invitation to Pay Additional Fees for International Patent Application No. PCT/US2016/015366, dated Jun. 1, 2016 (7 pages).
Phillips et al., "A modified performance-oriented mobility assessment tool for assessing clinically relevant gait impairments and change in children with hypophosphatasia: development and validation," Bone Abstracts. 4 P136 (2015).
Highlights of Prescribing Information for Strensiq™ Alexion Pharmaceuticals, Inc., available <http://www.alexion.com/Documents/strensiq_pi-10-2015.aspx>, 2015 (19 pages).
Phillips et al., "Gait assessment in children with childhood hypophosphatasia: impairments in muscle strength and physical function," The Endocrine Society's 97th Annual Meeting & Expo, Mar. 5-8, 2015, San Diego, California (2 pages).
"View of NCT02235493 on Nov. 19, 2015," ClinicalTrials.gov archive, Nov. 19, 2015 (4 pages).
Hofmann et al., "Improvement in bone manifestations and respiratory status in infants and young children with HPP treated with asfotase alfa: an update on the ENB-010-10 trial," 7th International Conference on Children's Bone Health, Jun. 27-30, Austria, Salzburg. Bone Abstracts. 4: OC18 (2015) (3 pages).
Epps, "Application No. 125513Orig1s000 Medical Review(s)," Center for Drug Evaluation and Research, <http://www.accessdata.fda.gov/drugsatfda_docs/nda/2015/125513Orig1s000MedR.pdf>, Oct. 20, 2015 (254 pages).
International Search Report and Written Opinion for International Patent Application No. PCT/US2016/039595, dated Feb. 21, 2017 (16 pages).
Liu et al., "Tissue-nonspecific alkaline phosphatase deficiency causes abnormal craniofacial bone development in the Alpl(-/-) mouse model of infantile hypophosphatasia," available in PMC Oct. 1, 2015, published in final edited form as: Bone. 67:81-94 (2014) (30 pages).
Appeal Brief as Filed in U.S. Appl. No. 12/638,527, mailed Oct. 9, 2015 (101 pages).
Reply Brief as Filed in U.S. Appl. No. 12/638,527, mailed Apr. 22, 2016 (4 pages).
Examiner's Answer to Appeal Brief for U.S. Appl. No. 12/638,527, mailed Feb. 23, 2016 (9 pages).
Phillips et al., "Significantly improved muscle strength, running speed, and agility in children with hypophosphatasia treated with asfotase alfa," Endocrine Society's 97th Annual Meeting and Expo, Mar. 5-8, San Diego, CA. Abstract OR29-4 (2015) (2 pages).
Millán et al., "Alkaline phosphatase and hypophosphatasia," Calcif Tissue Int. 98(4):398-416 (2016).
Kishnani et al., "Biochemical and physical function outcomes in adolescents and adults with hypophosphatasia treated with asfotase alfa for up to 4 years: interim results from a phase II study," Endocrine Society's 98th Annual Meeting and Expo, Apr. 1-4, Boston, MA. Abstract OR26-3 (2016) (2 pages).
International Search Report and Written Opinion for International Patent Application No. PCT/US2017/025590, dated Jun. 29, 2017 (18 pages).
Iqbal et al., "Recurrent Metatarsal Fractures in Postmenopausal Woman With Low Serum Alkaline Phosphatase: A Rare Diagnosis Not to Miss," J Investig Med High Impact Case Rep. 5(3):1-3 (2017).

(56) References Cited

OTHER PUBLICATIONS

Ahn et al., "Idiopathic calcium pyrophosphate dihydrate (CPPD) crystal deposition disease in a young male patient: a case report," J Korean Med Sci. 18(6):917-20 (2003).
Cahill et al., "Infantile hypophosphatasia: transplantation therapy trial using bone fragments and cultured osteoblasts," J. Clin Endocrinol Metab. 92(8): 2923-30 (2007).
Glass et al., "The infant skull: a vault of information," Radiographics. 24(2):507-22 (2004).
Herasse et al., "Molecular study of three cases of odontohypophosphatasia resulting from heterozygosity for mutations in the tissue non-specific alkaline phosphatase gene," J Med Genet. 40(8):605-9 (2003).
Ishida et al., "Tissue-nonspecific alkaline phosphatase with an Asp(289)→Val mutation fails to reach the cell surface and undergoes proteasome-mediated degradation," J Biochem. 134(1):63-70 (2003).
Mornet, "Hypophosphatasia," Orphanet J Rare Dis. 2:(40) (2007) (8 pages).
Spentchian et al., "Severe hypophosphatasia: characterization of fifteen novel mutations in the ALPL gene," Hum Mutat. 22(1) (2003) (5 pages).
Takinami et al., "The mutant (F310L and V365I) tissue-nonspecific alkaline phosphatase gene from hypophosphatasia," J Med Dent Sci. 51(1):67-74 (2004).
Sawai et al., "Severe perinatal hypophosphatasia due to homozygous deletion of T at nucleotide 1559 in the tissue nonspecific alkaline phosphatase gene,". Prenat Diagn. 23(9):743-6 (2003).
Wickramasinghe et al., "A case of hypophosphatasia," Ceylon Med J. 48(3):94-5 (2003).
Yamamoto et al., "A successful treatment with pyridoxal phosphate for West syndrome in hypophosphatasia," Pediatr Neurol. 30(3):216-8 (2004).
International Preliminary Report on Patentability for International Patent Application No. PCT/US2016/015366, dated Aug. 10, 2017 (10 pages).
International Search Report and Written Opinion for International Patent Application No. PCT/US2017/047527, dated Nov. 6, 2017 (10 pages).
Millán et al., "Hypophosphatasia—pathophysiology and treatment," available in PMC Sep. 22, 2014, published in final edited form as: Actual Osteol. 8(3):164-182 (2012) (21 pages).
Padidela et al., "P1-118: Management of Tracheobronchomalacia During Asfotase Alfa Treatment in Infants with Perinatal-Onset Hypophosphatasia: A Case Series," European Society for Paediatric Endocrinology (ESPE), Paris, France, Sep. 10-12, 2016 (1 page).
Mornet et al., "Structural evidence for a functional role of human tissue nonspecific alkaline phosphatase in bone mineralization," J Biol Chem. 276(33):31171-8 (2001).
Bhattacharyya et al., "Hypophosphatasia and the risk of atypical femur fractures: a case-control study," BMC Muscoloskelet Disord. 17:332 (2016) (4 pages).
Bishop, "Asfotase alfa for hypophosphatasia," Horizon Scanning Centre. National Institute for Health Research. http://www.hsric.nihr.ac.uk/topics/asfotase-alfa-for-hypophosphatasia/download, retrieved Oct. 20, 2013 (9 pages).
Bishop et al., "Transformative therapy in hypophosphatasia," Arch Dis Child. 101(6):514-5 (2016).
Bishop, "Clinical management of hypophosphatasia," Clin Cases Miner Bone Metab. 12(2):170-3 (2015).
Durussel et al., "Bone mineralization-dependent craniosynostosis and craniofacial shape abnormalities in the mouse model of infantile hypophosphatasia," Dev Dyn. 245(2):175-82 (2016).
Braunstein, "Multiple fractures, pain, and severe disability in a patient with adult-onset hypophosphatasia," Bone Rep. 4:1-4 (2015).
Bloch-Zupan, "Hypophosphatasia: diagnosis and clinical signs—a dental surgeon perspective," Int J Paediatr Dent. 26(6):426-438 (2016).
Kishnani et al., "Monitoring guidance for patients with hypophosphatasia treated with asfotase alfa," Mol Genet Metab. 122(1-2):4-17 (2017).
Güzel et al., "Pyridoxine-responsive seizures in infantile hypophosphatasia and a novel homozygous mutation in ALPL gene," J Clin Res Pediatr Endocrinol. 8(3):360-4 (2016).
Gasque et al., "Improvement of the skeletal and dental hypophosphatasia phenotype in Alpl -/- mice by administration of soluble (non-targeted) chimeric alkaline phosphatase," Available in PMC Mar. 1, 2016, published in final edited form as: Bone. 72:137-147 (2015) (25 pages).
Fodor et al., "Differencial diagnosis of the low alkaline phosphatase activities," Orv Hetil. 158(26): 1003-1007 (2017) (Article in Hungarian) (English Abstract included).
McKiernan et al., "Clinical and radiographic findings in adults with persistent hypophosphatasemia," J Bone Miner Res. 29(7):1651-60 (2014).
Martos-Moreno et al., "Hypophosphatasia: clinical manifestations, diagnostic recommendations and therapeutic options," An Pediatr (Barc). S1695-4033(17)30223-0 (2017) (11 pages) (Article in Spanish) (English Abstract included).
Kulikova et al., "Hypophosphatasia: the clinical description of 3 cases of the disease with the molecular-genetic verification of the diagnosis," Problems of Endocrinology. 61(3):37-42 (2015) (Article in Russian) (English Abstract included).
Orimo, "Pathophysiology of hypophosphatasia and the potential role of asfotase alfa," Ther Clin Risk Manag. 12:777-86 (2016).
Morrow, "Expensive new biologic helps children fight hypophosphatasia," Manag Care. 24(12) (2015) (7 pages).
Mornet et al., "Hypophosphatasia," GeneReviews. https://www.ncbi.nlm.nih.gov/books/NBK1150/, retrieved Dec. 6, 2017, initially published Nov. 20, 2007, last updated Feb. 4, 2016 (25 pages).
Mori et al., "Case series: odontohypophosphatasia or missed diagnosis of childhood/adult-onset hypophosphatasia?—Call for a long-term follow-up of premature loss of primary teeth," Bone Rep. 5:228-232 (2016).
Remde et al., "Successful asfotase alfa treatment in an adult dialysis patient with childhood-onset hypophosphatasia," J Endoc Soc. 1(9):1188-93 (2017).
Panesar, "Hypophosphatasia: a rare disorder," US Pharm. 42(5) (2017) (8 pages).
Padidela et al., "Enzyme-replacement therapy in life-threatening perinatal hypophosphatasia in a premature infant," Endocrine Abstracts. 33:P9 (2013) (1 page).
Sotillo et al., "Signs and symptoms of hypophosphatasia," Dimensions of Dental Hygiene. 15(4):44-47 (2017) (6 pages).
Simm et al., "Successful use of enzyme replacement therapy in infantile hypophosphatasia," J Paediatr Child Health. 53(9):925-926 (2017).
Sheikh et al., "A newborn with no bones: neonatal hypophosphatasia with respiratory distress," J Pediatr. 188:306 (2017).
Saglam et al., "Clinical and genetic findings of Turkish hypophosphatasia cases," J Clin Res Pediatr Endocrinol. 9(3):229-236 (2017).
Whyte et al., "Asfotase alfa treatment improves survival for perinatal and infantile hypophosphatasia," J Clin Endocrinol Metab. 101(1):334-42 (2016) (17 pages).
Wang et al., "Current concepts in odontohypophosphatasia form of hypophosphatasia and report of two cases," BMC Oral Health. 16(1):70 (2016) (8 pages).
Taketani et al., "Ex vivo expanded allogeneic mesenchymal stem cells with bone marrow transplantation improved osteogenesis in infants with severe hypophosphatasia," Cell Transplant. 24(10):1931-43 (2015).
Belachew et al., "Infantile hypophosphatasia secondary to a novel compound heterozygous mutation presenting with pyridoxine-responsive seizures," JIMD Rep. 11:17-24 (2013).
Whyte et al., "Asfotase alfa therapy for children with hypophosphatasia," JCI Insight. 1(9):e85971 (2016) (11 pages).
Whyte, "Hypophosphatasia: enzyme replacement therapy brings new opportunities and new challenges," J Bone Miner Res. 32(4):667-675 (2017).
Alexion Third Quarter 2017 Earnings Call, "http://files.shareholder.com/downloads/ALXN/5636824573x0x961197/3B361D6E-80E2-463E-B0E5-3EAD7FC5B9DO/Alexion_Q3_2017_Earnings_Slides.pdf" (43 pages).

(56) References Cited

OTHER PUBLICATIONS

Urlaub et al., "Isolation of Chinese hamster cell mutants deficient in dihydrofolate reductase activity," Proc Natl Acad Sci U S A. 77(7):4216-20 (1980).
Graham et al., "Characteristics of a human cell line transformed by DNA from human adenovirus type 5," J Gen Virol. 36(1):59-72 (1977).
Mather, "Establishment and characterization of two distinct mouse testicular epithelial cell lines," Biol Reprod. 23(1):243-52 (1980).
Le Du et al., "Crystal structure of alkaline phosphatase from human placenta at 1.8 A resolution. Implication for a substrate specificity," J Biol Chem. 276(12):9158-65 (2001) (9 pages).
Stec et al., "A revised mechanism for the alkaline phosphatase reaction involving three metal ions," J Mol Biol. 299(5):1303-11 (2000).
Alexion, "Highlights of Prescribing Information" for Strensiq®, 2018 (8 pages).
European Collection of Authenticated Cell Cultures (ECACC) Accession No. 85110503. Retrieved May 2, 2018 (3 pages).
UniProtKB Accession No. P05186. Retrieved May 2, 2018 (19 pages).
UniProtKB Accession No. P01857. Retrieved May 2, 2018 (13 pages).
Belkhouribchia et al., "Case Report: Osteomalacia with low alkaline phosphatase: a not so rare condition with important consequences," BMJ Case Rep. doi: 10.1136/bcr-2015-212827 (2016) (4 pages).
Berkseth et al., "Clinical spectrum of hypophosphatasia diagnosed in adults," Bone. 54(1):21-7 (2013).
Bianchi, "Hypophosphatasia: an overview of the disease and its treatment," Osteoporos Int. 26(12):2743-57; DOI 10.1007/s00198-015-3272-1 (2015) (15 pages).
Bobryshev et al., "Role of bone-type tissue-nonspecific alkaline phosphatase and PHOSPO1 in vascular calcification," Curr Pharm Des. 20(37):5821-8 (2014).
Bowden et al., "Asfotase alfa treatment for 1 year in a 16 year-old male with severe childhood hypophosphatasia," Osteoporos Int. 29(2):511-5; DOI: 10.1007/s00198-017-4267-x (2018) (5 pages).
Briot et al., "Adult hypophosphatasia," Curr Opin Rheumatol. 28(4):448-51 (2016).
Buchet et al., "Multisystemic functions of alkaline phosphatases," Methods Mol Biol. 1053:27-51 (2013).
Deeb et al., "Could alerting physicians for low alkaline phosphatase levels be helpful in early diagnosis of hypophosphatasia?," J Clin Res Pediatr Endocrinol. 10(1):19-24 (2018).
Hofmann et al., "Recombinant enzyme replacement therapy in hypophosphatasia," Subcell Biochem. 76:323-41 (2015).
Hofmann et al., "Asfotase alfa: enzyme replacement for the treatment of bone disease in hypophosphatasia," Drugs Today (Barc). 52(5):271-85 (2016).
Kitaoka et al., "Safety and efficacy of treatment with asfotase alfa in patients with hypophosphatasia: results from a Japanese clinical trial," Clin Endocrinol (Oxf). 87(1):10-19 (epub pp. 1-10) (2017).
Linglart et al., "Hypophosphatasia," Curr Osteoporos Rep. 14(3):95-105; DOI 10.1007/s11914-016-0309-0 (2016) (11 pages).
Mornet, "Hypophosphatasia," Metabolism. 82:142-155; DOI: 10.1016/j.metabol.2017.08.013 (2018) (30 pages).
Mornet, "Molecular genetics of hypophosphatasia and phenotype-genotype correlations," Subcell Biochem. 76:25-43 (2015).
Okazaki et al., "Lethal hypophosphatasia successfully treated with enzyme replacement from day 1 after birth," Eur J Pediatr. 175(3):433-7; DOI 10.1007/s00431-015-2641-2 (2016) (5 pages).
Park et al., "First Korean case of infantile hypophosphatasia with novel mutation in ALPL and literature review," Ann Clin Lab Sci. 46(3):302-7 (2016).
Phillips et al., "Physical therapy management of infants and children with hypophosphatasia," Mol Genet Metab. 119(1-2):14-9 (2016).
Rockman-Greenberg, "Hypophosphatasia," Pediatr Endocrinol Rev. 10 Suppl 2:380-8 (2013) (Abstract only).
Rodriguez et al., "Respiratory mechanics in an infant with perinatal lethal hypophosphatasia treated with human recombinant enzyme replacement therapy," Pediatr Pulmonol. 47(9):917-22 (2012).
Saraff et al., "A diagnostic algorithm for children with low alkaline phosphatase activities: lessons learned from laboratory screening for hypophosphatasia," J Pediatr. 172:181-6 (2016) (7 pages).
Sather, "008-case study: 3 year old female with hypophosphatasia, treated with asfotase alfa replacement," Journal of Pediatric Nursing. 34:104 (2017).
Schmidt et al., "Hypophosphatasia: What is currently available for treatment?" Internist (Berl). 57(12):1145-1154 (2016) (Article in German) (English abstract).
Schmidt et al., "Clinical, radiographic and biochemical characteristics of adult hypophosphatasia," Osteoporos Int. 28(9):2653-2662 (2017).
Scott, "Asfotase alfa in perinatal/infantile-onset and juvenile-onset hypophosphatasia: a guide to its use in the USA," BioDrugs. 30(1):41-8 (2016).
Scott, "Asfotase alfa: a review in paediatric-onset hypophosphatasia," Drugs. 76(2):255-62 (2016).
Shapiro et al., "Hypophosphatasia in adults: clinical assessment and treatment considerations," J Bone Miner Res. 32(10):1977-1980 (2017).
Siller et al., "Alkaline phosphatase: discovery and naming of our favorite enzyme," J Bone Miner Res. 33(2):362-4 (2018).
Takahashi et al., "Parental serum alkaline phosphatase activity as an auxiliary tool for prenatal diagnosis of hypophosphatasia," Prenat Diagn. 37(5):491-6 (2017).
Tenorio et al., "Molecular and clinical analysis of ALPL in a cohort of patients with suspicion of hypophosphatasia," Am J Med Genet A. 173(3):601-10 (2017).
Tsiantouli et al., "Hypophosphatasia," Rev Med Suisse. 13(559):855-8 (2017) (Article in French) (English Abstract Included).
Weber et al., "Burden of disease in adult patients with hypophosphatasia: Results from two patient-reported surveys," Metabolism. 65(10):1522-30 (2016).
Whyte, "Hypophosphatasia—aetiology, nosology, pathogenesis, diagnosis and treatment," Nat Rev Endocrinol. 12(4):233-46 (2016).
Whyte, "Hypophosphatasia: an overview for 2017," Bone. 102:15-25 (2017).
Whyte et al., "Hypophosphatasia: natural history study of 101 affected children investigated at one research center," Bone. 93:125-138 (2016).
Whyte et al., "Hypophosphatasia: validation and expansion of the clinical nosology for children from 25 years experience with 173 pediatric patients," Bone. 75:229-39 (2015).
International Search Report and Written Opinion for International Patent Application No. PCT/US2016/054013, dated Dec. 13, 2016 (19 pages).
Seefried et al., "Pharmacodynamic results from a phase 2a, randomized, multicenter, open-label, dose-ranging study of asfotase alfa in adults with pediatric hypophosphatasia," 100th Annual Meeting and Expo of the Endocrine Society, Mar. 17-20, 2018, Chicago, IL. (1 page).
International Search Report and Written Opinion for International Patent Application No. PCT/US2018/020859, dated Jun. 19, 2018 (14 pages).
López-Delgado et al., "Abnormal bone turnover in individuals with low serum alkaline phosphatase," Osteoporosis Int. 29(9):2147-2150; doi: 10.1007/s00198-018-4571-0 (Supplementary information included) (2018) (6 pages).
Lazdunski et al., "Structure-function relationships for some metalloalkaline phosphatases of E. coli," Eur J Biochem. 8(4):510-7 (1969).
Bobyr et al., "High-resolution analysis of Zn(2+) coordination in the alkaline phosphatase superfamily by EXAFS and x-ray crystallography," J Mol Biol. 415(1):102-17 (2012).
International Search Report and Written Opinion for International Patent Application No. PCT/US2017/036133, dated Aug. 24, 2017 (10 pages).
International Search Report and Written Opinion for International Patent Application No. PCT/US2018/025206, dated Jul. 3, 2018 (25 pages).

(56) References Cited

OTHER PUBLICATIONS

Kishnani et al., "OR26-3 Biochemical and Physical Function Outcomes in Adolescents and Adults with Hypophosphatasia Treated with Asfotase Alfa for up to 4 Years: Interim Results from a Phase II Study," ENDO 2016, Boston, MA, Apr. 3, 2016 (22 pages).
International Search Report and Written Opinion for International Patent Application No. PCT/US2017/025618, dated Jul. 11, 2017 (22 pages).
Li et al., "Standard reference for the six-minute-walk test in healthy children aged 7 to 16 years," Am J Respir Crit Care Med. 176(2):174-80 (2007).
Park et al., "Ex vivo assessment of contractility, fatigability and alternans in isolated skeletal muscles," J Vis Exp. 69:e4198 (2012) (8 pages).
Phillips et al., "FRI-224: Improved activities of daily living and physical function, with decreased pain, in children with hypophosphatasia treated for three years with asfotase alfa: results from the childhood health assessment questionnaire and the pediatric outcomes data collection instrument," The Endocrine Society's 97th Annual Meeting & Expo, San Diego, California, Mar. 5-8, 2015 (1 page).
Whyte et al., "Hypophosphatasia: Enzyme replacement therapy (asfotase alfa) decreases TNSALP substrate accumulation and improves functional outcomes in affected adolescents and adults," Bull Group Int Rech Sci Stomatol Odontol. 51(1):35 (2012).
Sugano et al., "Successful gene therapy in utero for lethal murine hypophosphatasia," Hum Gene Ther. 23(4):399-406 (2012).
International Search Report and Written Opinion for International Patent Application No. PCT/US2015/039973, dated Oct. 5, 2015 (12 pages).
Johnson et al., "Motor proficiency in children with neurofibromatosis type 1," Pediatr Phys Ther. 22(4):344-8 (2010).
Gates et al., "Effects of age, sex, and comorbidities on the pediatric outcomes data collection instrument (PODCI) in the general population," J Pediatr Orthop. 35(2):203-9 (2015).
International Search Report and Written Opinion for International Patent Application No. PCT/US2016/049983, dated Nov. 29, 2016 (12 pages).
International Search Report and Written Opinion for International Patent Application No. PCT/US2016/015366, dated Aug. 9, 2016 (14 pages).
Extended European Search Report for European Application No. 18173111.8, dated Aug. 21, 2018 (9 pages).
National Institute for Health and Care Excellence, "Highly Specialised Technology Evaluation: Asfotase alfa for treating paediatric-onset hypophosphatasia [ID 758]," Oct. 21, 2015, <https://www.nice.org.uk/guidance/hst6/documents/committee-papers-8> (99 pages).
Tomazos et al., "Determination of the Minimal Clinically Important Difference in the Six-Minute Walk Test for Patients with Hypophosphatasia," 55th Annual European Society for Paediatric Endocrinology Meeting, Sep. 10-12, Paris, France. 86, Abstract FC2.5, <http://abstracts.eurospe.org/hrp/0086/hrp0086FC2.5.htm> (2016) (4 pages).
International Search Report and Written Opinion for International Application No. PCT/US18/26868, dated Sep. 7, 2018 (30 pages).
International Preliminary Report on Patentability for International Patent Application No. PCT/US2016/049983, dated Sep. 11, 2018 (9 pages).
Sequence 4, U.S. Appl. No. 12/599,679, Retrieved Nov. 17, 2018 (2 pages).
Agochukwu et al., "Hearing loss in syndromic craniosynostoses: introduction and consideration of mechanisms," available in PMC Aug. 13, 2014, published in final edited form as: Am J Audiol. 23(2): 135-41 (2014) (13 pages).
Balasubramaniam et al., "Perinatal hypophosphatasia presenting as neonatal epileptic encephalopathy with abnormal neurotransmitter metabolism secondary to reduced co-factor pyridoxal-5'-phosphate availability," J Inherit Metab Dis. 33(Suppl 3):S25-33 (2010).

Barcia et al., "Infantile hypophosphatasia: treatment options to control hypercalcemia, hypercalciuria, and chronic bone demineralization," J Pediatr. 130(5):825-8 (1997).
Barvencik et al., "Skeletal mineralization defects in adult hypophosphatasia—a clinical and histological analysis," Osteoporosis Int. 22(10):2667-75 (2011).
Baumgartner-Sigl et al., "Pyridoxine-responsive seizures as the first symptom of infantile hypophosphatasia caused by two novel missense mutations (c.677T>C, p.M226T; c.1112C>T, p.T371I) of the tissue-nonspecific alkaline phosphatase gene," Bone. 40(6):1655-61 (2007).
Beck et al., "Whole-body MRI in the childhood form of hypophosphatasia," Rheumatol Int. 31(10):1315-20 (2011).
Beederman et al., "Molecular basis of cranial suture biology and disease: osteoblastic and osteoclastic perspectives," Genes Dis. 1(1):120-5 (2014).
Boulet et al., "A population-based study of craniosynostosis in metropolitan Atlanta, 1989-2003," Am J Med Genet A. 146A(8): 984-91 (2008).
Chan et al., "Endoscope-assisted versus open repair of craniosynostosis: a comparison of perioperative cost and risk," J Craniofac Surg. 24(1): 170-4 (2013).
Choi et al., "Craniosynostosis in growing children: pathophysiological changes and neurosurgical problems," J Korean Neurosurg Soc. 59(3):197-203 (2016).
Chong et al., "Minimally invasive suturectomy and postoperative helmet therapy: advantages and limitations," J Korean Neurosurg Soc. 59(3):227-32 (2016).
Clarke, "Normal bone anatomy and physiology," Clin J Am Soc Nephrol. 3 Suppl 3: S131-9 (2008).
Colantonio et al., "Closing the gaps in pediatric laboratory reference intervals: a CALIPER database of 40 biochemical markers in a healthy and multiethnic population of children," Clin Chem. 58(5):854-68 (2012).
Collmann et al., "Neurosurgical aspects of childhood hypophosphatasia," Childs Nerv Syst. 25(2):217-23 (2009).
Czerwinski et al., "Major morbidity and mortality rates in craniofacial surgery: an analysis of 8101 major procedures," Plast Reconstr Surg. 126(1):181-6 (2010).
Eade et al., "Pyrophosphate arthropathy in hypophosphatasia," Ann Rheum Dis. 40(2):164-70 (1981).
Esparza et al., "Complications in the surgical treatment of craniosynostosis and craniofacial syndromes: apropos of 306 transcranial procedures," Childs Nerv Syst. 24(12):1421-30 (2008).
Esparza et al., "Surgical treatment of isolated and syndromic craniosynostosis. Results and complications in 283 consecutive cases," Neurocirugia. 19(6):509-29 (2008).
Fraser, "Hypophosphatasia," Am J Med. 22(5):730-46 (1957).
Garber et al., "Comparing outcomes and cost of 3 surgical treatments for sagittal synostosis: a retrospective study including procedure-related cost analysis," Neurosurgery. 81(4):680-7 (2017).
Ginelliová et al., "Sudden death associated with syndromic craniosynostosis," Forensic Sci Med Pathol. 12(4):506-9 (2016).
Greenwood et al., "Familial incidence and associated symptoms in a population of individuals with nonsyndromic craniosynostosis," Genet Med. 16(4):302-10 (2014).
Guañabens et al., "Calcific periarthritis as the only clinical manifestation of hypophosphatasia in middle-aged sisters," J Bone Miner Res. 29(4):929-34 (2014).
Herring, "Mechanical influences on suture development and patency," Front Oral Biol. 12:41-56 (2008).
Hollis et al., "Current concepts in hypophosphatasia: case report and literature review," Int J Paediatr Dent. 23(3):153-159 (2013).
Hwang et al., "Update of diagnostic evaluation of craniosynostosis with a focus on pediatric systematic evaluation and genetic studies," J Korean Neurosurg Soc. 59(3):214-8 (2016).
Johnson et al., "Craniosynostosis," Eur J Hum Genet. 19(4):369-76 (2011).
Kabbani et al., "Craniosynostosis," Am Fam Physician. 69(12):2863-70 (2004).
Katsianou et al., "Signaling mechanisms implicated in cranial sutures pathophysiology: craniosynostosis," BBA Clin. 6:165-76 (2016).

(56) References Cited

OTHER PUBLICATIONS

Khanna et al., "Pictorial essay: The many faces of craniosynostosis," retrieved from <www.ncbi.nlm.nih.gov/pmc/articles/PMC3056371/> on Sep. 10, 2017, Indian J Radiol Imaging. 21(1):49-56 (2011) (8 pages).
Kim et al., "Craniosynostosis: Updates in radiologic diagnosis," J Korean Neurosurg Soc. 59(3):219-26 (2016).
Kozlowski et al., "Hypophosphatasia. Review of 24 Cases," Pediatr Radiol. 5(2):103-17 (1976).
Krakow et al., "Clinical and radiographic delineation of Bent Bone Dysplasia-FGFR2 type or Bent Bone Dysplasia with Distinctive Clavicles and Angel-shaped Phalanges," Am J Med Genet A. 170(10):2652-61 (2016).
Mathijssen, "Guideline for care of patients with the diagnoses of craniosynostosis: working group on craniosynostosis," J Craniofac Surg. 26(6):1735-807 (2015).
Merrill et al., "Bent bone dysplasia-FGFR2 type, a distinct skeletal disorder, has deficient canonical FGF signaling," Am J Hum Genet. 90(3):550-7 (2012).
Millán, "The role of phosphatases in the initiation of skeletal mineralization," Calcif Tissue Int. 93(4):299-306 (2013).
Miller et al., "Ultrasound diagnosis of craniosynostosis," Cleft Palate Craniofac J. 39(1):73-80 (2002).
Millichap, "Cognitive Development of Children with Craniosynostosis," Pediatr Neurol Briefs. 29(6):47 (2015).
Mohn et al., "Hypophosphatasia in a child with widened anterior fontanelle: lessons learned from late diagnosis and incorrect treatment," Acta Paediatr. 100(7):e43-6 (2011).
Mornet et al., "A molecular-based estimation of the prevalence of hypophosphatasia in the European population," Ann Hum Genet. 75(3):439-45 (2011).
Nakamura-Utsunomiya et al., "Clinical characteristics of perinatal lethal hypophosphatasia: a report of 6 cases," Clin Pediatr Endocrinol. 19(1):7-13 (2010).
Oginni et al., "Radiological and biochemical resolution of nutritional rickets with calcium," Arch Dis Child. 88(9):812-17 (2003).
Opperman, "Cranial sutures as intramembranous bone growth sites," Dev Dyn. 219(4):472-85 (2000).
Reginato et al., "Musculoskeletal manifestations of osteomalacia and rickets," Best Pract Res Clin Rheumatol. 17(6):1063-80 (2003).
Rodgers et al., "Spring assisted cranioplasty for the correction of non-syndromic scaphocephaly: a quantitative analysis of 100 consecutive cases," Plast Reconstr Surg. 140(1):125-34 (2017).
Rottgers et al., "Outcomes of endoscopic suturectomy with postoperative helmet therapy in bilateral coronal craniosynostosis," J Neurosurg Pediatr. 18(3):281-6 (2016).
Rozovsky et al., "Cranial ultrasound as a first-line imaging examination for craniosynostosis," Pediatrics. 137(2):e20152230 (2016) (9 pages).
Sabbagh et al., "Hypophosphatemia leads to rickets by impairing caspase-mediated apoptosis of hypertrophic chondrocytes," Proc Natl Acad Sci U S A. 102(27):9637-42 (2005).
Sakamoto et al., "Physiological changes and clinical implications of syndromic craniosynostosis," J Korean Neurosurg Soc. 59(3):204-13 (2016).
Salva et al., "Signaling networks in joint development," Dev Dyn. 246(4):262-74 (2017).
Seshia et al., "Myopathy with hypophosphatasia," Arch Dis Child. 65(1):130-1 (1990).
Shah et al., "Sudden infant death in a patient with FGFR3 P250R mutation," Am J Med Genet A. 140A(24):2794-6 (2006).
Sharma et al., "Bilateral femoral neck fractures in a young patient suffering from hypophosphatasia, due to a first time epileptic seizure," J Orthop Case Rep. 5(3):66-8 (2015).
Sharma, "Craniosynostosis," Indian J Plast Surg. 46(1):18-27 (2013).
Silver et al., "Pulmonary hypoplasia in neonatal hypophosphatasia," Pediatr Pathol. 8(5):483-93 (1988) (12 pages).
Thacher et al., "Radiographic scoring method for the assessment of the severity of nutritional rickets," J Trop Pediatr. 46(3):132-9 (2000).
Thurner et al., "Osteopontin deficiency increases bone fragility but preserves bone mass," Bone. 46(6):1564-73 (2010).
Tokumaru et al., "Skull base and calvarial deformities: association with intracranial changes in craniofacial syndromes," Am J Neuroradiol. 17(4):619-30 (1996).
Watanabe et al., "Prevalence of c.1559delT in ALPL, a common mutation resulting in the perinatal (lethal) form of hypophosphatasia in Japanese and effects of the mutation on heterozygous carriers," J Hum Genet. 56(2):166-8 (2011).
Whyte et al., "Adult hypophosphatasia with chondrocalcinosis and arthropathy: variable penetrance of hypophosphatasemia in a large Oklahoma kindred," Am J Med. 72(4):631-41 (1982).
Whyte et al., "Adult hypophosphatasia treated with teriparatide," J Clin Endocrinol Metab. 92(4):1203-8 (2007).
Whyte et al., "Rickets and osteomalacia," Medicine. 37(9):483-8 (2009).
Zaleckas et al., "Diagnosis and treatment of craniosynostosis: Vilnius team experience," Acta Med Litu. 22(2):111-21 (2015).
Anderson, "Mechanism of Mineral Formation in Bone," *Pathology Reviews*. Emanuel Rubin and Ivan Damjanov (eds.), 13-23 (1990).
Whyte, Chapter 73: Hypophosphatasia: Nature's Window on Alkaline Phosphatase Function in Humans, *Principles of Bone Biology*, vol. 1, Third Edition. John P. Bilezikian, Lawrence G. Raisz and T. John Martin (eds.), 1573-98 (2008).
Whyte, Chapter 22: Hypophosphatasia, *Genetics of Bone Biology and Skeletal Disease*. Rajesh V. Thakker, Michael P. Whyte, John A. Eisman and Takashi Igarashi (eds.), 337-360 (2013).
Del Angel et al., "Birth prevalence estimation of severe Hypophosphatasia in European populations using large-scale protein-coding genetic variation databases," American Society of Human Genetics 66th Annual Meeting, Oct. 18-22, Vancouver, Canada. Poster abstract 1670T (2016) (2 pages).
Rockman-Greenberg et al., "Hypophosphatasia: Enzyme Replacement with ENB-0040, a Bone-Targeted Human Recombinant Tissue Nonspecific Alkaline Phosphatase (TNSALP) Fusion Protein," American College of Medical Genetics, 16th Annual Clinical Genetics Meeting, Mar. 25-29, Tampa, Florida (2009) (1 page).
Simmons, "Best Practices in: Recognizing and Diagnosing Hypophosphatasia," Clinical Endocrinology News. <https://www.mdedge.com/sites/default/files/issues/articles/Alexion_10_11_Final_Web.pdf>, published Sep. 30, 2013, retrieved on Mar. 27, 2019 (8 pages).
Weber et al., "Burden of disease in children with hypophosphatasia: results from patient-reported surveys," 7th International Conference on Children's Bone Health, Jun. 27-30, Salzburg, Austria. *Bone Abstracts*. 4: P119 (2015) (3 pages).
Whyte et al., "Asfotase alfa: Sustained Efficacy and Tolerability in Infants and Young Children with Life-Threatening Hypophosphatasia," 2014 Pediatric Academic Societies and Asian Society for Pediatric Research Joint Meeting, May 3-6, Vancouver, BC, Canada. Poster 69 (2014) (1 page).
Whyte et al., "Hypophosphatasia: a Retrospective Natural History Study of the Severe Perinatal and Infantile Forms," 2014 European Calcified Tissue Society Congress, May 17-20, Prague, Czech Republic. Poster P364 (2014) (1 page).
Whyte et al., "A retrospective, multi-national, non-interventional, natural history study of the childhood form of hypophosphatasia," ENDO 2015: The Endocrine Society Annual Meeting, Mar. 5-8, San Diego, California. Abstract LB-OR01-4 (2015) (2 pages).
Stoll et al., "Severe hypophosphatasia due to mutations in the tissue-nonspecific alkaline phosphatase (TNSALP) gene," Genet Couns. 13(3):289-95 (2002).
Mornet, "Hypophosphatasia," Best Pract Res Clin Rheumatol. 22(1):113-27 (2008).
Kajdic et al., "Craniosynostosis—Recognition, clinical characteristics, and treatment," Bosn J Basic Med Sci. 18(2):110-6 (2018).
Communication pursuant to Rule 164(2)(b) and Article 94(3) EPC for European Application No. 16707571.2, dated Feb. 26, 2019 (12 pages).
Fong et al., "Hypocalcemia: Updates in diagnosis and management for primary care," Can Fam Physician. 58(2):158-62 (2012).
Makras et al., "Medical treatment of Hypercalcaemia," Hormones. 8(2):83-95 (2009).

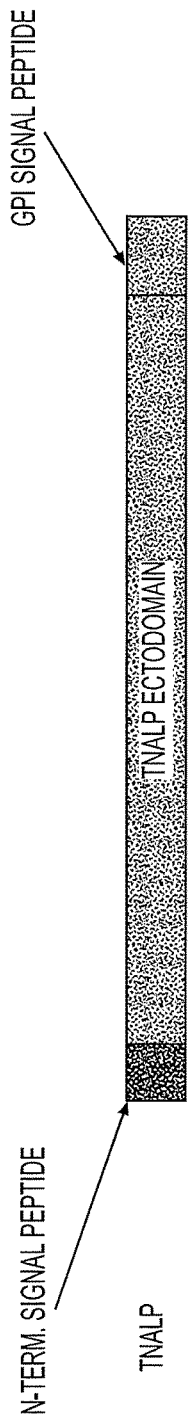

MISPFLVLAIGTCLTNSLVPEKEKDPKYWRDQAQETLKYALELQKLNTNVAKNVIMFLGDGMGVS
TVTAARILKGQLHHNPGEETRLEMDKFPFVALSKTYNTNAQVPDSAGTATAYLCGVKANEGTVGV
SAATERSRCnTTQGNEVTSILRWAKDAGKSVGIVTTRVNHATPSAAYAHSADRDWYSDNEMPP
EALSQGCKDIAYQLMHNIRDIDVIMGGGRKYMYPKnKTDVEYESDEKARGTRLDGLDLVDTWKS
FKPRYKHSHFIWNnRTELLTLDPHNVDYLLGLFEPGDMQYELNRRNnVTDPSLSEMVVAIQILRKNP
KGFFLLVEGGRIDHGHHEGKAKQALHEAVEMDRAIGQAGSLTSSEDTLTVTADHSHVFTFGGYT
PRGNSIFGLAPMLSDTDKKPFTAILYGNGPGYKVVGGEREnVSMVDYAHNNYQAQSAVPLRHET
HGGEDVAVFSKGPMAHLLHGVHEQNYVPHVMAYAACIGANLGHCAPASSLKDKTHTCPPCPAP
ELLGGPSVFLFPPKPKDTLMISRTPEVTCVVVDVSHEDPEVKFNWYVDGVEVHNAKTKPREEQYn
STYRVVSVLTVLHQDWLNGKEYKCKVSNKALPAPIEKTISKAKGQPREPQVYTLPPSREEMTKNQ
VSLTCLVKGFYPSDIAVEWESNGQPENNYKTTPPVLDSDGSFFLYSKLTVDKSRWQQGNVFSCSV
MHEALHNHYTQKSLSLSPGKDIDDDDDDD (SEQ ID NO: 1)

FIG. 2

LVPEKEKDPKYWRDQAQETLKYALELQKLNTNVAKNVIMFLGDGMGVSTVTAARILK
GQLHHNPGEETRLEMDKFPFVALSKTYNTNAQVPDSAGTATAYLCGVKANEGTVGVSAATERSR
CnTTQGNEVTSILRWAKDAGKSVGIVTTTRVNHATPSAAYAHSADRDWYSDNEMPPEALSQGCK
DIAYQLMHNIRDIDVIMGGGRKYMYPKnKTDVEYESDEKARGTRLDGLDLVDTWKSFKPRYKHS
HFIWnRTELLTLDPHNVDYLLGLFEPGDMQYELNRRnVTDPSLSEMVVAIQILRKNPKGFFLLVE
GGRIDHGHHEGKAKQALHEAVEMDRAIGQAGSLTSSEDTLTVTADHSHVFTFGGYTPRGNSIFG
LAPMLSDTDKKPFTAILYGNGPGYKVVGGEREnVSMVDYAHNNYQAQSAVPLRHETHGGEDVA
VFSKGPMAHLLHGVHEQNYVPHVMAYAACIGANLGHCAPASSLKDKTHTCPPCPAPELLGGPSV
FLFPPKPKDTLMISRTPEVTCVVVDSHEDPEVKFNWYVDGVEVHNAKTKPREEQYnSTYRVVSV
LTVLHQDWLNGKEYKCKVSNKALPAPIEKTISKAKGQPREPQVYTLPPSREEMTKNQVSLTCLVKG
FYPSDIAVEWESNGQPENNYKTTPPVLDSDGSFFLYSKLTVDKSRWQQGNVFSCSVMHEALHNH
YTQKSLSLSPGKDIDDDDDDDDDD (SEQ ID NO: 4)

*FIG. 3*

| STUDY # | N= | SEVERE | MODERATE | SLIGHT | UNAFFECTED |
|---|---|---|---|---|---|
| HPP-M2h-F4 (COLONY 1) | 38 | 14 (36.84%) | 4 (10.53%) | 11 (28.95%) | 9 (23.68%) |
| HPP-M2h-F10 (COLONY 1) | 42 | 20 (47.63%) | 4 (9.52%) | 4 (9.52%) | 14 (33.33%) |
| HPP-M2h-F4 (COLONY 2) | 48 | 6 (13%) | 18 (37%) | 16 (33%) | 8 (17%) |
| HPP-M2h-F4 (COLONY 3) | 91 | 26 (28.5%) | 11 (12%) | 28 (31%) | 26 (28.5%) |
| HPP-M2h-F4 (COLONY 4) | 49 | 9 (18.37%) | 9 (18.37%) | 18 (36.73%) | 13 (26.53%) |
| HPP-M2h-F10 (COLONY 2) | 32 | 0 (0%) | 8 (25%) | 15 (47%) | 9 (28%) |

FIG. 5

SEQUENCE LISTING

```
<160> NUMBER OF SEQ ID NOS: 4

<210> SEQ ID NO 1
<211> LENGTH: 743
<212> TYPE: PRT
<213> ORGANISM: Artificial Sequence
<220> FEATURE:
<223> OTHER INFORMATION: Synthetic Construct

<400> SEQUENCE: 1

Met Ile Ser Pro Phe Leu Val Leu Ala Ile Gly Thr Cys Leu Thr Asn
1               5                   10                  15

Ser Leu Val Pro Glu Lys Glu Lys Asp Pro Lys Tyr Trp Arg Asp Gln
            20                  25                  30

Ala Gln Glu Thr Leu Lys Tyr Ala Leu Glu Leu Gln Lys Leu Asn Thr
        35                  40                  45

Asn Val Ala Lys Asn Val Ile Met Phe Leu Gly Asp Gly Met Gly Val
    50                  55                  60

Ser Thr Val Thr Ala Ala Arg Ile Leu Lys Gly Gln Leu His His Asn
65                  70                  75                  80

Pro Gly Glu Glu Thr Arg Leu Glu Met Asp Lys Phe Pro Phe Val Ala
                85                  90                  95

Leu Ser Lys Thr Tyr Asn Thr Asn Ala Gln Val Pro Asp Ser Ala Gly
            100                 105                 110

Thr Ala Thr Ala Tyr Leu Cys Gly Val Lys Ala Asn Glu Gly Thr Val
        115                 120                 125

Gly Val Ser Ala Ala Thr Glu Arg Ser Arg Cys Asn Thr Thr Gln Gly
    130                 135                 140

Asn Glu Val Thr Ser Ile Leu Arg Trp Ala Lys Asp Ala Gly Lys Ser
145                 150                 155                 160

Val Gly Ile Val Thr Thr Thr Arg Val Asn His Ala Thr Pro Ser Ala
                165                 170                 175

Ala Tyr Ala His Ser Ala Asp Arg Asp Trp Tyr Ser Asp Asn Glu Met
            180                 185                 190
```

```
Pro Pro Glu Ala Leu Ser Gln Gly Cys Lys Asp Ile Ala Tyr Gln Leu
        195                 200                 205

Met His Asn Ile Arg Asp Ile Asp Val Ile Met Gly Gly Arg Lys
    210                 215                 220

Tyr Met Tyr Pro Lys Asn Lys Thr Asp Val Glu Tyr Glu Ser Asp Glu
225                 230                 235                 240

Lys Ala Arg Gly Thr Arg Leu Asp Gly Leu Asp Leu Val Asp Thr Trp
                245                 250                 255

Lys Ser Phe Lys Pro Arg Tyr Lys His Ser His Phe Ile Trp Asn Arg
            260                 265                 270

Thr Glu Leu Leu Thr Leu Asp Pro His Asn Val Asp Tyr Leu Leu Gly
        275                 280                 285

Leu Phe Glu Pro Gly Asp Met Gln Tyr Glu Leu Asn Arg Asn Asn Val
        290                 295                 300

Thr Asp Pro Ser Leu Ser Glu Met Val Val Ala Ile Gln Ile Leu
305                 310                 315                 320

Arg Lys Asn Pro Lys Gly Phe Phe Leu Leu Val Glu Gly Gly Arg Ile
                325                 330                 335

Asp His Gly His His Glu Gly Lys Ala Lys Gln Ala Leu His Glu Ala
                340                 345                 350

Val Glu Met Asp Arg Ala Ile Gly Gln Ala Gly Ser Leu Thr Ser Ser
                355                 360                 365

Glu Asp Thr Leu Thr Val Val Thr Ala Asp His Ser His Val Phe Thr
        370                 375                 380

Phe Gly Gly Tyr Thr Pro Arg Gly Asn Ser Ile Phe Gly Leu Ala Pro
385                 390                 395                 400

Met Leu Ser Asp Thr Asp Lys Lys Pro Phe Thr Ala Ile Leu Tyr Gly
                405                 410                 415

Asn Gly Pro Gly Tyr Lys Val Val Gly Gly Glu Arg Glu Asn Val Ser
                420                 425                 430

Met Val Asp Tyr Ala His Asn Asn Tyr Gln Ala Gln Ser Ala Val Pro
            435                 440                 445

Leu Arg His Glu Thr His Gly Gly Glu Asp Val Ala Val Phe Ser Lys
        450                 455                 460

Gly Pro Met Ala His Leu Leu His Gly Val His Glu Gln Asn Tyr Val
465                 470                 475                 480

Pro His Val Met Ala Tyr Ala Ala Cys Ile Gly Ala Asn Leu Gly His
                485                 490                 495

Cys Ala Pro Ala Ser Ser Leu Lys Asp Lys Thr His Thr Cys Pro Pro
                500                 505                 510

Cys Pro Ala Pro Glu Leu Leu Gly Gly Pro Ser Val Phe Leu Phe Pro
            515                 520                 525

Pro Lys Pro Lys Asp Thr Leu Met Ile Ser Arg Thr Pro Glu Val Thr
        530                 535                 540

Cys Val Val Val Asp Val Ser His Glu Asp Pro Glu Val Lys Phe Asn
545                 550                 555                 560

Trp Tyr Val Asp Gly Val Glu Val His Asn Ala Lys Thr Lys Pro Arg
                565                 570                 575

Glu Glu Gln Tyr Asn Ser Thr Tyr Arg Val Val Ser Val Leu Thr Val
                580                 585                 590

Leu His Gln Asp Trp Leu Asn Gly Lys Glu Tyr Lys Cys Lys Val Ser
        595                 600                 605
```

```
Asn Lys Ala Leu Pro Ala Pro Ile Glu Lys Thr Ile Ser Lys Ala Lys
610                 615                 620

Gly Gln Pro Arg Glu Pro Gln Val Tyr Thr Leu Pro Pro Ser Arg Glu
625                 630                 635                 640

Glu Met Thr Lys Asn Gln Val Ser Leu Thr Cys Leu Val Lys Gly Phe
                645                 650                 655

Tyr Pro Ser Asp Ile Ala Val Glu Trp Glu Ser Asn Gly Gln Pro Glu
                660                 665                 670

Asn Asn Tyr Lys Thr Thr Pro Pro Val Leu Asp Ser Asp Gly Ser Phe
            675                 680                 685

Phe Leu Tyr Ser Lys Leu Thr Val Asp Lys Ser Arg Trp Gln Gln Gly
690                 695                 700

Asn Val Phe Ser Cys Ser Val Met His Glu Ala Leu His Asn His Tyr
705                 710                 715                 720

Thr Gln Lys Ser Leu Ser Leu Ser Pro Gly Lys Asp Ile Asp Asp Asp
                725                 730                 735

Asp Asp Asp Asp Asp Asp Asp
                740

<210> SEQ ID NO 2
<211> LENGTH: 485
<212> TYPE: PRT
<213> ORGANISM: Homo sapiens

<400> SEQUENCE: 2

Leu Val Pro Glu Lys Glu Lys Asp Pro Lys Tyr Trp Arg Asp Gln Ala
1               5                   10                  15

Gln Glu Thr Leu Lys Tyr Ala Leu Glu Leu Gln Lys Leu Asn Thr Asn
                20                  25                  30

Val Ala Lys Asn Val Ile Met Phe Leu Gly Asp Gly Met Gly Val Ser
            35                  40                  45

Thr Val Thr Ala Ala Arg Ile Leu Lys Gly Gln Leu His His Asn Pro
        50                  55                  60

Gly Glu Glu Thr Arg Leu Glu Met Asp Lys Phe Pro Phe Val Ala Leu
65                  70                  75                  80

Ser Lys Thr Tyr Asn Thr Asn Ala Gln Val Pro Asp Ser Ala Gly Thr
                85                  90                  95

Ala Thr Ala Tyr Leu Cys Gly Val Lys Ala Asn Glu Gly Thr Val Gly
                100                 105                 110

Val Ser Ala Ala Thr Glu Arg Ser Arg Cys Asn Thr Thr Gln Gly Asn
            115                 120                 125

Glu Val Thr Ser Ile Leu Arg Trp Ala Lys Asp Ala Gly Lys Ser Val
        130                 135                 140

Gly Ile Val Thr Thr Thr Arg Val Asn His Ala Thr Pro Ser Ala Ala
145                 150                 155                 160

Tyr Ala His Ser Ala Asp Arg Asp Trp Tyr Ser Asp Asn Glu Met Pro
                165                 170                 175

Pro Glu Ala Leu Ser Gln Gly Cys Lys Asp Ile Ala Tyr Gln Leu Met
                180                 185                 190

His Asn Ile Arg Asp Ile Asp Val Ile Met Gly Gly Gly Arg Lys Tyr
            195                 200                 205

Met Tyr Pro Lys Asn Lys Thr Asp Val Glu Tyr Glu Ser Asp Glu Lys
        210                 215                 220

Ala Arg Gly Thr Arg Leu Asp Gly Leu Asp Leu Val Asp Thr Trp Lys
225                 230                 235                 240
```

```
Ser Phe Lys Pro Arg Tyr Lys His Ser His Phe Ile Trp Asn Arg Thr
                245                 250                 255

Glu Leu Leu Thr Leu Asp Pro His Asn Val Asp Tyr Leu Leu Gly Leu
            260                 265                 270

Phe Glu Pro Gly Asp Met Gln Tyr Glu Leu Asn Arg Asn Asn Val Thr
        275                 280                 285

Asp Pro Ser Leu Ser Glu Met Val Val Val Ala Ile Gln Ile Leu Arg
    290                 295                 300

Lys Asn Pro Lys Gly Phe Phe Leu Leu Val Glu Gly Arg Ile Asp
305                 310                 315                 320

His Gly His His Glu Gly Lys Ala Lys Gln Ala Leu His Glu Ala Val
                325                 330                 335

Glu Met Asp Arg Ala Ile Gly Gln Ala Gly Ser Leu Thr Ser Ser Glu
            340                 345                 350

Asp Thr Leu Thr Val Val Thr Ala Asp His Ser His Val Phe Thr Phe
        355                 360                 365

Gly Gly Tyr Thr Pro Arg Gly Asn Ser Ile Phe Gly Leu Ala Pro Met
    370                 375                 380

Leu Ser Asp Thr Asp Lys Lys Pro Phe Thr Ala Ile Leu Tyr Gly Asn
385                 390                 395                 400

Gly Pro Gly Tyr Lys Val Val Gly Gly Glu Arg Glu Asn Val Ser Met
                405                 410                 415

Val Asp Tyr Ala His Asn Asn Tyr Gln Ala Gln Ser Ala Val Pro Leu
            420                 425                 430

Arg His Glu Thr His Gly Gly Glu Asp Val Ala Val Phe Ser Lys Gly
        435                 440                 445

Pro Met Ala His Leu Leu His Gly Val His Glu Gln Asn Tyr Val Pro
    450                 455                 460

His Val Met Ala Tyr Ala Ala Cys Ile Gly Ala Asn Leu Gly His Cys
465                 470                 475                 480

Ala Pro Ala Ser Ser
                485

<210> SEQ ID NO 3
<211> LENGTH: 227
<212> TYPE: PRT
<213> ORGANISM: Artificial Sequence
<220> FEATURE:
<223> OTHER INFORMATION: Synthetic Construct

<400> SEQUENCE: 3

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110
```

```
Glu Lys Thr Ile Ser Lys Ala Lys Gly Gln Pro Arg Glu Pro Gln Val
            115                 120                 125

Tyr Thr Leu Pro Pro Ser Arg Glu Glu Met Thr Lys Asn Gln Val Ser
        130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
        210                 215                 220

Pro Gly Lys
225

<210> SEQ ID NO 4
<211> LENGTH: 726
<212> TYPE: PRT
<213> ORGANISM: Artificial Sequence
<220> FEATURE:
<223> OTHER INFORMATION: Synthetic Construct

<400> SEQUENCE: 4

Leu Val Pro Glu Lys Glu Lys Asp Pro Lys Tyr Trp Arg Asp Gln Ala
1               5                   10                  15

Gln Glu Thr Leu Lys Tyr Ala Leu Glu Leu Gln Lys Leu Asn Thr Asn
            20                  25                  30

Val Ala Lys Asn Val Ile Met Phe Leu Gly Asp Gly Met Gly Val Ser
        35                  40                  45

Thr Val Thr Ala Ala Arg Ile Leu Lys Gly Gln Leu His His Asn Pro
    50                  55                  60

Gly Glu Glu Thr Arg Leu Glu Met Asp Lys Phe Pro Phe Val Ala Leu
65                  70                  75                  80

Ser Lys Thr Tyr Asn Thr Asn Ala Gln Val Pro Asp Ser Ala Gly Thr
                85                  90                  95

Ala Thr Ala Tyr Leu Cys Gly Val Lys Ala Asn Glu Gly Thr Val Gly
            100                 105                 110

Val Ser Ala Ala Thr Glu Arg Ser Arg Cys Asn Thr Thr Gln Gly Asn
        115                 120                 125

Glu Val Thr Ser Ile Leu Arg Trp Ala Lys Asp Ala Gly Lys Ser Val
    130                 135                 140

Gly Ile Val Thr Thr Thr Arg Val Asn His Ala Thr Pro Ser Ala Ala
145                 150                 155                 160

Tyr Ala His Ser Ala Asp Arg Asp Trp Tyr Ser Asp Asn Glu Met Pro
                165                 170                 175

Pro Glu Ala Leu Ser Gln Gly Cys Lys Asp Ile Ala Tyr Gln Leu Met
            180                 185                 190

His Asn Ile Arg Asp Ile Asp Val Ile Met Gly Gly Gly Arg Lys Tyr
        195                 200                 205

Met Tyr Pro Lys Asn Lys Thr Asp Val Glu Tyr Glu Ser Asp Glu Lys
    210                 215                 220

Ala Arg Gly Thr Arg Leu Asp Gly Leu Asp Leu Val Asp Thr Trp Lys
225                 230                 235                 240
```

```
Ser Phe Lys Pro Arg Tyr Lys His Ser His Phe Ile Trp Asn Arg Thr
                245                 250                 255

Glu Leu Leu Thr Leu Asp Pro His Asn Val Asp Tyr Leu Leu Gly Leu
                260                 265                 270

Phe Glu Pro Gly Asp Met Gln Tyr Glu Leu Asn Arg Asn Asn Val Thr
                275                 280                 285

Asp Pro Ser Leu Ser Glu Met Val Val Ala Ile Gln Ile Leu Arg
                290                 295                 300

Lys Asn Pro Lys Gly Phe Phe Leu Leu Val Glu Gly Gly Arg Ile Asp
305                 310                 315                 320

His Gly His His Glu Gly Lys Ala Lys Gln Ala Leu His Glu Ala Val
                325                 330                 335

Glu Met Asp Arg Ala Ile Gly Gln Ala Gly Ser Leu Thr Ser Ser Glu
                340                 345                 350

Asp Thr Leu Thr Val Val Thr Ala Asp His Ser His Val Phe Thr Phe
                355                 360                 365

Gly Gly Tyr Thr Pro Arg Gly Asn Ser Ile Phe Gly Leu Ala Pro Met
                370                 375                 380

Leu Ser Asp Thr Asp Lys Lys Pro Phe Thr Ala Ile Leu Tyr Gly Asn
385                 390                 395                 400

Gly Pro Gly Tyr Lys Val Val Gly Gly Glu Arg Glu Asn Val Ser Met
                405                 410                 415

Val Asp Tyr Ala His Asn Asn Tyr Gln Ala Gln Ser Ala Val Pro Leu
                420                 425                 430

Arg His Glu Thr His Gly Gly Glu Asp Val Ala Val Phe Ser Lys Gly
                435                 440                 445

Pro Met Ala His Leu Leu His Gly Val His Glu Gln Asn Tyr Val Pro
                450                 455                 460

His Val Met Ala Tyr Ala Ala Cys Ile Gly Ala Asn Leu Gly His Cys
465                 470                 475                 480

Ala Pro Ala Ser Ser Leu Lys Asp Lys Thr His Thr Cys Pro Pro Cys
                485                 490                 495

Pro Ala Pro Glu Leu Leu Gly Gly Pro Ser Val Phe Leu Phe Pro Pro
                500                 505                 510

Lys Pro Lys Asp Thr Leu Met Ile Ser Arg Thr Pro Glu Val Thr Cys
                515                 520                 525

Val Val Val Asp Val Ser His Glu Asp Pro Glu Val Lys Phe Asn Trp
                530                 535                 540

Tyr Val Asp Gly Val Glu Val His Asn Ala Lys Thr Lys Pro Arg Glu
545                 550                 555                 560

Glu Gln Tyr Asn Ser Thr Tyr Arg Val Val Ser Val Leu Thr Val Leu
                565                 570                 575

His Gln Asp Trp Leu Asn Gly Lys Glu Tyr Lys Cys Lys Val Ser Asn
                580                 585                 590

Lys Ala Leu Pro Ala Pro Ile Glu Lys Thr Ile Ser Lys Ala Lys Gly
                595                 600                 605

Gln Pro Arg Glu Pro Gln Val Tyr Thr Leu Pro Pro Ser Arg Glu Glu
                610                 615                 620

Met Thr Lys Asn Gln Val Ser Leu Thr Cys Leu Val Lys Gly Phe Tyr
625                 630                 635                 640

Pro Ser Asp Ile Ala Val Glu Trp Glu Ser Asn Gly Gln Pro Glu Asn
                645                 650                 655
```

-continued

```
Asn Tyr Lys Thr Thr Pro Pro Val Leu Asp Ser Asp Gly Ser Phe Phe
            660             665             670

Leu Tyr Ser Lys Leu Thr Val Asp Lys Ser Arg Trp Gln Gln Gly Asn
        675             680             685

Val Phe Ser Cys Ser Val Met His Glu Ala Leu His Asn His Tyr Thr
        690             695             700

Gln Lys Ser Leu Ser Leu Ser Pro Gly Lys Asp Ile Asp Asp Asp Asp
705             710             715             720

Asp Asp Asp Asp Asp Asp
            725
```

TREATING SEIZURE WITH RECOMBINANT ALKALINE PHOSPHATASE

SEQUENCE LISTING

The instant application contains a Sequence Listing which has been submitted electronically in ASCII format and is hereby incorporated by reference in its entirety. Said ASCII copy, created on Dec. 1, 2015, is named 0239PCT_SL.txt and is 19,449 bytes in size.

TECHNICAL FIELD

The present disclosure relates to the method of treating seizure in HPP or non-HPP patients. More specifically, the present disclosure relates to identifying a subpopulation of HPP patients or non-HPP patients having aberrant levels and/or functions of at least one of alkaline phosphatase substrates but having normal or unaffected mineralization phenotype and treating such subpopulation of patients with at least one of recombinant alkaline phosphatase.

BACKGROUND

Hypophosphatasia (HPP) is a rare, heritable form of rickets or osteomalacia with an incidence as great as one per 2,500 births in Canadian Mennonites and of one per 100,000 births in the general population for the more severe form of the disease. Milder forms are more prevalent. This "inborn error of metabolism" is caused by loss-of-function mutation(s) in the gene (ALPL) that encodes the tissue-nonspecific isozyme of alkaline phosphatase (TNALP; a.k.a., liver/bone/kidney type ALP). The biochemical hallmark is subnormal ALP activity in serum (hypophosphatasemia), which leads to elevated blood and/or urine levels of three phospho-compound substrates: inorganic pyrophosphate (PPi), phosphoethanolamine (PEA) and pyridoxal 5'-phosphate (PLP).

HPP features perinatal, infantile, childhood, adult, and odontohypophosphatasia forms, classified historically according to age at diagnosis. Phenotype ranges from almost complete absence of bone mineralization in utero with stillbirth, to spontaneous fractures and dental disease occurring first in adult life. Perinatal lethal HPP (perinatal HPP, or PL-HPP) is expressed in utero and can cause stillbirth. Some neonates survive several days, but suffer increasing respiratory compromise due to the hypoplastic and rachitic disease of the chest. In infantile HPP, diagnosed before six months of age, postnatal development seems normal until onset of poor feeding, inadequate weight gain, and appearance of rickets. Radiological features are characteristic and show impaired skeletal mineralization, sometimes with progressive skeletal demineralization leading to rib fractures and chest deformity. Childhood HPP has highly variable clinical expression. Premature loss of deciduous teeth results from aplasia, hypoplasia, or dysplasia of dental cementum that connects the tooth root with the periodontal ligament. Rickets causes short stature and skeletal deformities including, for example, bowed legs, enlargement of the wrists, knees, and ankles as a result of flared metaphysis. Adult HPP usually presents during middle age, although frequently there is a history of rickets and/or early loss of teeth followed by good health during adolescence and young adult life. Recurrent metatarsal stress fractures are common, and calcium pyrophosphate dihydrate deposition causes attacks of arthritis and pyrophosphate arthropathy. Odontohypophosphatasia is diagnosed when the only clinical abnormality is dental disease and radiological studies and even bone biopsies reveal no signs of rickets or osteomalacia.

The severe clinical forms of HPP are usually inherited as autosomal recessive traits with parents of such patients showing subnormal levels of serum AP activity. For the milder forms of HPP, e.g., adult and odontohypophosphatasia, an autosomal dominant pattern of inheritance has also been documented.

Since the occurrence of HPP is rare, the diagnosis of HPP is usually missed at the early stages of illness. In addition, most HPP symptoms, such as abnormal skull shape, back pain, bone fractures, bone spurs (bumps around the joints), bow legs, bumps in the rib cage, loss of height over time/short stature, and pain in the joints, are similar to symptoms caused by other more common diseases, such as osteogenesis imperfecta, nutritional rickets, osteoarthritis, and osteoporosis. Other factors that are sometimes used to diagnosis HPP include, for example, low levels of alkaline phosphatase (ALP) in the blood, higher than normal levels of calcium in the blood and urine, bone changes (including bowing (bending) of bones in the arms and legs), poor growth, thick wrists and ankles, loose ligaments, bone pain, fractures, premature tooth loss, family history of HPP, and mutations in the ALPL gene.

As HPP patients may develop symptoms (e.g., mineralization defects) with different severity, there is an unidentified subpopulation of HPP patients with minor to none of the typical HPP symptoms, who have been traditionally misdiagnosed and/or ignored for treatment (such as enzyme replacement with recombinant TNALP). Moreover, many HPP patients have additional symptoms (such as seizures) in addition to their characteristic mineralization defect(s). Thus, there exists a need to identify such patient populations not only for monitoring (and thus early treatment for) potential health deterioration with HPP symptoms, but also for treating symptoms other than mineralization defects with recombinant TNALP.

SUMMARY

The present disclosure provides a method of identifying a population of subjects with alkaline phosphatase (e.g., ALPL in human and Akp2 in mice) gene mutations. Such population of subjects may be previously diagnosed or may be not yet diagnosed with HPP. Such gene mutations may result in reduced alkaline phosphatase protein levels and/or protein function(s) (e.g., enzymatic functions towards PPi, PLP, and/or PEA, or other substrates such as para-Nitrophenylphosphate (pNPP)). Such gene mutations may be identified by well-known methods in the art. After identifying such a population, close monitoring will follow their disease progression with seizures and/or with other HPP symptoms. Recombinant alkaline phosphatase will be supplied to such population to treat or prevent seizures and/or other symptoms.

The present disclosure in one aspect provides a method of identifying a population of subjects with alkaline phosphatase gene mutations and at least one symptom. In some embodiments, subjects in such population have been previously diagnosed with HPP but have minor, unaffected, or undetectable bone and/or teeth mineralization defects. In other embodiments, subjects in such population have not yet been diagnosed with HPP. In one embodiment, subjects in such population have not yet been diagnosed with HPP and have no characteristic HPP symptoms (such as bone and/or teeth mineralization defects). In some embodiments, the at least one non-HPP symptom is seizure. Such seizure may be responsive or nonresponsive to vitamin B6 and/or other traditional anti-seizure drug treatment(s). The term "undetectable" in the present disclosure refers to a scenario when a phenotype (e.g., one of bone and/or teeth mineralization phenotypes) on a patient is too minor to be detectable by a person of ordinary skill in the art using common technology known in the art, or a scenario when such person of ordinary skill in the art cannot differentiate the phenotype on that patient from the phenotype of a common healthy person or a common patient without a disease or disorder in which the phenotype is a commonly accepted diagnosis standard (e.g., HPP). The term "unaffected" in the present disclosure refer to the scenario when a phenotype (e.g., bone and/or teeth mineralization phenotypes) on a patient is undetectable or is detectable but too minor to meet the commonly accepted diagnosis threshold so that such patient with the phenotype is considered by a person of ordinary skill in the art as a patient having a disease or disorder in which the phenotype is a commonly accepted diagnosis standard (e.g., HPP).

The present disclosure provides a method of identifying a subpopulation of subjects having HPP, comprising measuring the degree of mineralization of bones and/or teeth of those subjects and comparing such degree with those of normal healthy subjects, wherein such subjects in the subpopulation have minor, unaffected, or undetectable mineralization defects compared to normal healthy subjects. In some embodiments, such subjects in the subpopulation have seizure symptoms. Such seizure symptoms may be responsive or nonresponsive to vitamin B6 and/or other traditional anti-seizure drug treatment(s).

The present disclosure provides a method of identifying a subpopulation of subjects having not been diagnosed with HPP, comprising measuring alkaline phosphatase levels and/or enzymatic functions in such subpopulation, wherein such subjects in the subpopulation have defective alkaline phosphatase levels and/or enzymatic functions compared to normal healthy subjects. In some embodiments, such subjects in the subpopulation have seizure symptoms. Such seizure symptoms may be responsive or nonresponsive to vitamin B6 and/or other traditional anti-seizure drug treatment(s). Traditional technology in the art can be applied to measure alkaline phosphatase levels in those subjects. For example, the DNA/RNA levels of alkaline phosphatase may be tested by PCR or hybridization (e.g., Southern/Northern blot) methods used in genetic screening. The protein levels of alkaline phosphatase may be tested by PAGE/SDS-PAGE, Western blot, ELISA or other immunoassays using anti-alkaline phosphatase antibodies. The enzymatic functions of alkaline phosphatase may be tested in vitro or in vivo using alkaline phosphatase substrates PPi, PLP, and/or PEA, or other substrates such as para-Nitrophenylphosphate (pNPP). In one embodiment, such subjects in the subpopulation have minor, unaffected, or undetectable mineralization defects.

As one aspect, the present disclosure provides a method of identifying a population or subpopulation of subject as disclosed above. As another aspect, the present disclosure provides a method of treating at least one symptom in those subjects in the identified population or subpopulation with recombinant ALP supplementation. In some embodiments, such at least one symptom is seizure, either responsive or nonresponsive to vitamin B6 and/or other anti-seizure drug treatment(s).

In some embodiments, the present disclosure provides a method of treating seizure in a subject having aberrant alkaline phosphatase activities comprising administering a therapeutically effective amount of at least one recombinant alkaline phosphatase to the subject. Such aberrant alkaline phosphatase activities may be due to aberrant protein levels and/or function of at least one alkaline phosphatase in the subject. The alkaline phosphatase activities disclosed herein can be measured by the enzymatic activity of the at least one recombinant alkaline phosphatase under physiological conditions toward phsphoethanolamine (PEA), inorganic pyrophosphate (PPi), and/or pyridoxal 5'-phosphate (PLP), or other substrates such as para-Nitrophenylphosphate (pNPP). In one preferred embodiment, the at least one alkaline phosphatase substrate is selected from the group consisting of PLP, PPi, and PEA.

In some embodiments, the present disclosure provides a method of treating seizure in a subject having above-normal levels of at least one alkaline phosphatase substrate, comprising administering a therapeutically effective amount of at least one recombinant alkaline phosphatase to the subject. In one embodiment, the at least one alkaline phosphatase substrate is selected from the group consisting of PLP, PPi, PEA, and other substrates such as para-Nitrophenylphosphate (pNPP). In one preferred embodiment, the at least one alkaline phosphatase substrate is selected from the group consisting of PLP, PPi, and PEA.

In the present disclosure various terms such as "above-normal," "lower than normal," "higher than normal," or similar others refer to levels and/or activities of at least one molecule in a specific subject (e.g., a human) which are above, lower, or higher than the levels and/or activities of said at least one molecule (or its/their endogenous counterpart(s)) in a normal subject (e.g., a normal human). The most obvious example for a normal human is a human being who has no HPP or HPP symptoms and has no mutations or modifications to ALPL gene and ALP proteins which may result in HPP-related symptoms. In another scenario focusing on ALP functions, the scope of a "normal" human in the present disclosure may be broadened to include any human beings having no aberrant endogenous alkaline phosphatase activity (which may be tested by, e.g., the substrate (PPi, PEA, PLP, or pNPP) levels and compared to the corresponding activity in other healthy or normal human beings).

In other embodiments, the present disclosure provides a method of treating seizure in a subject comprising:

(i) identifying a subpopulation of subjects with aberrant alkaline phosphatase activities (e.g., due to aberrant protein levels and/or function) who suffer, or are likely to suffer, from seizure; and (ii) administering a therapeutically effective amount of at least one recombinant alkaline phosphatase to a subject in the subpopulation. The alkaline phosphatase activities disclosed herein can be measured by the enzymatic activity of the at least one recombinant alkaline phosphatase under physiological conditions toward phsphoethanolamine (PEA), inorganic pyrophosphate (PPi) and/or pyridoxal 5'-phosphate (PLP), or other substrates such as para-Nitrophenylphosphate (pNPP). In one preferred embodiment, the at least one alkaline phosphatase substrate is selected from the group consisting of PLP, PPi, and PEA.

In some embodiments, the present disclosure provides a method of treating seizure in a subject comprising:

(i) identifying a population of subjects with above-normal levels of at least one alkaline phosphatase substrate who suffer, or are at risk to suffer from seizure; and (ii) administering a therapeutically effective amount of at least one recombinant alkaline phosphatase to a subject in the population. In one embodiment, the at least one alkaline phosphatase substrate is selected from the group consisting of PLP, PPi, PEA, and other substrates such as para- Nitrophenylphosphate (pNPP). In one preferred embodiment, the at least one alkaline phosphatase substrate is selected from the group consisting of PLP, PPi, and PEA.

The subjects of the population or subpopulation disclosed herein may be hypophosphatasia (HPP) patients having minor or non-detectable bone and/or teeth mineralization defects, non-HPP patients, or subjects who have not been diagnosed with HPP.

The subjects of the population or subpopulation disclosed herein may have increased serum pyridoxal 5'-phosphate (PLP) and/or reduced intracellular pyridoxal 5'-phosphate (PLP).

The subjects of the population or subpopulation disclosed herein may have reduced at least one of Gamma-Aminobutyric Acid (GABA) and serine levels in brain and/or other tissues/organs. The subjects of the population or subpopulation disclosed herein may have at least one of increased cystathionine levels in brain and other tissues/organs (e.g. detectable in urine). In one embodiment, the subject has at least one of reduced brain GABA and reduced brain serine. In another embodiment, the subject has at least one of increased brain and urinary cystathionine.

In some embodiments, the at least one recombinant alkaline phosphatase disclosed herein is administered to the subjects of the subpopulation continuously for at least one week, one month, three months, six months, or one year. For example, the at least one recombinant alkaline phosphatase may be administered daily for 3 days, one week, two weeks, one month, two months, three months, four months, five months, six months, seven months, eight months, nine months, ten months, eleven months, one year, fifteen months, eighteen months, two years, thirty months, three years, or for a longer period.

In one embodiment, the administration of the at least one recombinant alkaline phosphatase elevates brain GABA and/or serine levels. In another embodiment, the administration of the at least one recombinant alkaline phosphatase decreases brain and/or urine cystathionine levels.

In some embodiments, a therapeutically effective amount of at least one additional therapeutic agent is administered to the subject of the population or subpopulation disclosed herein in conjunction to the at least one recombinant alkaline phosphatase described herein. In one embodiment, such at least one additional therapeutic agent comprises at least one anti-seizure drug. Such at least one anti-seizure drug may be one or more drug or drugs, and includes but is not limited to, for example, vitamin B6 and its variants, any anti-seizure drug blocking sodium channels or enhancing γ-aminobutyric acid (GABA) function, GABAA receptors, the GAT-1 GABA transporter, GABA transaminase, any anti-seizure drug blocking voltage-gated calcium channels, Synaptic vesicle glycoprotein 2A (SV2A), α2δ-aldehydes (e.g., Paraldehyde), aromatic allylic alcohols (e.g., Stiripentol), barbiturates (e.g., Phenobarbital, Methylphenobarbital, and Barbexaclone), benzodiazepines (e.g., Clobazam, Clonazepam, Clorazepate, Diazepam, Midazolam, Lorazepam, Nitrazepam, Temazepam, and Nimetazepam), bromides (e.g., potassium bromide), carbamates (e.g., Felbamate), carboxamides (e.g., Carbamazepine, Oxcarbazepine, and Eslicarbazepine acetate), fatty acids (e.g., valproates, Vigabatrin, Progabide, and Tiagabine), fructose derivatives (e.g., Topiramate), GABA analogs (e.g., Gabapentin and Pregabalin), hydantoins (e.g., Ethotoin, Phenytoin, Mephenytoin, and Fosphenytoin), oxazolidinediones (e.g., Paramethadione, Trimethadione, dimethadione, and Ethadione), propionates (e.g., Beclamide), pyrimidinediones (e.g., Primidone), pyrrolines (e.g., Brivaracetam, Levetiracetam, and Seletracetam), succinimides (e.g., Ethosuximide, Phensuximide, and Mesuximide), suflonamides (e.g., Acetazolamide, Sultiame, Methazolamide, and Zonisamide), triazines (e.g., Lamotrigine), ureas (e.g., Pheneturide and Phenacemide), valproylamides (amide derivatives of valproate) (e.g., Valpromide and Valnoctamide), or others (e.g., Perampanel). The term "in conjunction to" or "in conjunction with" of the present disclosure means that at least two actions (e.g., at least two administrations of any recombinant alkaline phosphatase and/or any additional anti-seizure drug disclosed herein) occur at the same point in time or space, including but not limited to: in the same formulation for administration, in different formulations but administered in the same time, in different formulations and administered one after another with an interval time short enough to be considered by a skilled artisan as being administered in the same time, and in different formulations and administered one after another with an interval time of at least, e.g., 30 mins, one hour, two hours, four hours, six hours, eight hours, twelve hours, eighteen hours, one day, two days, three days, one week, two weeks, or a longer time, given that such interval time is considered by a skilled artisan as being administered at the same point in time or space but not in different administration time points for therapy.

As another aspect, the present disclosure provides a method of treating seizure as disclosed herein, further comprising:

maintaining co-administration of the at least one additional anti-seizure drug and the at least one recombinant alkaline phosphatase for a pre-determined time; and withdrawing administration of the at least one additional anti-seizure drug but maintaining administration of the at least one recombinant alkaline phosphatase to the subject.

In some embodiments, the at least one additional anti-seizure drug and the at least one recombinant alkaline phosphatase disclosed herein are co-administered to the subject for at least one month, at least six months, or at least one year. For example, the pre-determined time for co-administration may be at least 3 days, one week, two weeks, one month, two months, three months, four months, five months, six months, seven months, eight months, nine months, ten months, eleven months, one year, fifteen months, eighteen months, two years, thirty months, three years, or for a longer period. In one embodiment, the at least one additional anti-seizure drug is at least one of vitamin B6 (pyridoxine) or its variants.

In some embodiments, the at least one recombinant alkaline phosphatase described herein for treatment is physiologically active towards phosphoethanolamine (PEA), inorganic pyrophosphate (PPi) and/or pyridoxal 5'-phosphate (PLP), or other substrates such as para-Nitrophenylphosphate (pNPP). In some embodiments, such at least one recombinant alkaline phosphatase comprises a tissue non-specific alkaline phosphatase (TNALP), a placental alkaline phosphatase (PALP), a germ cell alkaline phosphatase (GCALP), an intestinal alkaline phosphatase (IALP), or functional fragments, fusions, or chimeric constructs thereof. In one embodiment, such at least one recombinant alkaline phosphatase is a soluble fragment of TNALP, PALP, GCALP, or IALP, or their functional fragments, fusions, or chimeric constructs thereof. In one embodiment, such at least one recombinant alkaline phosphatase is a fusion or chimeric protein comprising fragments or portions from at least one, two, three, or four different types of alkaline phosphatases, such as a TNALP-IALP chimeric construct, an IALP-PALP chimeric construct, and other TNALP chimeric or fusion proteins. In one embodiment, the at least one recombinant alkaline phosphatase of the present disclosure comprises an amino acid sequence as listed in SEQ ID NO: 2. In some other embodiments, the at least one recombinant alkaline phosphatase of the present disclosure comprises an amino acid sequence having at least 70%, 75%, 80%, 85%, 90%, 95%, 96%, 97%, 98%, 99%, or higher sequence identity with SEQ ID NO: 2. In one embodiment, the at least one recombinant alkaline phosphatase of the present disclosure comprises an amino acid sequence having at least 75% sequence identity with SEQ ID NO: 2. In another embodiment, the at least one recombinant alkaline phosphatase of the present disclosure comprises an amino acid sequence having at least 80% sequence identity with SEQ ID NO: 2. In another embodiment, the at least one recombinant alkaline phosphatase of the present disclosure comprises an amino acid sequence having at least 85% sequence identity with SEQ ID NO: 2. In another embodiment, the at least one recombinant alkaline phosphatase of the present disclosure comprises an amino acid sequence having at least 90% sequence identity with SEQ ID NO: 2. In another embodiment, the at least one recombinant alkaline phosphatase of the present disclosure comprises an amino acid sequence having at least 95% sequence identity with SEQ ID NO: 2. In one embodiment, the at least one recombinant alkaline phosphatase of the present disclosure is encoded by a polynucleotide molecule encoding a polypeptide comprising a sequence as listed in SEQ ID NO: 2. In some other embodiments, the at least one recombinant alkaline phosphatase of the present disclosure is encoded by a polynucleotide molecule encoding a polypeptide comprising an amino acid sequence having at least 70%, 75%, 80%, 85%, 90%, 95%, 96%, 97%, 98%, 99%, or higher sequence identity with SEQ ID NO: 2. In one embodiment, the at least one recombinant alkaline phosphatase of the present disclosure is encoded by a polynucleotide molecule encoding a polypeptide comprising an amino acid sequence having at least 75% sequence identity with SEQ ID NO: 2. In another embodiment, the at least one recombinant alkaline phosphatase of the present disclosure is encoded by a polynucleotide molecule encoding a polypeptide comprising an amino acid sequence having at least 80% sequence identity with SEQ ID NO: 2. In another embodiment, the at least one recombinant alkaline phosphatase of the present disclosure is encoded by a polynucleotide molecule encoding a polypeptide comprising an amino acid sequence having at least 85% sequence identity with SEQ ID NO: 2. In another embodiment, the at least one recombinant alkaline phosphatase of the present disclosure is encoded by a polynucleotide molecule encoding a polypeptide comprising an amino acid sequence having at least 90% sequence identity with SEQ ID NO: 2. In another embodiment, the at least one recombinant alkaline phosphatase of the present disclosure is encoded by a polynucleotide molecule encoding a polypeptide comprising an amino acid sequence having at least 95% sequence identity with SEQ ID NO: 2. In one embodiment, the at least one recombinant alkaline phosphatase of the present disclosure is encoded by a polynucleotide molecule which is hybridizable under high stringency conditions to at least one polynucleotide molecule encoding a polypeptide comprising an amino acid sequence having at least 90%, 95%, or higher sequence identity with SEQ ID NO: 2, wherein the high stringency conditions comprise: pre-hybridization and hybridization in 6×SSC, 5×Denhardt's reagent, 0.5% SDS and 100 mg/ml of denatured fragmented salmon sperm DNA at 68° C.; and washes in 2×SSC and 0.5% SDS at room temperature for 10 min; in 2×SSC and 0.1% SDS at room temperature for 10 min; and in 0.1×SSC and 0.5% SDS at 65° C. three times for 5 minutes.

In some embodiments, the at least one recombinant alkaline phosphatase described herein for treatment is a fusion protein. At least one linker known in the art may be inserted in such fusion protein. In some embodiments, the at least one recombinant alkaline phosphatase is fused to an immunoglobulin molecule. In one embodiment, the immunoglobulin molecule is a fragment crystallizable region (Fc). In another embodiment, the Fc comprises an amino acid sequence as listed in SEQ ID NO: 3. In some other embodiments, the Fc comprises an amino acid sequence having at least 70%, 75%, 80%, 85%, 90%, 95%, 96%, 97%, 98%, 99%, or higher sequence identity with SEQ ID NO: 3. In some other embodiments, the Fc is encoded by a polynucleotide molecule encoding a polypeptide comprises an amino acid sequence having at least 70%, 75%, 80%, 85%, 90%, 95%, 96%, 97%, 98%, 99%, or higher sequence identity with SEQ ID NO: 3. In one embodiment, the Fc is encoded by a polynucleotide molecule which is hybridizable under high stringency conditions to at least one polynucleotide molecule encoding a polypeptide comprising an amino acid sequence having at least 90%, 95%, or higher sequence identity with SEQ ID NO: 3, wherein the high stringency conditions comprise: pre-hybridization and hybridization in 6×SSC, 5×Denhardt's reagent, 0.5% SDS and 100 mg/ml of denatured fragmented salmon sperm DNA at 68° C.; and washes in 2×SSC and 0.5% SDS at room temperature for 10 min; in 2×SSC and 0.1% SDS at room temperature for 10 min; and in 0.1×SSC and 0.5% SDS at 65° C. three times for 5 minutes.

In other embodiments, the at least one recombinant alkaline phosphatase described herein for treatment is fused to a negatively charged peptide. Such negatively charged peptide may include poly-aspartate or poly-glutamate of any length, e.g., from 6 to 20 amino acid residues. In some embodiments, the negatively charged peptide is D10, D8, D16, E10, E8, or E16. In some embodiments, the negatively charged peptide is D10, D16, E10, or E16. In one preferred embodiment, the negatively charged peptide is D10.

In some embodiments, the at least one recombinant alkaline phosphatase described herein comprises a soluble ALP (sALP) fusion protein comprising a structure of sALP-Fc-D10, or a structure of sALP-Fc, Fc-sALP, Fc-sALP-D10, D10-sALP-Fc, or D10-Fc-sALP. In one embodiment, the at least one recombinant alkaline phosphatase described herein comprises a structure of sALP-Fc-D10. In another embodiment, the at least one recombinant alkaline phosphatase comprises an amino acid sequence as listed in SEQ ID NO: 1 or 4. In some other embodiments, the at least one recombinant alkaline phosphatase comprises an amino acid sequence having at least 70%, 75%, 80%, 85%, 90%, 95%, 96%, 97%, 98%, 99%, or higher sequence identity with SEQ ID NO: 1 or 4. In some other embodiments, the at least one recombinant alkaline phosphatase is encoded by a polynucleotide molecule encoding a polypeptide comprises an amino acid sequence having at least 70%, 75%, 80%, 85%, 90%, 95%, 96%, 97%, 98%, 99%, or higher sequence identity with SEQ ID NO: 1 or 4. In one embodiment, the at least one recombinant alkaline phosphatase is encoded by a polynucleotide molecule which is hybridizable under high stringency conditions to at least one polynucleotide molecule encoding a polypeptide comprising an amino acid sequence having at least 90%, 95%, or higher sequence identity with SEQ ID NO: 1 or 4, wherein the high stringency conditions comprise: pre-hybridization and hybridization in 6×SSC, 5×Denhardt's reagent, 0.5% SDS and 100 mg/ml of denatured fragmented salmon sperm DNA at 68° C.; and washes in 2×SSC and 0.5% SDS at room temperature for 10 min; in 2×SSC and 0.1% SDS at room temperature for 10 min; and in 0.1×SSC and 0.5% SDS at 65° C. three times for 5 minutes.

In some embodiments, the at least one recombinant alkaline phosphatase described herein can be administered in a dosage from about 0.1 mg/kg/day to about 20 mg/kg/day, from about 0.1 mg/kg/day to about 10 mg/kg/day, from about 0.1 mg/kg/day to about 8 mg/kg/day, from about 0.1 mg/kg/day to about 5 mg/kg/day, from about 0.1 mg/kg/day to about 1 mg/kg/day, from about 0.1 mg/kg/day to about 0.5 mg/kg/day, from about 0.5 mg/kg/day to about 20 mg/kg/day, from about 0.5 mg/kg/day to about 10 mg/kg/day, from about 0.5 mg/kg/day to about 8 mg/kg/day, from about 0.5 mg/kg/day to about 5 mg/kg/day, from about 0.5 mg/kg/day to about 1 mg/kg/day, from about 1 mg/kg/day to about 20 mg/kg/day, from about 1 mg/kg/day to about 10 mg/kg/day, from about 1 mg/kg/day to about 8 mg/kg/day, from about 1 mg/kg/day to about 5 mg/kg/day, or a comparable weekly dosage (e.g., 6 mg/kg/week is comparable to 1 mg/kg/day). The administration route for the at least one recombinant alkaline phosphatase described herein may include any known methods in the art, including, at least, intravenously, intramuscularly, subcutaneously, sublingually, intrathecally and/or intradermally administration. In one embodiment, the at least one recombinant alkaline phosphatase is administered intravenously. In some embodiments, the at least one recombinant alkaline phosphatase is administered in multiple dosages through a same or different routes. In other embodiments, at least one recombinant alkaline phosphatase is administered in multiple dosages through different routes concurrently or sequentially. For example, the at least one recombinant alkaline phosphatase may be administered first intravenously and then, in later dosages, subcutaneously. Alternatively, intravenous administration may also be used in later dosages for quick therapeutic responses. Choice of routes for multiple dosages may be determined by a skilled artisan to achieve the most efficacy, stability (e.g., half-life of the at least one recombinant alkaline phosphatase and/or the at least one additional anti-seizure drug), efficiency, and/or cost-effective goals. No specific limitation on the choice of administration routes and/or the application of different administration routes in different dosages is intended by the present disclosure.

As another aspect, the present disclosure provides a method of treating seizure in a subject having aberrant alkaline phosphatase activities, comprising administering a therapeutically effective amount of at least one recombinant alkaline phosphatase to said subject, wherein the at least one recombinant alkaline phosphatase comprises a structure of sALP-Fc-D10. In one embodiment, such at least one recombinant alkaline phosphatase comprises an amino acid sequence having at least 70%, 75%, 80%, 85%, 90%, 95%, 96%, 97%, 98%, 99%, or higher sequence identity with SEQ ID NO: 2. In another embodiment, such at least one recombinant alkaline phosphatase of the present disclosure is encoded by a polynucleotide molecule encoding a polypeptide comprising an amino acid sequence having at least 70%, 75%, 80%, 85%, 90%, 95%, 96%, 97%, 98%, 99%, or higher sequence identity with SEQ ID NO: 2. In another embodiment, the at least one recombinant alkaline phosphatase is encoded by a polynucleotide molecule which is hybridizable under high stringency conditions to at least one polynucleotide molecule encoding a polypeptide comprising an amino acid sequence having at least 90%, 95%, or higher sequence identity with SEQ ID NO: 2, wherein the high stringency conditions comprise: pre-hybridization and hybridization in 6×SSC, 5×Denhardt's reagent, 0.5% SDS and 100 mg/ml of denatured fragmented salmon sperm DNA at 68° C.; and washes in 2×SSC and 0.5% SDS at room temperature for 10 min; in 2×SSC and 0.1% SDS at room temperature for 10 min; and in 0.1×SSC and 0.5% SDS at 65° C. three times for 5 minutes.

As another aspect, the present disclosure provides a method of treating seizure in a subject having above-normal levels of at least one alkaline phosphatase substrate, comprising administering a therapeutically effective amount of at least one recombinant alkaline phosphatase to said subject, wherein the at least one recombinant alkaline phosphatase comprises a structure of sALP-Fc-D10. In one embodiment, such at least one recombinant alkaline phosphatase comprises an amino acid sequence having at least 70%, 75%, 80%, 85%, 90%, 95%, 96%, 97%, 98%, 99%, or higher sequence identity with SEQ ID NO: 2. In another embodiment, such at least one recombinant alkaline phosphatase of the present disclosure is encoded by a polynucleotide molecule encoding a polypeptide comprising an amino acid sequence having at least 70%, 75%, 80%, 85%, 90%, 95%, 96%, 97%, 98%, 99%, or higher sequence identity with SEQ ID NO: 2. In another embodiment, the at least one recombinant alkaline phosphatase is encoded by a polynucleotide molecule which is hybridizable under high stringency conditions to at least one polynucleotide molecule encoding a polypeptide comprising an amino acid sequence having at least 90%, 95%, or higher sequence identity with SEQ ID NO: 2, wherein the high stringency conditions comprise: pre-hybridization and hybridization in 6×SSC, 5×Denhardt's reagent, 0.5% SDS and 100 mg/ml of denatured fragmented salmon sperm DNA at 68° C.; and washes in 2×SSC and 0.5% SDS at room temperature for 10 min; in 2×SSC and 0.1% SDS at room temperature for 10 min; and in 0.1×SSC and 0.5% SDS at 65° C. three times for 5 minutes.

As another aspect, the present disclosure provides a method of treating seizure in a subject comprising:

(i) identifying a population of subjects with aberrant alkaline phosphatase activities who suffer, or are at risk to suffer, from seizures; and (ii) administering a therapeutically effective amount of at least one recombinant alkaline phosphatase to a subject in the population, wherein the at least one recombinant alkaline phosphatase comprises a structure of sALP-Fc-D10. In one embodiment, such at least one recombinant alkaline phosphatase comprises an amino acid sequence having at least 70%, 75%, 80%, 85%, 90%, 95%, 96%, 97%, 98%, 99%, or higher sequence identity with SEQ ID NO: 2. In another embodiment, such at least one recombinant alkaline phosphatase of the present disclosure is encoded by a polynucleotide molecule encoding a polypeptide comprising an amino acid sequence having at least 70%, 75%, 80%, 85%, 90%, 95%, 96%, 97%, 98%, 99%, or higher sequence identity with SEQ ID NO: 2. In another embodiment, the at least one recombinant alkaline phosphatase is encoded by a polynucleotide molecule which is hybridizable under high stringency conditions to at least one polynucleotide molecule encoding a polypeptide comprising an amino acid sequence having at least 90%, 95%, or higher sequence identity with SEQ ID NO: 2, wherein the high stringency conditions comprise: pre-hybridization and hybridization in 6×SSC, 5×Denhardt's reagent, 0.5% SDS and 100 mg/ml of denatured fragmented salmon sperm DNA at 68° C.; and washes in 2×SSC and 0.5% SDS at room temperature for 10 min; in 2×SSC and 0.1% SDS at room temperature for 10 min; and in 0.1×SSC and 0.5% SDS at 65° C. three times for 5 minutes.

As another aspect, the present disclosure provides a method of treating seizure in a subject comprising:

(i) identifying a population of subjects with above-normal levels of at least one alkaline phosphatase substrate who suffer, or are at risk to suffer, from seizures; and (ii) administering a therapeutically effective amount of at least one recombinant alkaline phosphatase to a subject in the population, wherein the at least one recombinant alkaline phosphatase comprises a structure of sALP-Fc-D10. In one embodiment, such at least one recombinant alkaline phosphatase comprises an amino acid sequence having at least 70%, 75%, 80%, 85%, 90%, 95%, 96%, 97%, 98%, 99%, or higher sequence identity with SEQ ID NO: 2. In another embodiment, such at least one recombinant alkaline phosphatase of the present disclosure is encoded by a polynucleotide molecule encoding a polypeptide comprising an amino acid sequence having at least 70%, 75%, 80%, 85%, 90%, 95%, 96%, 97%, 98%, 99%, or higher sequence identity with SEQ ID NO: 2. In another embodiment, the at least one recombinant alkaline phosphatase is encoded by a polynucleotide molecule which is hybridizable under high stringency conditions to at least one polynucleotide molecule encoding a polypeptide comprising an amino acid sequence having at least 90%, 95%, or higher sequence identity with SEQ ID NO: 2, wherein the high stringency conditions comprise: pre-hybridization and hybridization in 6×SSC, 5×Denhardt's reagent, 0.5% SDS and 100 mg/ml of denatured fragmented salmon sperm DNA at 68° C.; and washes in 2×SSC and 0.5% SDS at room temperature for 10 min; in 2×SSC and 0.1% SDS at room temperature for 10 min; and in 0.1×SSC and 0.5% SDS at 65° C. three times for 5 minutes.

In some embodiments, the subject(s) described herein is a human or non-human mammal. In one embodiment, the subject(s) is a human.

BRIEF DESCRIPTION OF DRAWINGS

FIG. 1 presents the design and schematic structure of the recombinant ALP of the present disclosure exemplified by human soluble TNALP fusion protein hsTNALP-FcD10. Panel A presents a schematic representation of the complete primary translation product of the human tissue non-specific alkaline phosphatase gene (TNALP) including the N-terminal signal peptide and the transient membrane-anchored signal for GPI-addition. Panel B presents the primary translation product of the fusion protein. Panel C presents the primary translation product lacking the cleavable TNALP signal peptide;

FIG. 2 presents the protein sequence for hsTNALP-FcD10 with the N-terminal peptide signal (SEQ ID NO: 1). In this sequence, the 17-aa N-terminal peptide signal is shown italicized and underlined. The hsTNALP portion (SEQ ID NO: 2) is italicized but not underlined. The Fc portion (SEQ ID NO: 3) is underlined but not italicized. Asparagine (N) residues corresponding to putative N-glycosylation sites are labeled in bold and lower-case letters. Bold letters in upper-case (i.e., LK & DI) correspond to linkers between the hsTNALP portion and the Fc portion and between the Fc portion and the C-terminal D10, respectively. These linkers are derived from endonuclease restriction sites introduced during cDNA engineering.

FIG. 3 presents the protein sequence for the hsTNALP-FcD10 without the N-terminal peptide signal (SEQ ID NO: 4). The hsTNALP portion (SEQ ID NO: 2) is italicized but not underlined. The Fc portion (SEQ ID NO: 3) is underlined but not italicized. Asparagine (N) residues corresponding to putative N-glycosylation sites are labeled in bold and lower-case letters. Bold letters in upper-case (i.e., LK & DI) correspond to linkers between the hsTNALP portion and the Fc portion and between the Fc portion and the C-terminal D10, respectively.

FIG. 5 presents a summary of phenotype distribution among different colonies of $Akp2^{-/-}$ homozygous mice (using radiographic image scoring).

DETAILED DESCRIPTION

Figure 4:
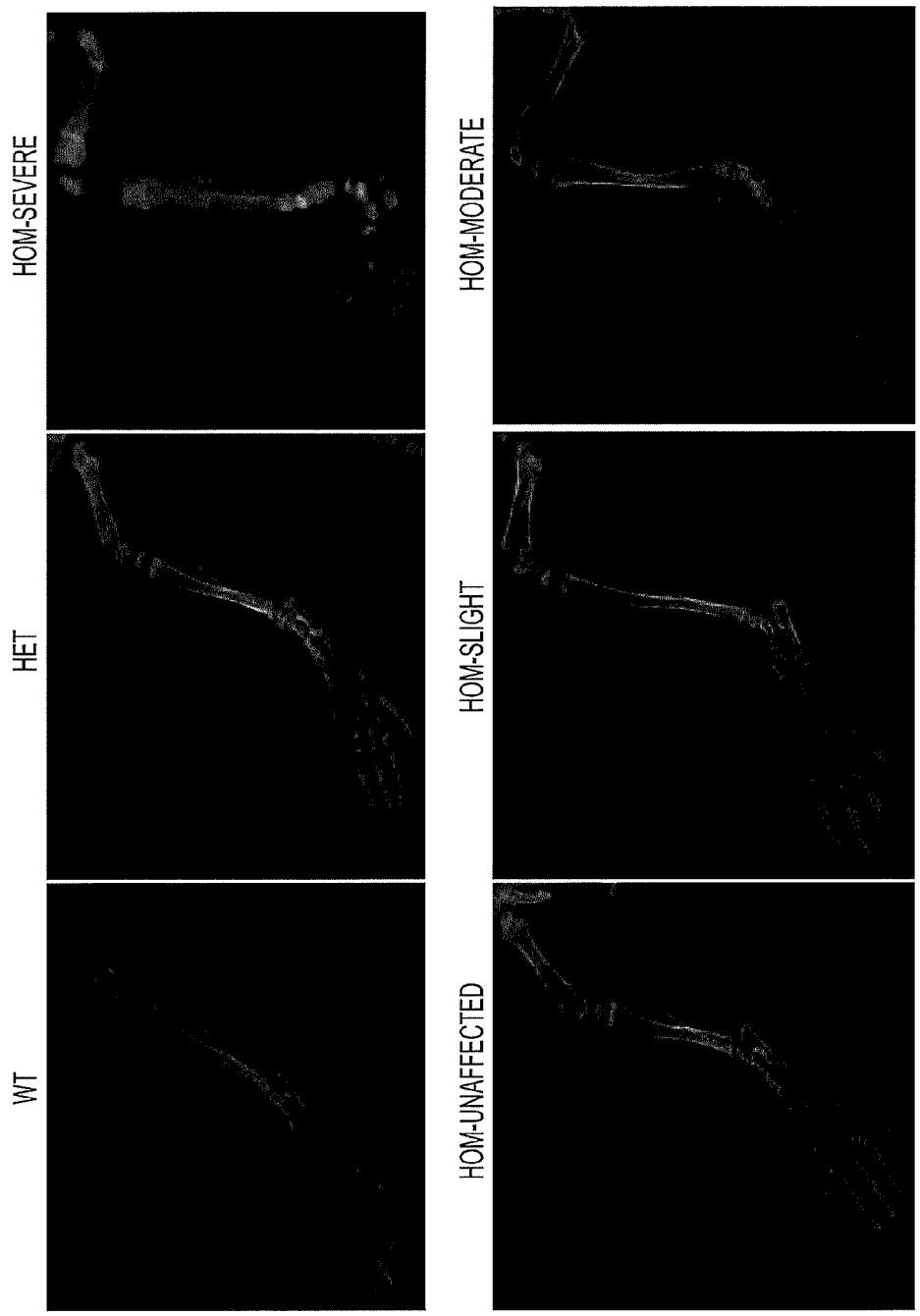
FIG. 4 presents X-ray images showing mineralization of leg bones from wild-type mice (WT), $Akp2^{+/-}$ heterozygous mice (HET), and $Akp2^{-/-}$ homozygous mice (HOM). Different degrees of mineralization defects (from having severe to unaffected phenotypes) were found among $Akp2^{-/-}$ homozygous mice.

Many HPP patients have seizures as additional symptoms to their characteristic mineralization defect. The Akp2$^{-/-}$ mice also develop seizures which are subsequently fatal. See Waymire et al. 1995 *Nature Genetics* 11:45-51. As vitamin B6 (pyridoxine) is a traditional treatment for seizures, many HPP patients having seizures are treated with vitamin B6 as a prophylactic therapy. However, some HPP patients are not responsive to pyridoxine treatment. Even for those pyridoxine-responsive HPP patients, high doses of vitamin B6 can, over time, be toxic, and may result in nerve damage or numbness and tingling in the extremities that may eventually be irreversible. The most common vitamin B6 toxicity symptoms include, for example, headache, severe fatigue, mood change, nerve change, etc. According to the safety publication on vitamin B6 (pyridoxine) by Mayo Clinic Health System on its website (www.mayoclinic.org/drugs-supplements/vitamin-b6/safety/hrb-20058788), excess vitamin B6 may cause abnormal heart rhythms, acne, allergic reactions, breast enlargement or soreness, changes in folic acid levels, decreased muscle tone, drowsiness or sedation, feeling of a lump in the throat, feeling of tingling on the skin, headache, heartburn, loss of appetite, nausea, rash, recurrence of ulcerative colitis (an inflammatory bowel disorder), stomach discomfort or pain, sun sensitivity, vomiting, worsened asthma, low blood pressure, blood sugar level change, and increased risk of bleeding. Vitamin B6 may also interfere with other medicine treatments. For example, it can reduce the effectiveness of levodopa therapy, which is used to treat Parkinson's disease. People taking penicillamine, used to treat Wilson disease, lead poisoning, kidney stones and arthritis, should take vitamin B6 only under a physician's direct supervision. Estrogenic herbs and supplements, including birth control pills, may interact with vitamin B6.

The present disclosure provides a method of identifying a population of subjects who have aberrant (e.g., deficient) alkaline phosphatase (ALP) activity (e.g., have defective allele(s) of the ALPL gene in humans or of the Akp2 (the ortholog of ALPL) gene in mice) or aberrant gene and/or protein levels of ALP substrates (e.g., PPi, PEA, and PLP). As used herein, the term "aberrant" means the expression levels and/or the enzymatic activity of a protein (e.g., an ALP), or its biologically active fusions or fragments thereof, deviates from the normal, proper, or expected course. For example, a subject (e.g., a human or a non-human animal, including but not limited to a mouse) with an "aberrant" ALP activity means such subject has an abnormal ALP activity, which may be due to, e.g., deficient or lack of an ALP gene or protein product and/or defective or loss-of-function of an ALP gene or protein product, relative to the level of expression and/or activity of such ALP protein from a healthy subject or a subject without a HPP symptom or a disease or disorder state characterized by aberrant protein levels and/or activity of at least one of ALP substrates (e.g., PPi, PLP, and PEA). In particular, the protein expression levels or activity of an ALP is deficient, lack of, or defective when such expression levels or activity is lower (such as, less than 95%, 90%, 85%, 80%, 75%, 70%, 65%, 60%, 55%, 50%, 45%, 40%, 35%, 30%, 25%, 20%, 15%, 10%, 5%, 1%, or lower) than the level of expression or activity of such ALP protein from a healthy subject or a subject without a HPP symptom or a disease or disorder state characterized by aberrant protein levels and/or activity of at least one of ALP substrates (e.g., PPi, PLP, and PEA). The population of subjects can be identified irrespective of whether they have previously been diagnosed with hypophosphatasia (HPP). The population is identified, for example, based on a reduced ALP activity due to, for example, lack or reduced levels of ALP protein(s) and/or defective ALP proteins with reduced or abolished enzymatic activity. Causes of reduced ALP activity include, for example, mutations in genes that encode ALPs, thereby leading to defective alleles of such genes, defects in signaling molecules that regulate the expression of ALPs, abnormal expression or regulation of co-factors, and/or aberrant expression of upstream or downstream factors that regulate the activity of ALPs. Particular alleles of ALPL can result in, for example, reduced alkaline phosphatase protein levels and/or protein function. Such alleles can be identified by methods known in the art. The members of the identified population should be monitored to determine disease progression (HPP) and other symptoms, e.g., seizures. Recombinant alkaline phosphatase, for example, can be supplied to the identified population to treat or prevent seizures and/or other symptoms, e.g., symptoms related to HPP or reduced ALP activity.

The terms "individual," "subject" and "patient" are used interchangeably and refer to any subject for whom diagnosis, treatment or therapy is desired, particularly humans. Other subjects may include, for example, cattle, dogs, cats, guinea pigs, rabbits, rats, mice, horses and the like. As used herein, an "at-risk" subject is a subject who is identified as having a risk of developing a disease, disorder or symptoms associated with, for example, aberrant ALP activity.

HPP patients are traditionally identified by their characteristic bone and/or teeth mineralization defects. However, HPP patients vary as to the degree of the mineralization defect, ranging from very severe to undetectable. Obviously, those HPP patients with minor or no mineralization defect are prone to misdiagnosis and delayed, if any, treatment with, for example, recombinant alkaline phosphatase. Described herein are materials and methods for identifying a subpopulation of HPP patients with minor, unaffected, or undetectable bone and/or tooth mineralization defects for alkaline phosphatase replacement treatment. Such patients may have been previously diagnosed with HPP but, due to their minor, unaffected, or undetectable mineralization defects, have not been treated with alkaline phosphatase. The present disclosure includes providing materials and methods for treating such subjects in the subpopulation with, for example, alkaline phosphatase or agent(s) that increase the activity of endogenous alkaline phosphatase. Such treatment may, for example, treat or prevent symptoms other than mineralization defects and/or prevent future mineralization defects due to disease progression.

Described herein are methods for identifying a population of ALP-defective subjects who either exhibit HPP and/or HPP-related symptoms, or who are at risk for developing HPP and/or HPP-related symptoms. The identified population can include subjects who have previously been identified as having HPP or HPP-related symptoms, or who are asymptomatic without a previous diagnosis. A diminished serum ALP activity leads to, for example, increased protein levels and/or functions of at least one of alkaline phosphatase substrates (e.g., pyrophosphate (PPi), pyridoxal 5'-phosphate (PLP) or phosphoethanolamine (PEA)). Methods for identifying the subject population include, for example, the detection of defective alkaline phosphatase alleles (either prenatal are after birth), measurement of in vivo protein expression levels or functional activity, measurement of associated marker analytes in a sample, or other methods known in the art for determining ALP activity.

The identified population with aberrant ALP activity can have symptoms other than bone and tooth mineralization defects. However, due to their minor or no mineralization defects, such subjects are less likely diagnosed as HPP subjects or treated with, for example, alkaline phosphatase. Described herein, therefore, are materials and methods for identifying and treating subjects who are at risk for developing a disease, disorder or symptoms associated with aberrant ALP activity, especially those who do not exhibit some common HPP symptoms (e.g., bone mineralization defects).

The present disclosure provides a subpopulation of alkaline phosphatase knockout ($Akp2^{-/-}$) mice which have minor, unaffected, or undetectable mineralization defects but still have a shortened life span. Studies on these mice indicated that alkaline phosphatase deficiency significantly reduced protein levels of gamma-aminobutyric acid (GABA), a chief inhibitory neurotransmitter in the mammalian central nervous system. The observed reduction in brain GABA was rescued by recombinant alkaline phosphatase treatments. Since a population of subjects has defective alkaline phosphatase but minimal or no mineralization defects, there is a population of subjects at risk for ALP-related disease(s), disorder(s) or symptoms, e.g., seizures, who are responsive to, for example, alkaline phosphatase replacement therapy or other therapies for increasing ALP activity.

Adding to the fact that HPP patients often exhibit seizures, described herein are data showing that, even in patients who do not exhibit some of the more dramatic HPP symptoms (e.g., bone mineralization defects), a reduced or abolished serum ALP activity leads to seizures. This population experiences or is at risk for experiencing seizures and other diseases, disorders or symptoms associated with reduced or abolished ALP activity (e.g., at risk for developing HPP or HPP symptoms).

Seizure or seizures in the present disclosure can be broadly classified as epileptic seizures, involving a brief episode of signs and/or symptoms due to abnormal excessive or synchronous neuronal activity in the brain, and non-epileptic seizures, which are paroxysmal events that mimic an epileptic seizure but do not involve abnormal, rhythmic discharges of cortical neurons. The outward effect of seizures can vary from uncontrolled jerking movement (tonic-clonic seizure (formerly known as grand mal seizures); sometimes referred to as "convulsions") to as subtle as a momentary loss of awareness (absence seizure). (Fisher et al., 2005 *Epilepsia* 46:470-2 and Ricker 2003 Differential Diagnosis in Adult Neuropsychological assessment. Springer Publishing Company. p. 109. ISBN 0-8261-1665-5). As used herein, "seizure" or "seizures" refers to any seizure or convulsion event due to any physiological or environmental causes, including, but not limited to, epileptic seizures, non-epileptic seizures, vitamin B6-responsive seizures, B6-non-responsive seizures, etc. The term "seizure" is often used interchangeably with "convulsion." Convulsions occur when a subject's body shakes rapidly and uncontrollably. During convulsions, the person's muscles contract and relax repeatedly. There are many different types of seizures. Some have mild symptoms without shaking.

Mice lacking alkaline phosphatase function (e.g., $Akp2^{-/-}$) develop seizures that are subsequently fatal (Waymire 1995). The seizures are caused by a defect in the metabolism of pyridoxal 5'-phosphate (PLP) by alkaline phosphatase, similar to that found in HPP patients. Generally, pyridoxine (vitamin B6) can be absorbed as three different vitamers: PLP, pyridoxamin-P, and pyridoxine-glucoside (Plecko 2009 *Can J Neural Sci* 36:S73-S77). However, in the liver the latter two will be converted into the only active cofactor PLP by pyridox(am)ine-5-phosphate oxidase (PNPO). PLP in blood circulation is then dephosphorylated by alkaline phosphatase into pyridoxal (PL), which freely crosses cell membrane and gets re-phosphorylated by pyridoxal kinase into intracellular PLP. PLP, once inside cells, is a cofactor of various enzymatic reactions in amino acid and neurotransmitter metabolism such as, for example, the conversion of glutamate into gamma-aminobutyric acid (GABA), the glycine cleavage system, dopamine, histamine, D-serine, hydrogen sulfide and the aromatic acid decarboxylase in serotonin and homovanillic acid synthesis. In $Akp2^{-/-}$ mice, due to the defective alkaline phosphatase, PL cannot be produced from PLP, resulting in elevated plasma PLP levels but reduced intracellular PLP concentrations. The lack of intracellular PLP shuts down downstream metabolism including, for example, the production of GABA by glutamate decarboxylase (GAD) in the brain.

GABA acts at inhibitory synapses in the brain of vertebrates by binding to specific transmembrane receptors in the plasma membrane of both pre- and postsynaptic neuronal processes. This binding causes the opening of ion channels to allow the flow of either negatively charged chloride ions into the cell or positively charged potassium ions out of the cell. This action results in a negative change in the transmembrane potential, usually causing hyperpolarization. Two general classes of GABA receptor are known: $GABA_A$ in which the receptor is part of a ligand-gated ion channel complex, and $GABA_B$ metabotropic receptors, which are G protein-coupled receptors that open or close ion channels via intermediaries. GABA levels were found to be reduced approximately 50% in $Akp2^{-/-}$ mice compared to control littermates, which contributes to a shortened life span for the knockout mice (Waymire 1995). Further, by supplementing vitamin B6 (pyridoxal, or PL, but not PN), the seizure phenotype was rescued in about 67% of the $Akp2^{-/-}$ mice with a hybrid genetic background, although the rescued animals subsequently developed defective dentition. The remaining 33% responded poorly to PL injections or were nonresponsive. On the contrary, $Akp2^{-/-}$ mice with an inbred genetic background are all poor responders or even nonresponsive to PL supplement.

Alkaline Phosphatases (ALPs)

There are four known isozymes of ALP, namely tissue non-specific alkaline phosphatase (TNALP, see discussion below), placental alkaline phosphatase (PALP) (NCBI Reference Sequences [NP_112603] and [NP_001623]), germ cell alkaline phosphatase (GCALP) (NCBI Reference Sequence [P10696]) and intestinal alkaline phosphatase (IALP) (NCBI Reference Sequence [NP_001622]). These enzymes possess very similar three-dimensional structures. Each of their catalytic sites contains four metal binding domains for metal ions (two $Zn^{2+}$ and one $Mg^{2+}$) necessary for enzymatic activity. These enzymes catalyze the hydrolysis of monoesters of phosphoric acid and also catalyze a transphosphorylation reaction in the presence of high concentrations of phosphate acceptors. For example, PALP is physiologically active toward PEA, PPi and PLP, which are known natural substrates for TNALP (Whyte, 1995; Zhang, 2004).

Based on the structural similarity among ALPs, one would expect some functional overlaps over them as well. Human and rodents fed a diet with a high fat content, for example, had elevated levels of circulating ALPs originated from IALP (Langman 1966 and Gould 1944 *Biochem.* 4:175-181). Thus, increasing the dietary intake may elevate IALP and thus compensate for TNALP function by reducing circulating PLP in $Akp2^{-/-}$ mice. Similarly, PALP expressed in human female carriers of HPP during pregnancy showed compensation for TNALP (Whyte 1995 *J. Clin. Invest.* 95:1440-1445).

Identification of a population of subjects with reduced or abolished ALP activity can be subsequently treated, for example, with a therapeutically effective amount of recombinant TNALP or other ALP isozymes. Different isozymes can be administered alone interchangeably or in combination. Identified subjects can be treated, for example, by recombinant TNALP, PALP, IALP and/or GCALP. These ALPs can be mammalian (such as human) proteins, non-mammalian proteins, or fusion proteins comprising at least part of mammalian portions.

TNALP and Variants

TNALP is a membrane-bound protein anchored through a glycolipid to its C-terminal (Swiss-Prot, P05186). This glycophosphotidylinositol (GPI) anchor is added post-translationally after removal of a hydrophobic C-terminal end, which serves both as a temporary membrane anchor and as a signal for the addition of the GPI. The recombinant TNALP described herein includes, for example, the soluble portion of TNALP. A more specific example includes a recombinant TNALP that comprises a human TNALP wherein the first amino acid of the hydrophobic C-terminal sequence, namely alanine, is replaced by a stop codon. The soluble TNALP (herein called sTNALP) so formed contains all amino acids of the native anchored form of TNALP necessary for the formation of the catalytic site but lacks the GPI membrane anchor. Known TNALPs include, for example, human TNALP [NCBI Reference Sequences NP_000469, AAI10910, AAH90861, AAH66116, AAH21289, and AAI26166]; rhesus TNALP [XP_001109717]; rat TNALP [NP_037191]; dog TNALP [AAF64516]; pig TNALP [AAN64273], mouse [NP_031457], bovine [NP_789828, NP_776412, AAM 8209, AAC33858], and cat [NP_001036028]. The term "wild-type" or "wild-type sequence" used for TNALP or other genes or proteins in the instant disclosure refers to the typical form of such genes or proteins as it occurs in nature in normal human, non-human mammals, or other living organisms. A wild-type sequence may refer to the standard "normal" allele at a locus for a gene or the standard "normal" primary amino acid sequence (optionally with the standard "normal" post-translational modifications to and/or inter-chain bonds and/or interactions among amino acid residues) for a polypeptide or protein, in contrast to that produced by a non-standard, "mutant" allele or amino acid sequence/modification/interaction. "Mutant" alleles can vary to a great extent, and even become the wild type if a genetic shift occurs within the population. It is now appreciated that most or all gene loci (and less frequently but still possible for most polypeptide sequences) exist in a variety of allelic forms, which vary in frequency throughout the geographic range of a species, and that a uniform wild type may not necessarily exist. In general, however, the most prevalent allele or amino acid sequence—i.e., the one with the highest frequency among normal individual human or other organisms—is the one deemed as wild type in the instant disclosure. The term "normal" used for human or other organisms in this specification refers to, except for specified otherwise, a human or other organisms without any diseases (e.g., HPP), disorders, and/or symptoms or physiological consequences (e.g., mineralization defects, seizures, etc.) caused by or related to the aberrant activity (which may be due to, e.g., deficient or lack of gene or protein product and/or defective or loss-of-function of gene or protein product) of the relevant gene or polypeptide/protein. The most obvious example for a normal human is a human being who has no HPP or HPP symptoms and has no mutations or modifications to ALPL gene and ALP proteins which may result in HPP-related symptoms. In another scenario focusing on ALP functions, the scope of a "normal" human in the present disclosure may be broadened to include any human beings having no aberrant endogenous alkaline phosphatase activity (which may be tested by, e.g., the substrate (PPi, PEA and PLP) levels and compared to the corresponding activity in other healthy or normal human beings).

Recombinant TNALPs described herein can include sequences that are substituted, either at the nucleotide or amino acid level, by sequences at one or more positions of the TNALP sequence, at two or more positions of the TNALP sequence, at 3 or more positions of the TNALP sequence, at 5 or more positions of the TNALP sequence, at 10 or more positions of the TNALP sequence, or at 15-20 or more positions of the TNALP sequence. Substitutions can include, for example, conservative substitutions, replacement by orthologous sequences, and/or disruptive substitutions. TNALP sequences can also have deletions or rearrangements.

One of skill in the art will recognize that conservative substitutions can be made at the nucleotide level to coding sequences that result in functional expression products. As such, the TNALP sequence and fragments (optionally including exons and regulatory sequences) can be wild-type sequences of TNALP, or they can be variant sequences that share a high homology with wild-type sequences. The disclosure provides for the use of sequences that at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% or above identity to desired wild-type sequences. As used herein, the term "about" means plus or minus 10% of the numerical value of the number with which it is being used.

The terms "homology" or "identity" or "similarity" refer to sequence relationships between two sequences and can be determined by comparing a nucleotide position or amino acid position in each sequence when aligned for purposes of comparison. The term "homology" refers to the relatedness of two nucleic acid or amino acid sequences. The term "identity" refers to the degree to which the compared sequences are the same. The term "similarity" refers to the degree to which the two sequences are the same, but includes neutral degenerate nucleotides that can be substituted within a codon without changing the amino acid identity of the codon.

One of ordinary skill in the art will recognize that individual substitutions, deletions or additions to a nucleic acid, peptide, polypeptide or protein sequences that alter, add or delete a single amino acid or a small percentage of amino acids in the encoded sequence is a "conservatively modified variant." Such variants can be useful, for example, to alter the physical properties of the peptide, e.g., to increase stability or efficacy of the peptide. Conservative substitution tables providing functionally similar amino acids are known to those of ordinary skill in the art. Such conservatively modified variants are in addition to and do not exclude polymorphic variants, interspecies homologs and alternate alleles. The following groups provide non-limiting examples of amino acids that can be conservatively substituted for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M).

Without being limited by theory, recombinant ALP described herein encompasses sequences comprising a consensus sequence derived from the ALP extracellular domain of human ALP isozymes and of known functional ALPs (e.g., ALPs originated from human, non-human mammal, mouse, rat, cattle, cat, dog, pig, etc.). As used herein the terminology "extracellular domain" refers to any functional extracellular portion of the native protein (e.g., without the peptide signal). Recombinant sTNALP retaining original amino acids 1 to 501 (18 to 501 when counting the secreting signal peptide) (Oda et al., *J. Biochem* 126: 694-699, 1999), amino acids 1 to 504 (18 to 504 when secreted) (Bernd et al., U.S. Pat. No. 6,905,689) and amino acids 1 to 505 (18-505 when secreted) (Tomatsu et al., US 2007/0081984), are enzymatically active. Further, a recombinant sTNALP retaining amino acids 1 to 502 (18 to 502 when secreted) (FIG. 3) of the original TNALP is enzymatically active (see PCT publication no. WO 2008/138131). This indicates that amino acid residues can be removed from the C-terminal end of native alkaline phosphatases without affecting their enzymatic activity. Moreover, the present disclosure also includes any ALP variants containing at least one substitution, deletion, addition, and/or modification (e.g., glycosylation, PEGylation, glutathionylation, ubiquitination, sialylation acetylation, amidation, blockage, formylation, gamma carboxyglutamic acid hydroxylation, methylation, phosphorylation, pyrrolidone carboxylic acid and/or sulfatation) to amino acid residues of wild-type ALP. Such variants, to be useful for the present disclosure, need only retain some degree (e.g., more than or about 30%, about 40%, about 50%, about 60%, about 70%, about 80%, about 90%, about 100%, about 150%, about 200%, about 300%, or more) of in vitro and/or in vivo activity compared to wild-type ALP.

Fusion Proteins Comprising ALP

The methods described herein can utilize a recombinant ALP (e.g., TNALP) fusion protein for the treatment of the identified subject population(s). Fusion proteins may comprise the full length or fragments of ALP or variants disclosed herein and maintain biological activity. Without being limited by theory, fusion proteins may comprise other portions, such as any polypeptides, lipids, nucleotides, or other moieties, to maintain or improve, for example, alkaline phosphatase functions. For example, fusion proteins may comprise a fragment crystallizable region (Fc) or other full-length or fragments of immunoglobulins to increase the stability or retention time (e.g., with a longer half-life) of ALP in vivo. Similarly, albumin fusion technology may be used to improve the half-life of circulating ALP (Schulte 2011 *Thromb Res.* 128:S9-12). Furthermore, fusion proteins may comprise a targeting portion to direct ALP to specific tissue, organ or cells.

The present disclosure also encompasses fusion proteins comprising post-translationally modified ALP proteins or fragments thereof, which are modified by, e.g., glycosylation, PEGylation, glutathionylation, ubiquitination, sialylation acetylation, amidation, blockage, formylation, gamma-carboxyglutamic acid hydroxylation, methylation, phosphorylation, pyrrolidone carboxylic acid and/or sulfatation.

The term "recombinant protein" or "recombinant polypeptide" refers to a protein encoded by a genetically manipulated nucleic acid. The nucleic acid is generally placed within a vector, such as a plasmid or virus, as appropriate for a host cell. Although Chinese Hamster Ovary (CHO) cells have been used as a host for expressing some of the recombinant proteins described herein, a person of ordinary skill in the art will understand that a number of other hosts and expression systems, e.g., modified CHO cells including, but not limited to CHO-DG44 and CHO/dhfr− (also referred to as CHO duk−), HEK293 cells, PerCβ, baby hamster kidney (BHK) cells, bacterial cells, in vitro systems, L cells, C127 cells, 3T3 cells, COS-7 cells, etc., may be used to produce recombinant proteins. "Recombinant cleavable" protein or polypeptide refers to a recombinant protein that can be cleaved by a host cell enzyme so as to produce a modified activity, e.g., rendering the recombinant protein or polypeptide into a secreted or soluble protein.

Fragment Crystallizable Region (Fc) Fragments

Useful Fc fragments for the present disclosure include Fc fragments of IgG that comprise the hinge, the $CH_2$ and $CH_3$ domains. IgG-1, IgG-2, IgG-3, IgG-3 and IgG-4 for instance can be used. An exemplary amino acid sequence for the Fc fragment used in a fusion protein with ALP in the present disclosure is listed in SEQ ID NO: 3. Similarly, other amino acid sequences for the Fc fragment, such as an amino acid sequence having at least 70%, 75%, 80%, 85%, 90%, 95%, 96%, 97%, 98%, 99%, or higher sequence identity with SEQ ID NO: 3, are also included in the present disclosure.

Negatively Charged Peptides

The ALP fusion proteins of the present disclosure may comprise a bone-targeting polypeptide, such as, for example, a negatively charged peptide. The negatively charged peptide may be a poly-aspartate or poly-glutamate selected from the group consisting of D10, D8, D11, D12, D13, D14, D15, D16, E10, E8, E11, E12, E13, E14, E15, and E16, or any other formats known in the art, e.g., as described in PCT publication no. WO 2008/138131.

Formation of Fusion Proteins

The present disclosure provides a recombinant ALP construct or an ALP fusion protein for treating identified subject populations and subpopulations, e.g., of HPP patients. Such recombinant ALP construct or fusion protein can comprise a full-length or fragment of a soluble ALP (sALP, e.g., sTNALP) isoenzyme and an Fc fragment, further with or without a negatively charged peptide. These components can be fused together in any sequence from the 5' terminus to the 3' terminus, provided the resulting fusion protein maintains or improves alkaline phosphatase activity. Exemplary formats of fusion proteins include, without limiting, sALP-Fc-D10, sALP-Fc, D10-Fc-sALP, Fc-sALP, D10-sALP-Fc. Fc-sALP-D10, Fc-D10-sALP, etc. In these formats, D10 can be optionally substituted by any other negatively charged peptide or targeting moiety, and the Fc fragment can be substituted by any functional IgG or immunoglobulin.

The present disclosure provides a method of treating seizures with recombinant ALP constructs, including sALP with or without Fc fusion and/or negatively charged peptide tags. While it is well known in the art that negatively charged peptide tags (such as D10) can target ALP to bone tissues (see, e.g., PCT publication no. WO 2008/138131), it's surprising that a bone-targeted sALP-Fc-D10 construct (a.k.a., asfotase alfa) functions well to improve Akp2$^{-/-}$ mice survival and ameliorate seizure-related physiological parameters, such as restoring GABA and serine levels and decreasing cystathionine levels in brain.

Spacer

Different components (e.g., fragments or portions) of an ALP fusion protein can be fused together through a separating linker or spacer. In some embodiments the spacer can be a short polypeptide comprising at least 2, 3, 4, 5, 6, 7, 8, 9, 10 or more amino acids. In one embodiment, the Fc fragment in the sALP (e.g., sTNALP) fusion protein acts as a spacer that allows the protein to be more efficiently folded. This was confirmed by the discovery that expression of sTNALP-Fc-D10 was higher than that of sTNALP-D10 (Example 2 of PCT publication no. WO 2008/138131). While not being limited by theory, the Fc fragment could act to alleviate the repulsive forces caused by the presence of the highly negative charges the D10 sequence adds at the C-terminus of the sALP sequence. Other useful spacers include, but are not limited to, polypeptides able to alleviate the repulsive forces caused by the presence of the highly negatively charged sequence (e.g., poly-aspartate such as D10) added to the sALP sequence.

The spacer can be designed to, for example, alleviate steric hindrance that could impede the interaction of two sALP domains from two sALP monomers. Furthermore, a spacer may be introduced between the sALP portion and the Fc portion if needed, e.g., the sTNALP-Fc-D10 constructs as illustrated in FIGS. 2 and 3 have spacers between the sTNALP. The Fc and D10 comprise two amino acids (LK and DI, respectively).

A bone targeted sALP (e.g., sTNALP-Fc-D10) can further optionally comprise one or more additional amino acids 1) downstream from the poly-aspartate or poly-glutamate; and/or 2) between the poly-aspartate and the Fc fragment; and/or 3) between the spacer such as the Fc fragment and the sALP fragment. This is the case, for example, when the cloning strategy used to produce the bone targeting conjugate introduces exogenous amino acids in these locations. The exogenous amino acids, however, should be selected so as not to provide an additional GPI anchoring signal. The likelihood of a designed sequence being cleaved by the transamidase of the host cell can be predicted as described by Ikezawa (Ikezawa 2002 *Biol Pharm. Bull.* 25(4):409-417).

Conditions suitable for sALP expression or its fusion protein can be optimized as would be recognized by one of skill in the art. Such conditions include the use of, for example, a culture medium that enables production of the sALP or its fusion protein. Such medium can be prepared with a buffer comprising, for example, bicarbonate and/or HEPES; ions including, for example, chloride, phosphate, calcium, sodium, potassium and/or magnesium; iron; carbon sources including, for example, simple sugars and/or amino acids; lipids, nucleotides, vitamins and/or growth factors including, for example, insulin. Commercially available media like alpha-MEM, DMEM, Ham's-F12 and IMDM supplemented with 2-4 mM L-glutamine and 5% Fetal bovine serum can be used. Commercially available animal protein-free media like, for example, Hyclone™ SFM4CHO, Sigma CHO DHFR⁻, Cambrex POWER™ CHO CD supplemented with 2-4 mM L-glutamine can be used. These media are desirably prepared without thymidine, hypoxanthine and L-glycine to maintain selective pressure allowing stable protein product expression.

The term "bone tissue" is used herein to refer to tissue synthesized by osteoblasts composed of an organic matrix containing mostly collagen and mineralized by the deposition of hydroxyapatite crystals.

The fusion proteins comprised in the bone delivery conjugates of the present disclosure are useful for therapeutic treatment of bone defective conditions by providing an effective amount of the fusion protein to the bone. The fusion proteins are provided in the form of pharmaceutical compositions in any standard pharmaceutically acceptable carriers, and are administered by any standard procedure, for example by intravenous injection.

As used herein the terminology "HPP phenotype" is meant to generally, if not specified otherwise, refer to any characteristic phenotype of subjects having HPP, such as, but not limited to, any phenotype related to bone or teeth mineralization defects. HPP phenotypes can also include "HPP symptoms" in addition to bone mineralization defects including, but not limited to, for example, rickets (defect in growth plate cartilage), osteomalacia, elevated blood and/or urine levels of inorganic PPi, PEA, or PLP, seizure, bone pains, calcium pyrophosphate dihydrate crystal deposition (CPPD) in joints leading to chondrocalcinosis and premature death. Without being so limited, an HPP phenotype can be documented by growth retardation with a decrease of long bone length (such as, for example, femur, tibia, humerus, radius, ulna), a decrease of the mean density of total bone and a decrease of bone mineralization in bones such as, for example, femur, tibia, ribs and metatarsi, and phalange, a decrease in teeth mineralization, a premature loss of deciduous teeth (e.g., aplasia, hypoplasia or dysplasia of dental cementum). Without being so limited, correction or prevention of a bone mineralization defect may be observed by one or more of the following: an increase of long bone length, an increase of mineralization in bone and/or teeth, a correction of bowing of the legs, a reduction of bone pain and a reduction of CPPD crystal deposition in joints.

"A non-HPP subject" is meant to refer to any subject who 1) is not yet diagnosed to have HPP and has no HPP phenotype; 2) has been diagnosed to have no HPP; or 3) has no aberrant alkaline phosphatase activity.

"Treatment" refers to the administration of a therapeutic agent or the performance of medical procedures with respect to a patient or subject, for either prophylaxis (prevention) or to cure or reduce the symptoms of the infirmity or malady in the instance where the patient is afflicted. Prevention of a disease, disorder or symptoms associated with aberrant ALP activity is included within the scope of treatment. The methods and compositions described herein or identified through methods described herein can be used as part of a treatment regimen in therapeutically effective amounts. A "therapeutically effective amount" is an amount sufficient to decrease, prevent or ameliorate the symptoms associated with a medical condition.

Other Anti-Seizure Drugs

Conventional antiepileptic drugs may block sodium channels or enhance GABA function. In addition to voltage-gated sodium channels and components of the GABA system, other targets include $GABA_A$ receptors, the GAT-1 GABA transporter and GABA transaminase. Additional targets include voltage-gated calcium channels, SV2A and α2δ. Exemplary anti-seizure drugs include, for example, aldehydes (e.g., paraldehyde), aromatic allylic alcohols (e.g., stiripentol), barbiturates (e.g., phenobarbital, methylphenobarbital and barbexaclone), benzodiazepines (e.g., clobazam, clonazepam, clorazepate, diazepam, midazolam, lorazepam, nitrazepam, temazepam and nimetazepam), bromides (e.g., potassium bromide), carbamates (e.g., felbamate), carboxamides (e.g., carbamazepine, oxcarbazepine and eslicarbazepine acetate), fatty acids (e.g., valproates, vigabatrin, progabide and tiagabine), fructose derivatives (e.g., topiramate), GABA analogs (e.g., gabapentin and pregabalin), hydantoins (e.g., ethotoin, phenytoin, mephenytoin and fosphenytoin), oxazolidinediones (e.g., paramethadione, trimethadione and ethadione), propionates (e.g., beclamide), pyrimidinediones (e.g., primidone), pyrrolines (e.g., brivaracetam, levetiracetam, and seletracetam), succinimides (e.g., ethosuximide, phensuximide and mesuximide), suflonamides (e.g., acetazolamide, sultiame, methazolamide and zonisamide), triazines (e.g., lamotrigine), ureas (e.g., pheneturide and phenacemide), valproylamides (amide derivatives of valproate) (e.g., valpromide and valnoctamide), and others (e.g., perampanel).

At least one of the conventional anti-seizure drugs can be is co-administered together with one or more recombinant ALPs described herein to a subject to treat or alleviate seizure symptoms. In particular, such combination therapy (ies) can be used to treat subjects suffering from vitamin B6-resistant seizures, and they can be used to treat a population identified as described herein whose subjects exhibit reduced ALP activity irrespective of whether they have other HPP-like symptoms. Such conventional anti-seizure drugs may be administered with the recombinant ALP at the same time (for a pre-determined period of time), or prior to or post ALP administration.

Route of Administration

Therapeutic agents described herein, e.g., recombinant ALPs, can be administered, for example, orally, nasally, intravenously, intramuscularly, subcutaneously, sublingually, intrathecally or intradermally. The route of administration can depend on a variety of factors, such as the environment and therapeutic goals.

By way of example, pharmaceutical composition of the present disclosure can be in the form of a liquid, solution, suspension, pill, capsule, tablet, gelcap, powder, gel, ointment, cream, nebulae, mist, atomized vapor, aerosol, or phytosome. Dietary supplements as disclosed herein can contain pharmaceutically acceptable additives such as suspending agents, emulsifying agents, non-aqueous vehicles, preservatives, buffer salts, flavoring, coloring and sweetening agents as appropriate. Preparations for oral administration also can be suitably formulated to give controlled release of the active ingredients.

Dosage

The specific dosages will depend on many factors including the mode of administration and the age and weight of the subject. Typically, the amount of bone targeted or untagged ALP contained within a single dose is an amount that effectively prevent, delay or correct seizures without inducing significant toxicity. Typically, sALPs or its fusion protein in accordance with the present disclosure can be administered to subjects in doses ranging from 0.001 to 500 mg/kg/day and, in a more specific embodiment, about 0.1 to about 100 mg/kg/day, and, in a more specific embodiment, about 0.2 to about 20 mg/kg/day. The allometric scaling method (Mahmood et al. 2003 *Clin. Pharmacol.*, 43(7):692-7 and Mahmood 2009 *J. Pharma. Sci.*, 98(10):3850-3861) can be used to extrapolate the dose from mice to human. The dosage can be adapted by the clinician in accordance with conventional factors such as the extent of the disease and different parameters from the patient.

The therapeutically effective amount of sALP or its fusion protein may also be measured directly. The effective amount may be given daily or weekly or fractions thereof. Typically, a pharmaceutical composition disclosed herein can be administered in an amount from about 0.001 mg up to about 500 mg per kg of body weight per day (e.g., 0.05, 0.01, 0.1, 0.2, 0.3, 0.5, 0.7, 0.8, 1 mg, 2 mg, 3 mg, 4 mg, 5 mg, 8 mg, 10 mg, 15 mg, 16 mg, 20 mg, 30 mg, 50 mg, 100 mg or 250 mg). Dosages may be provided in either a single or multiple dosage regimens. For example, in some embodiments the effective amount of the sALP or its fusion protein is a dose that ranges from about 0.1 to about 100 mg/kg/day, from about 0.2 mg to about 20 mg per day, from about 1 mg to about 5 mg per day, from about 1 mg to about 6 mg per day, from about 1 mg to about 7 mg per day, from about 1 mg to about 8 mg per day, from about 1 mg to about 10 mg per day, from about 0.7 mg to about 210 mg per week, from about 1.4 mg to about 140 mg per week, from about 0.3 mg to about 300 mg every three days, from about 0.4 mg to about 40 mg every other day, and from about 2 mg to about 20 mg every other day.

These are simply guidelines since the actual dose must be carefully selected and titrated by the attending physician based upon clinical factors unique to each patient or by a nutritionist. The optimal daily dose will be determined by methods known in the art and will be influenced by factors such as the age of the patient as indicated above and other clinically relevant factors. In addition, patients may be taking medications for other diseases or conditions. The other medications may be continued during the time that sALP or its fusion protein is given to the patient, but it is particularly advisable in such cases to begin with low doses to determine if adverse side effects are experienced.

Carriers/Vehicles

Preparations containing sALP or its fusion protein may be provided to patients in combination with pharmaceutically acceptable sterile aqueous or non-aqueous solvents, suspensions or emulsions. Examples of nonaqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringer's dextrose solution, dextrose plus sodium chloride solution, Ringer's solution containing lactose, or fixed oils. Intravenous vehicles may include fluid and nutrient replenishers, electrolyte replenishers, such as those based upon Ringer's dextrose, and the like.

The pharmaceutical compositions described herein can be delivered in a controlled release system. In one embodiment polymeric materials including polylactic acid, polyorthoesters, cross-linked amphipathic block copolymers and hydrogels, polyhydroxy butyric acid and polydihydropyrans can be used (see also Smolen and Ball, *Controlled Drug Bioavailability, Drug product design and performance,* 1984, John Wiley & Sons; Ranade and Hollinger, *Drug Delivery Systems,* pharmacology and toxicology series, 2003, 2nd edition, CRRC Press), in another embodiment, a pump may be used (Saudek et al., 1989, *N. Engl. J. Med.* 321: 574).

The therapeutic agents of the present disclosure could be in the form of a lyophilized powder using appropriate excipient solutions (e.g., sucrose) as diluents.

Further, the nucleotide segments or proteins according to the present disclosure can be introduced into individuals in a number of ways. For example, osteoblasts can be isolated from the afflicted individual, transformed with a nucleotide construct disclosed herein and reintroduced to the afflicted individual in a number of ways, including intravenous injection. Alternatively, the nucleotide construct can be administered directly to the afflicted individual, for example, by injection. The nucleotide construct can also be delivered through a vehicle such as a liposome, which can be designed to be targeted to a specific cell type, and engineered to be administered through different routes.

The fusion proteins of the present disclosure could also be advantageously delivered through gene therapy. Useful gene therapy methods include those described in PCT publication no. WO 2006/060641, U.S. Pat. No. 7,179,903 and PCT publication no. WO 2001/036620 using, for example, an adenovirus vector for the therapeutic protein and targeting hepatocytes as protein producing cells.

A "gene delivery vehicle" is defined as any molecule that can carry inserted polynucleotides into a host cell. Examples of gene delivery vehicles are liposomes, biocompatible polymers, including natural polymers and synthetic polymers; lipoproteins; polypeptides; polysaccharides; lipopolysaccharides; artificial viral envelopes; metal particles; and bacteria, or viruses, such as baculovirus, adenovirus and retrovirus, bacteriophage, cosmid, plasmid, fungal vectors and other recombination vehicles typically used in the art that have been described for expression in a variety of eukaryotic and prokaryotic hosts, and may be used for gene therapy as well as for simple protein expression. "Gene delivery," "gene transfer," and the like as used herein, are terms referring to the introduction of an exogenous polynucleotide (sometimes referred to as a "transgene") into a host cell, irrespective of the method used for the introduction. Such methods include a variety of techniques such as, for example, vector-mediated gene transfer (e.g., viral infection/transfection, or various other protein-based or lipid-based gene delivery complexes) as well as techniques facilitating the delivery of "naked" polynucleotides (such as electroporation, "gene gun" delivery and various other techniques used for the introduction of polynucleotides).

The introduced polynucleotide may be stably or transiently maintained in the host cell. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are capable of mediating transfer of genes to mammalian cells.

A "viral vector" is defined as a recombinantly produced virus or viral; particle that comprises a polynucleotide to be delivered into a host cell. Examples of viral vectors include retroviral vectors, adenovirus vectors, adeno-associated virus vectors (e.g., see PCT publication no. WO 2006/002203), alphavirus vectors and the like.

In aspects where gene transfer is mediated by a DNA viral vector, such as an adenovirus (Ad) or adeno-associated virus (MV), a vector construct refers to the polynucleotide comprising the viral genome or part thereof, and a transgene. Ads are a relatively well characterized, homogenous group of viruses, including over 50 serotypes (WO 95/27071). Ads are easy to grow and do not require integration into the host cell genome. Recombinant Ad derived vectors, particularly those that reduce the potential for recombination and generation of wild-type virus, have also been constructed (WO 95/00655 and WO 95/11984). Vectors that contain both a promoter and a cloning site into which a polynucleotide can be operatively linked are known in the art. Such vectors are capable of transcribing RNA in vitro or in vivo. To optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation.

The sALP or its fusion protein of the present disclosure may also be used in combination with at least one other active ingredient to correct a bone mineralization defect or another detrimental symptom of HPP, e.g., seizures. It may also be used in combination with at least one with at least one other active ingredient to correct cementum defect.

Kits

The present disclosure also relates to a kit for identifying a population of subjects who exhibit reduced ALP activity and/or for treating the identified population. The kit, for example, can identify subjects who do not exhibit bone mineralization defects, and can include, for example, therapeutic agents and formulations for treating seizures (e.g., B6-resistant seizures treated, for example, by a recombinant ALP, e.g., a recombinant TNALP). The kit can further comprise instructions to administer the composition or vector to a subject to correct or prevent a disease, disorder or symptoms associated with reduced ALP activity, e.g., HPP and HPP-associated symptoms.

Such kits may further comprise at least one other active agent able to prevent or correct a phenotype of the subject (such as other anti-seizure drugs).

In addition, a compartmentalized kit in accordance with the present disclosure includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another.

All references cited herein are incorporated herein by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supersede and/or take precedence over any such contradictory material.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

EXAMPLES

Example 1 Expression and Purification of Recombinant sTNALP-FcD10

In order to facilitate the expression and purification of recombinant TNALP, the hydrophobic C-terminal sequence that specifies GPI-anchor attachment in TNALP was eliminated to make it a soluble secreted enzyme (Di Mauro et al. 2002 *Journal of Bone and Mineral Research* 17:1383-1391). The coding sequence of the TNALP ectodomain was also extended with the Fc region of the human IgG1 ($\gamma 1$) (Swiss-Prot P01857). This allowed rapid purification of the recombinant enzyme on Protein A chromatography and surprisingly, its increased expression. Furthermore, to target the recombinant TNALP to bone tissue, a deca-aspartate (D10) sequence was attached to the C-terminal of the Fc region. This chimeric form of TNALP, designated sTNALP-FcD10, retains full enzymatic activity both when assayed at pH 9.8 using the artificial substrate p-nitrophenylphosphate and when assayed at pH 7.4 using inorganic pyrophosphate (PPi), as the physiological substrate. As in the naturally occurring form of TNALP the N-terminal signal peptide is cleaved off during the co-translational translocation of the protein across the rough endoplasmic reticulum. Its design and structure is schematically illustrated in FIG. 1. The amino acid sequence of the fusion protein (including the signal peptide) is shown in FIG. 2. The amino acid sequence of the fusion protein as secreted (i.e. without the signal peptide) is shown in FIG. 3. For a complete description of an expression process and characteristics of an exemplary sTNALP-FcD10 fusion protein, see, e.g., PCT Publication No. WO 2008/138131.

Example 2 an "Unaffected" HPP Mice Subpopulation

Akp2$^{-/-}$ mice generally exhibit physiological manifestations similar to human HPP patients. For example, such mice may 1) have much less (e.g., less than 1%) ALP plasma activity; 2) appear normal at birth but develop apparent skeletal disease at 6 or 11 days of age (depending on the phenotype); 3) have elevated plasma levels of at least one of PPi, PLP and PEA; 4) have progressive rachitic changes, osteopenia, and are prone to fractures; 5) have epileptic seizures and apnea; 6) have poor feeding and/or inadequate weight gain; and/or 7) die by day 21 of age. However, Akp2$^{-/-}$ mice may have different degrees of phenotypic expression. For example, in Waymire 1995, none of the Akp2$^{-/-}$ mice had mineralization defects. In addition, B6 supplement (in the form of pyridoxal, or PL, but not PN) also rescued the seizure phenotype and promoted survival in about 67% of the Akp2$^{-/-}$ mice with a C57BL/6, 129/Sv (B6129) hybrid genetic background, although the rescued animals subsequently developed defective dentition. The remaining 33% responded poorly to PL injections or were nonresponsive. However, all Akp2$^{-/-}$ mice with an inbred 129/Sv genetic background responded poorly to PL injections or were nonresponsive.

The present disclosure provides a group of Akp2$^{-/-}$ mice (with the same hybrid genetic background as in Waymire 1995 but from different generations) with varied degrees in mineralization phenotypes, but with similar shortened life span. Interestingly, recombinant TNALP rescued all the KO mice and restored GABA, serine and cystathionine to WT levels without B6 supplement.

Figure 6:
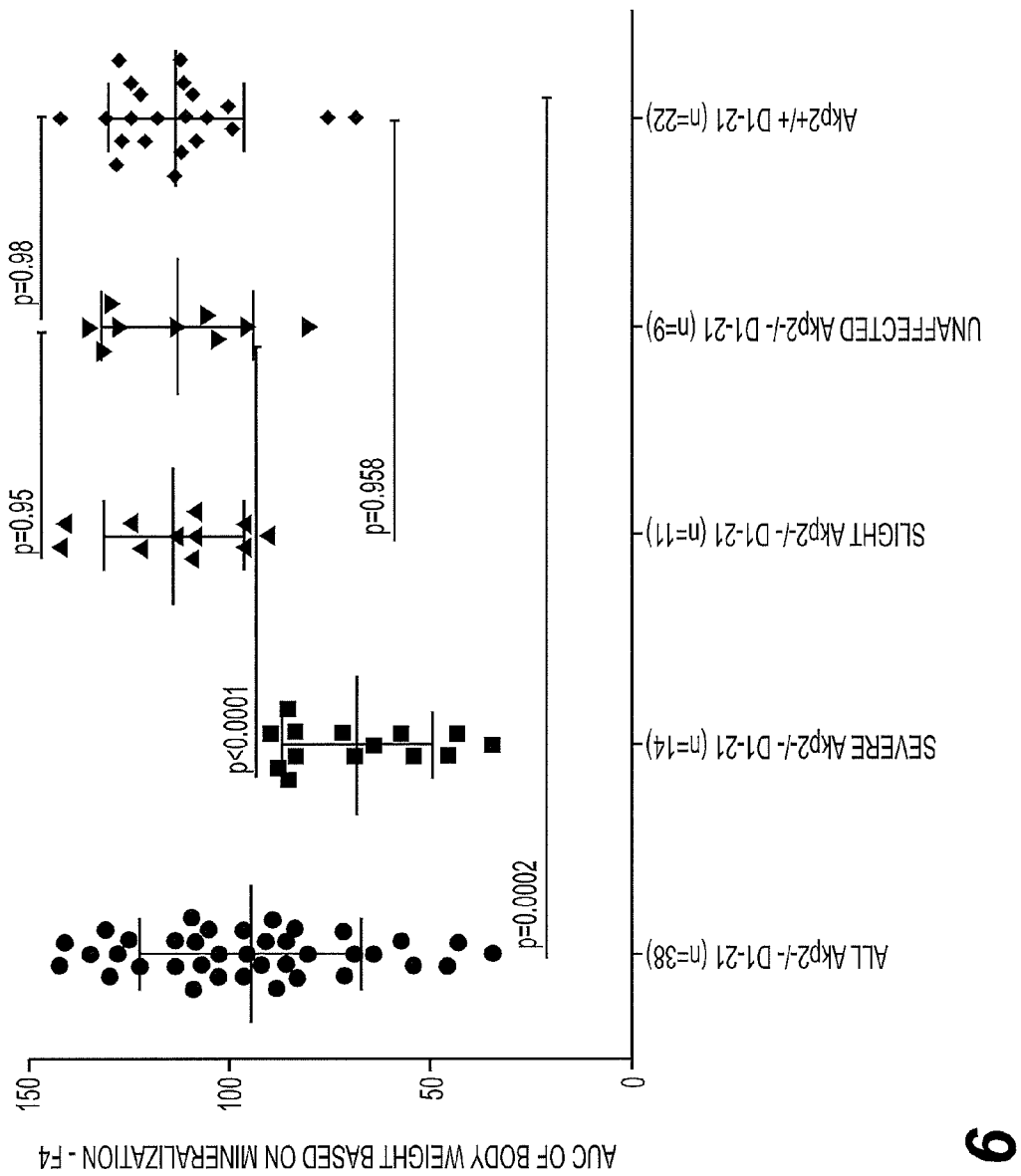
FIG. 6 depicts that body weights of $Akp2^{-/-}$ homozygous mice (generation designation: F4) correlated with their disease severity (i.e., having severe or slight mineralization defect or unaffected/normal mineralization). Wild-type mice ($Akp2^{+/+}$) were used as control.
Figure 7:
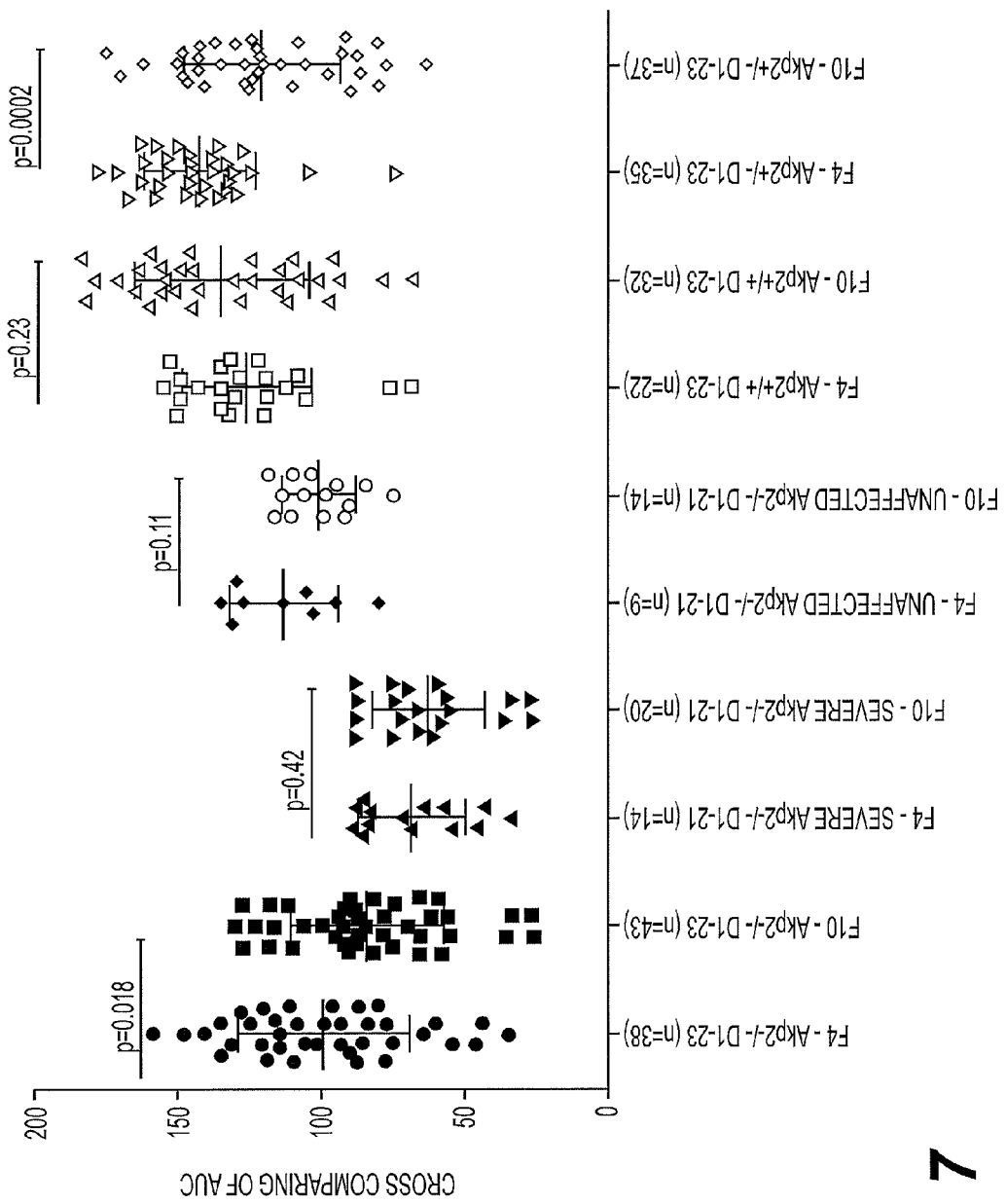
FIG. 7 depicts that body weights of $Akp2^{-/-}$ homozygous mice correlated with their disease severity mineralization phenotypes. The leftmost two groups of data ($Akp2^{-/-}$) represent data of all $Akp2^{-/-}$ homozygous mice with various (e.g., severe or unaffected) disease severity. Wild-type and $Akp2^{+/-}$ heterozygous mice were used as control.
Figure 8:
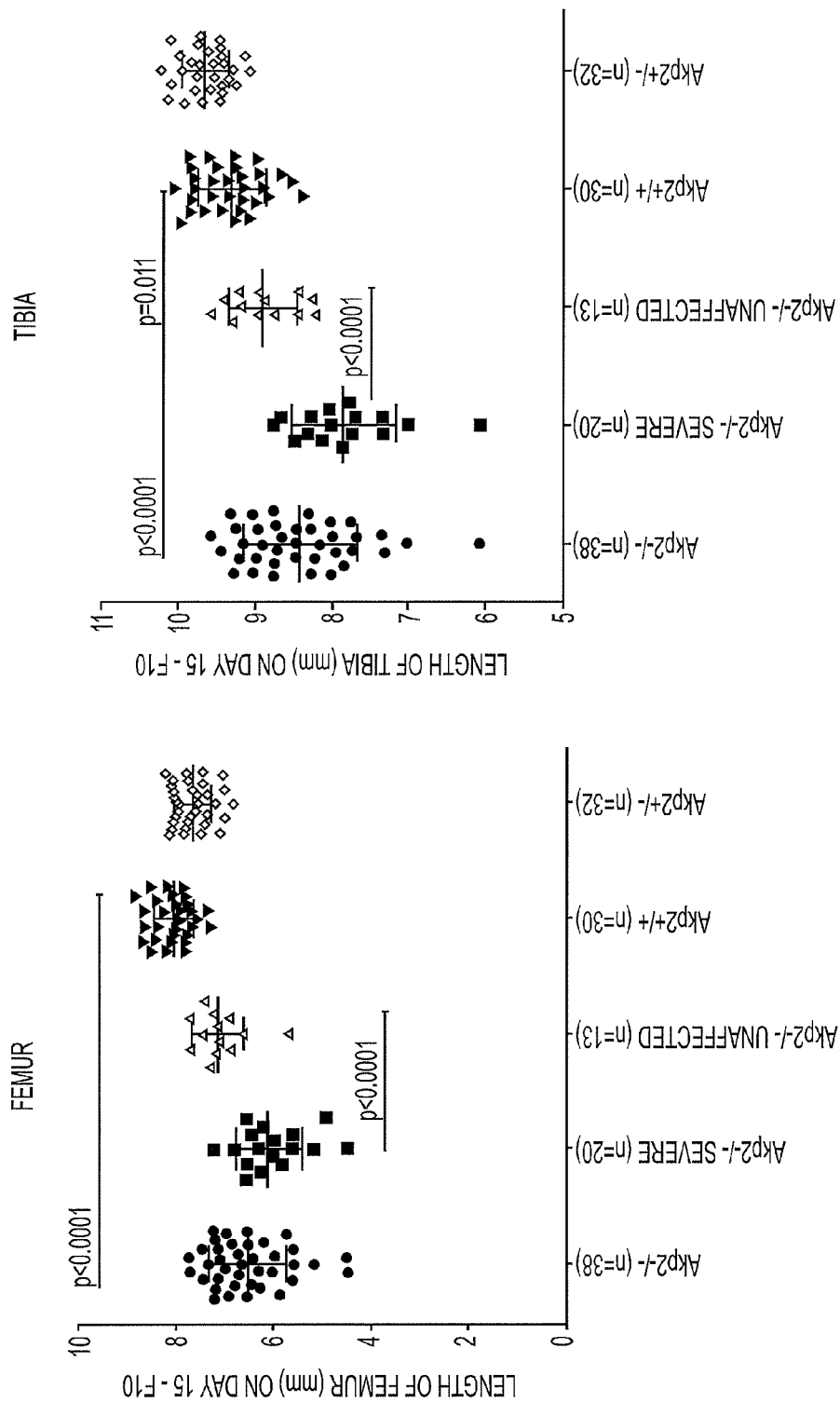
FIG. 8 depicts that the bone (femur and tibia) length of $Akp2^{-/-}$ homozygous mice (generation designation: F10) correlated with their disease severity. The leftmost groups of data ($Akp2^{-/-}$) represent data of all $Akp2^{-/-}$ homozygous mice with various (e.g., severe or unaffected) disease severity. Wild-type and $Akp2^{+/-}$ heterozygous mice were used as control.
Figure 9:
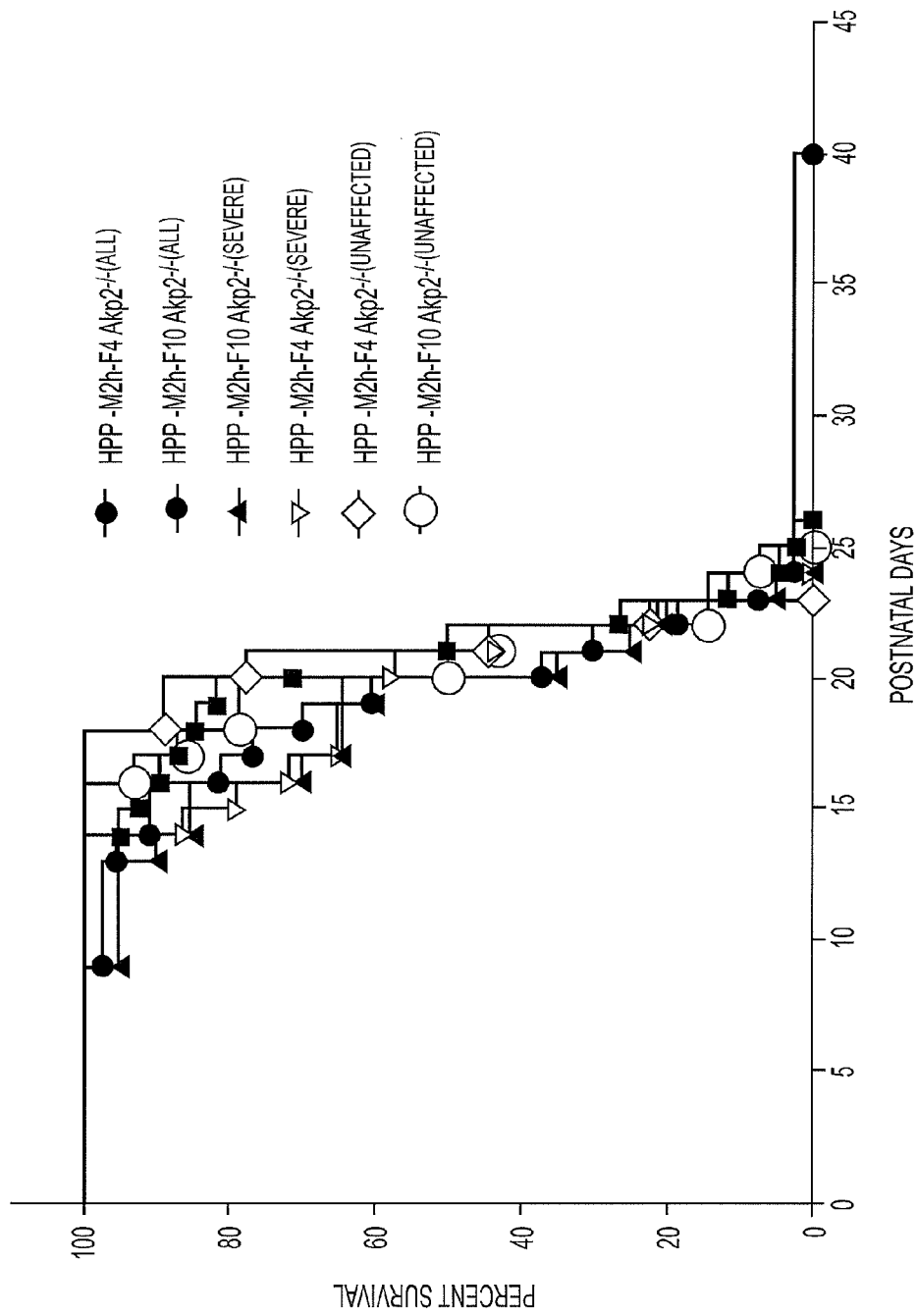
FIG. 9 presents a comparison of life span among of $Akp2^{-/-}$ homozygous mice having different mineralization phenotypes. All $Akp2^{-/-}$ homozygous mice had a significantly reduced life span regardless of mineralization phenotypes.

Different subpopulations of Akp2$^{-/-}$ mice had severe, moderate, slight or even unaffected phenotypes comparing to wild-type littermates. FIG. 4 shows the different mineralization defects of Akp2$^{-/-}$ mice. FIG. 5 shows that in various mouse colonies with the same genotype there was a wide distribution of phenotype severity. About 30% of knockout mice in each colony exhibited "unaffected" phenotypes (e.g., no significant bone mineralization defects as shown in FIG. 4, no significant body weight defects as shown in FIG. 6, and no significant bone length defects as shown in FIG. 8). Surprisingly, knockout mice with "unaffected" (mineralization) phenotypes still had a significantly reduced life span comparable to other knockout mice with more severe phenotypes (FIG. 9; showing almost all knockout mice (severe and unaffected mice) died around Day 25 after birth).

Both the impact of prophylactic treatment with and withdrawal of recombinant TNALP on vitamin B6 transmembrane transport in the brains of Akp2$^{-/-}$ mice were analyzed. In the prophylaxis study, Akp2$^{-/-}$ mice with a C57BL/6, 129/Sv (B6129) hybrid background from the HPP-M2h_F4 breeding colony were injected subcutaneously with either 8.2 mg/kg (a.k.a., 8.2 mpk) recombinant TNALP or vehicle once daily for 9 days beginning at birth. Wild-type mice on the same background were not treated and served as reference controls. In the withdrawal study, Akp2$^{-/-}$ mice on the same hybrid background and F4 generation were treated daily from birth with a similar dose of recombinant TNALP for 35 days followed by 12 days with either vehicle (withdrawal) or continued recombinant TNALP treatment. Controls included both wild type mice without treatment and mice treated with recombinant TNALP for the first 35 days and then switched to vehicle for an additional 12 days. All mice had free access to a certified commercial laboratory rodent diet (Charles River Rodent Diet 5075-US) that was not supplemented with pyridoxine. At necropsy, brains were collected, frozen in liquid nitrogen and stored at −80° C.

Figure 10:
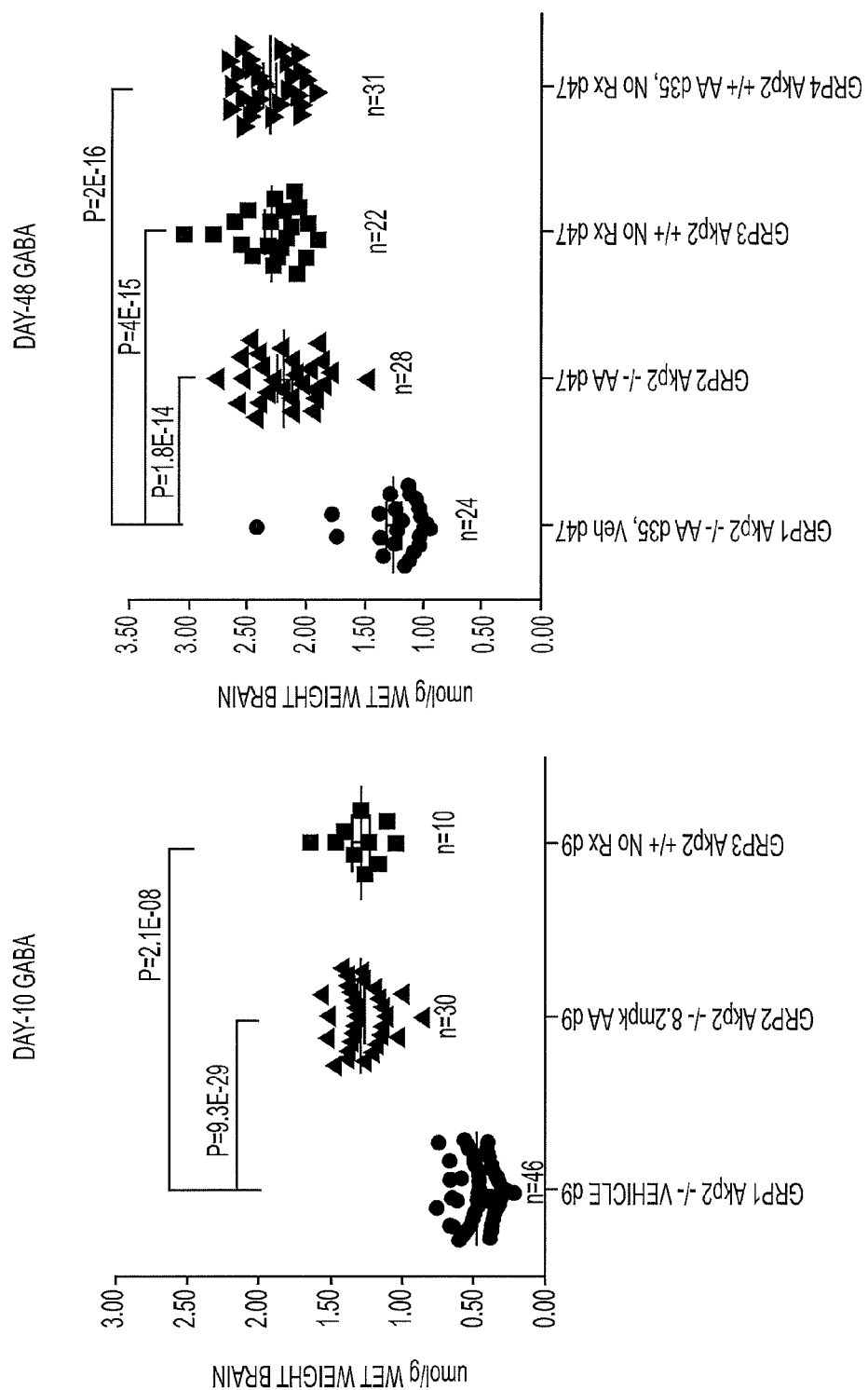
FIG. 10 depicts that $Akp2^{-/-}$ homozygous mice had reduced brain Gamma-Aminobutyric Acid (GABA) concentration, which was correctable by daily ALP (sTNALP-FcD10, or asfotase alfa) treatment. Wild-type mice with or without treatment were used as control. Left panel: GABA concentrations were measured at Day 10 for (from left to right) knockout mice treated with empty vehicle control daily to Day 9 ("GRP 1"), knockout mice treated with sTNALP-FcD10 (8.2 mg/kg) daily to Day 9 ("GRP 2"), and wild-type mice without any treatment ("GRP 3"). Right panel: GABA concentrations were measured at Day 48 for (from left to right) knockout mice treated with sTNALP-FcD10 (8.2 mg/kg) daily to Day 35 and then treated with empty vehicle control (i.e., discontinuation of treatment) daily to Day 47 ("GRP 1"), knockout mice treated with sTNALP-FcD10 daily to Day 47 ("GRP 2"), wild-type mice without any treatment ("GRP 3"), and wild-type mice treated with sTNALP-FcD10 daily to Day 35 and then treated with empty vehicle control daily to Day 47 ("GRP 4").
Figure 11:
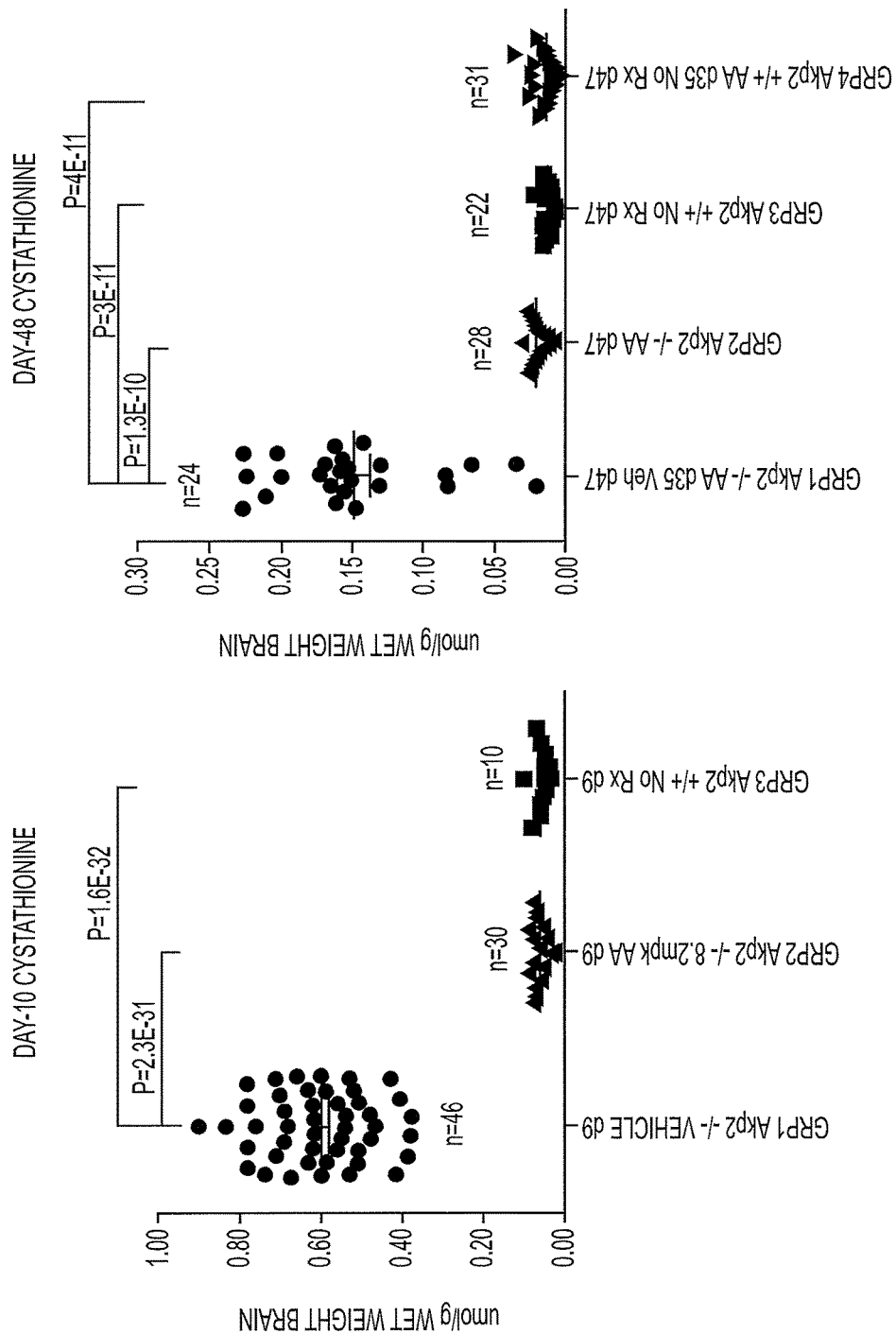
FIG. 11 depicts that $Akp2^{-/-}$ homozygous mice had significantly elevated brain Cystathionine concentration, which was correctable by daily ALP (sTNALP-FcD10, or asfotase alfa) treatment. Wild-type mice with or without treatment were used as control. Left panel: cystathionine concentrations were measured at Day 10 for (from left to right) knockout mice treated with empty vehicle control daily to Day 9 ("GRP 1"), knockout mice treated with sTNALP-FcD10 (8.2 mg/kg) daily to Day 9 ("GRP 2"), and wild-type mice without any treatment ("GRP 3"). Right panel: cystathionine concentrations were measured at Day 48 for (from left to right) knockout mice treated with sTNALP-FcD10 (8.2 mg/kg) daily to Day 35 and then treated with empty vehicle control daily to Day 47 ("discontinuation") ("GRP 1"), knockout mice treated with sTNALP-FcD10 daily to Day 47 ("GRP 2"), wild-type mice without any treatment ("GRP 3"), and wild-type mice treated with sTNALP-FcD10 daily to Day 35 and then treated with empty vehicle control daily to Day 47 ("GRP 4").
Figure 12:
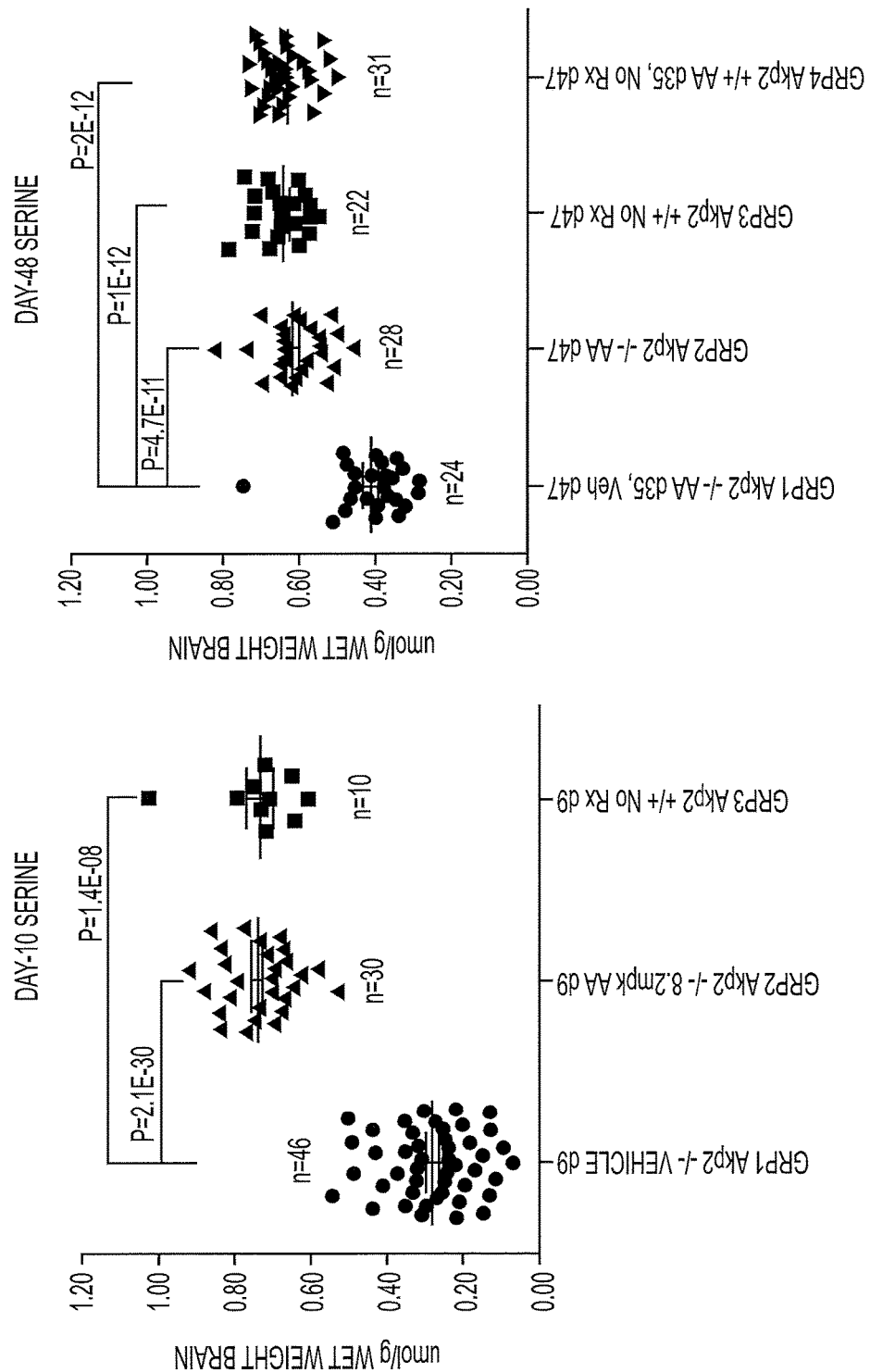
FIG. 12 depicts that Akp2$^{-/-}$ homozygous mice had significantly reduced brain Serine concentration, which was correctable by daily ALP (sTNALP-FcD10, or asfotase alfa) treatment. Wild-type mice with or without treatment were used as control. Left panel: serine concentrations were measured at Day 10 for (from left to right) knockout mice treated with empty vehicle control daily to Day 9 ("GRP 1"), knockout mice treated with sTNALP-FcD10 daily to Day 9 ("GRP 2"), and wild-type mice without any treatment ("GRP 3"). Right panel: serine concentrations were measured at Day 48 for (from left to right) knockout mice treated with sTNALP-FcD10 (8.2 mg/kg) daily to Day 35 and then treated with empty vehicle control daily to Day 47 ("discontinuation") ("GRP 1"), knockout mice treated with sTNALP-FcD10 daily to Day 47 ("GRP 2"), wild-type mice without any treatment ("GRP 3"), and wild-type mice treated with sTNALP-FcD10 daily to Day 35 and treated with empty vehicle control daily to Day 47 ("GRP 4").

With continuous daily treatment of sTNALP-FcD10, Akp2$^{-/-}$ mice (including those having the "unaffected" phenotype) had a much longer life span compared to untreated mice. As shown in FIGS. 10-12, right panels, such "unaffected" knockout mice survived at least to Day 48 (when all mice were terminated).

This discovery of an "unaffected" Akp2$^{-/-}$ mice subpopulation is consistent with previous reports of a HPP patient subpopulation with Vitamin B6-resistant seizures but without bone deformities (e.g., see de Roo et al., 2014 *Molecular Genetics and Metabolism* 111:404-407 and Baumgartner-Sigl et al., 2007 *Bone* 40:1655-1661). Clearly, there is a risk for such subpopulation of HPP patients to miss out on timely and effective diagnosis if medical practitioners limit their HPP diagnosis methods to the traditional detection of bone deformities or mineralization defects. Patients with normal bone mineralization should not be overlooked for the possibility of having other HPP-related symptoms. If a patient has seizures and/or aberrant ALP protein levels/function (e.g., with an increased levels of ALP substrates, such as PPi, PLP, and PEA), determination should be made to verify such patient belongs to an "unaffected" subpopulation and whether treatment with ALP supplement is indicated. Generally, if a patient has seizures, especially vitamin B6-resistant seizures, extra effects should be taken to test if the patient has a defective ALP function or increased levels of ALP substrates, such to determine if an ALP supplement treatment is indicated.

Example 3 Akp2$^{-/-}$ Mice have Reduced Brain Gamma-Aminobutyric Acid (GABA) Correctable by Daily Treatment of Recombinant sTNALP-FcD10

Alkaline phosphatases, such as TNALP, PLALP, GALP and IALP, are physiologically active toward their substrates phsphoethanolamine (PEA), inorganic pyrophosphate (PPi) and pyridoxal 5'-phosphate (PLP). Reduced alkaline phosphatase activity, such as in a TNALP knockout or mutant subject, results in accumulation of extracellular PLP and PPi. The accumulation of systemic PLP leads to a concomitant decrease in intracellular PLP, since PLP, in its phosphorylated state, cannot cross the plasma membrane to enter cells. PLP is the catalytically active form of vitamin B6 and acts as a cofactor for more than 140 different enzyme reactions involved in amine and amino acid metabolism (Percudani, R. & Peracchi, A., *EMBO Rep.*, 4:850 4, 2003). For example, low intracellular PLP may lead to reduced CNS GABA, which may further lead to seizures. In addition, a high concentration of PPi may result in rickets (osteomalacia), craniosynostosis, respiratory compromise, nephrocalcinosis, or muscle weakness. In severe cases these complications may result in death. Abnormal amine and amino acid metabolism, due to decreased alkaline phosphatase activity, contributes to the pathogenesis and phenotype characteristic of HPP.

To measure brain amino acid concentrations, whole mouse brains from −80° C. storage were homogenized in 2.5 µL of phosphate buffered saline (pH 7.4, plus protease inhibitor cocktail, Roche Diagnostics Cat #05892970001) per milligram tissue. Tissue suspensions were sonicated for 15 seconds and clarified by three successive centrifugations at 21,000×g for 15 min at 4° C. to remove debris. Supernatant extracts were frozen at −80° C. until assay. Total protein was measured using the Coomassie Plus Bradford microplate assay (Thermo Scientific Cat # PI23236).

Amino acid concentrations were quantified by Biochrom 30+ (Biochrom Ltd., UK) amino acid analysis according to a lithium high performance program using L-norleucine (NORL) (Sigma Cat# N8513) as the internal standard (ISTD). Brain extracts were deproteinized by a 1:4 dilution into a master mix containing NORL-ISTD and 5-sulfosalicyclic acid dihydrate (SSA) (Sigma Cat# S7422) at final concentrations of 250 µmol/L and 2.5%, respectively. Protein precipitates were removed by two successive centrifugations at 10,000×g, 4° C. A standard mix was prepared by adding acid, neutral, and basic amino acid standards (Sigma Cat# A6407 and A6282) as well as NORL-ISTD to the final volume of 250 µmol/L (with SSA at 2.5%). 40 µL of standard mix and deproteinized samples were injected into the analyzer and amino acids were separated as outlined in the "Accelerated Analysis of Amino Acids in Physiological Samples," Biochrom Application Note: 90 (according to Biochrom Ltd. (Cambridge, UK) manufacturer's instructions). Amino acid concentrations (µmol/L) were determined using EZChrom software. Final concentrations were expressed as µmol amino acid/gram wet weight brain.

As shown in the left panel of FIG. 10, Akp2$^{-/-}$ mice exhibited a decreased GABA concentration relative to wild-type mice, which was corrected by a continuous daily treatment of sTNALP-FcD10. The right panel of FIG. 10 shows that GABA restoration by such continuous treatment lasted at least to Day 48, significantly beyond the Day 25 life span for knockout mice. However, discontinuation of sTNALP-FcD10 treatment after Day 35 reduced GABA concentration again in Akp2$^{-/-}$ mice.

To further investigate the function of sTNALP-FcD10 (SEQ ID NO: 1), brain cystathionine and serine (both of which are known to be regulated by PLP for their production) concentrations were measured and compared between Akp2$^{-/-}$ mice and wild-type mice. As shown in FIGS. 11 and 12, respectively, Akp2−/− mice had significantly reduced brain serine level, but significantly elevated brain cystathionine level, compared to those of wild-type mice. Continuous treatment with sTNALP-FcD10, however, elevated serine levels and reduced cystathionine levels in those knockout mice to a level comparable to wild-type mice. Similarly, discontinuation of sTNALP-FcD10 treatment after Day 35 reversed the correction by sTNALP-FcD10 (see right panels of FIGS. 11 and 12).

Daily sTNALP-FcD10 treatment improved in vivo alkaline phosphatase function and increased brain GABA concentration. Such treatment re-balanced the abnormal amine and amino acid metabolism in Akp2$^{-/-}$ mice and indicated the efficacy of such a treatment for seizure and seizure-related phenotypes.

Interestingly, the bone-target signal D10 in the tested construct did not prevent its functions to improve knockout mice survival and ameliorate seizure-related physiological parameters, such as restoring GABA and serine levels and decreasing cystathionine levels in brain.

Example 4 Clinical Trial Improvement

Clinical trials tested whether hsTNALP-FcD10 (asfotase alfa, SEQ ID NO: 1) treatment improved seizure in HPP patients. All patients with history of vitamin B6-responsive seizures were very severely affected by HPP, and two of them died after the start of treatment with hsTNALP-FcD10. One of the patients had seizures at birth and died after several years on hsTNALP-FcD10 treatment. Vitamin B6 was supplied to the patient but was insufficient to prevent seizures. Clonazepam was then administered but the patient died after experiencing seizures along with brain edema, fever, differential ion imbalance, and potential cardiomyopathy.

Six patients with history of B6-responsive seizures who were on a B6 prophylaxis regimen prior to the start of the treatment with hsTNALP-FcD10 did not experience seizures during hsTNALP-FcD10 treatment. One additional patient, who likely had a history of B6-responsive seizures and who discontinued prophylaxis with B6 immediately upon initiation of hsTNALP-FcD10 treatment, experienced seizures that were resolved when B6 co-therapy prophylaxis was resumed. Another patient with history of B6-responsive seizures, who maintained B6 prophylaxis in conjunction with the treatment with hsTNALP-FcD10, discontinued B6 prophylaxis after one year of co-treatment and maintained hsTNALP-FcD10 treatment only. This patient had no seizure experience after the discontinuation of B6 prophylaxis.

The preliminary clinical data showed that hsTNALP-FcD10 treated seizures in HPP patients. Clinical data did show that monotherapy with hsTNALP-FcD10 was effective and vitamin B6 supplement was not necessary, at least after co-administration of the two molecules for a certain length of time (e.g., one year in one patient). The therapeutic effect of hsTNALP-FcD10 post-B6-discontinuation is recognized, since B6-responsive seizures usually cannot be completely prevented by B6 supplement (e.g., only a portion of $Akp2^{-/-}$ mice may be rescued by vitamin B6 supplementation). However, if there was no co-administration (of B6 and hsTNALP-FcD10) step (e.g., no co-administration in one patient) or, probably, if the co-administration period did not last long enough, the hsTNALP-FcD10 treatment alone was not sufficient to continuously prevent reappearance of B6-responsive seizures.

HPP patients were evaluated in a retrospective natural history study and two Phase II clinical trials with asfotase alfa treatment. The clinical data for similar patients (e.g., severely affected infants and young children with perinatal or infantile HPP) from different trials (matched for their history of rachitic chest, respiratory compromise, and/or vitamin B6-responsive seizures), with or without asfotase alfa treatment, were collected and compared. Forty-eight (48) patients were identified from the natural history study and 37 patients were identified from the asfotase alfa treatment studies, with the demographics as shown below in Table 1.

TABLE 1

Demographics for patients from clinical studies

|  | Historical Controls (N = 48) | Treated (N = 37) |
|---|---|---|
| Age Enrolled |  |  |
| Mean ± SD | NA | 23 ± 24 months |
| Median (min, max) |  | 9 (0, 71) |
| Age at onset of HPP | n = 47 | n = 26* |
| Mean ± SD | 1 ± 2 months | 1 ± 2 months |
| Median (min, max) | 0 (0, 6) | 1 (0, 6) |
| Gender, % (n) |  |  |
| Male | 54% (26) | 43% (16) |
| Female | 46% (22) | 57% (21) |
| Race, % (n) |  |  |
| White | 83% (40) | 78% (29) |
| Asian | 4% (2) | 16% (6) |
| Other | 13% (6) | 5% (2) |
| Duration of treatment |  |  |
| Median (min, max) | NA | 2 (0, 5) years |

NA: not applicable.
*Not collected in one trial

The signs/symptoms for severe HPP of these patients at beginning of the studies (i.e., prior to the asfotase alfa treatment for the patients from the Phase II studies) were recorded and summarized (Table 2). Patients from the natural history studies and from the Phase II treatment studies ("treated" in Table 2, for consistency with Table 1) were chosen with similar percentages of signs/symptoms of severe HPP. Ten of 48 patients in the natural history studies and 13 of 37 patients in the Phase II treatment studies had vitamin B6-responsive seizures.

TABLE 2

Summary of study population having signs of severe HPP

| Signs of Severe HPP | Historical Controls (N = 48) | "Treated" (N = 37) | P-Value |
|---|---|---|---|
| Rachitic chest | 83% (40) | 81% (30) | 0.78 |
| Respiratory compromise | 83% (40) | 73% (27) | 0.29 |
| Vitamin $B_6$-responsive seizures | 21% (10) | 35% (13) | 0.22 |
| All of the above | 17% (8) | 22% (8) | 0.59 |

The survival rate of the selected patients from the natural history studies and from the Phase II asfotase alfa treatment was compared and summarized in Table 3. Most patients (about 58%) in the natural history studies failed to survive to one year, while their survival rates continued to decrease and reached the bottom line of about 27% between the age of one year to three-and-a-half years. However, most patients (about 89%) treated with asfotase alfa survived even beyond five years of age.

TABLE 3

Survival rate of patients selected from different studies at different ages

|  | Survival Rate | |
|---|---|---|
| Patient Age (Yrs) | Historical Controls | Treated |
| 1 | 42% | 95% |
| 3.5 | 27% | 89% |
| 5 | 27% | 89% |

The surviving patients from different studies were analyzed for signs of severe HPP after reaching one year old. As shown in Table 4, out of the 48 patients from the natural history study group, 33% of patients having rachitic chest (13 of 40) survived, while 18% of patients suffering from respiratory compromise (7 of 40) survived. However, not a single patient (0 of 10) with Vitamin B6-responsive seizures survived. In contrast, in the Phase II treatment groups, 90% patients (27 of 30) having rachitic chest survived and 89% patients (24 of 27) having respiratory compromise survived. Specifically, 85% patients (11 of 13) having vitamin B6-responsive seizures survived. Thus, asfotase alfa treatment dramatically promoted the survival rate of patients with vitamin B6-responsive seizures, while vitamin B6 alone (for those patients in the natural history study group) rarely improved survival by inhibiting seizures.

TABLE 4

Summary of study population having signs of severe HPP after treatment

| Signs of Severe HPP | Historical Controls (N = 48) | Treated (N = 37) |
|---|---|---|
| Rachitic chest | 33% (13/40) | 90% (27/30) |
| Respiratory compromise | 18% (7/40) | 89% (24/27) |
| Vitamin $B_6$-responsive seizures | 0% (0/10) | 85% (11/13) |
| All of the above | 0% (0/8) | 88% (7/8) |

While patient survival was taken as the primary parameter for analysis, invasive ventilation-free survival was set as the secondary analytical parameter. Similarly, in Table 5, only 31% patients in the natural history studies survived without invasive ventilation at age of one year, while their invasive ventilation-free survival rates continued to decrease and reach the bottom line of about 25% between the age of one year to three-and-a-half years. However, most patients (about 83%) treated with asfotase alfa survived even beyond five years.

TABLE 5

Invasive ventilation-free survival rate of patients by age

| Patient Age (Yrs) | Invasive Ventilation-Free Survival Rate | |
|---|---|---|
| | Historical Controls | Treated |
| 1 | 31% | 96% |
| 3.5 | 25% | 83% |
| 5 | 25% | 83% |

Asfotase alfa treatment for infants severely affected by HPP significant improved their skeletal mineralization, which occurred on average as early as 3 months, continued, and was generally sustained over 3 years. Patients showed improved gross motor skills, fine motor skills, and cognitive skills.

In conclusion, compared to historical controls, asfotase alfa treatment helped severely affected patients with perinatal and infantile HPP (which were at high risk of death) to improve both the overall survival rate (89% vs. 27%, P<0.0001) and the invasive ventilation-free survival rate.

Example 5 Treating Seizure in Mice and Humans $Akp2^{-/-}$ mice with minor, unaffected, or undetectable mineralization defects and wild-type littermates are treated with a soluble recombinant ALP construct (e.g., sTNALP, sTNALP-Fc, sTNALP-FcD10 or other recombinant isozyme constructs). Seizures before and after the treatment are recorded by video camera or other physiological methods. Concentrations of brain GABA, serine, and cystathionine (may also come from serum or urine sources) are tested and compared with known methodology. The therapeutic effect of recombinant ALP is shown by the discovered reduced seizures and/or restored GABA/serine concentration after treatment in $Akp2^{-/-}$ mice. Different dosage regimens are tested and compared. Vitamin B6 alone or combination therapy is also tested for any potential synergetic effect.

Similarly, HPP patients with minor, unaffected, or undetectable mineralization defects and healthy volunteers are treated with a soluble recombinant ALP construct disclosed in the present disclosure. Seizures before and after the treatment are reported and compared. Physiological parameters, such as plasma and/or urine cystathionine (or brain concentrations of GABA, serine and/or cystathionine), are measured and recorded. The therapeutic effect of recombinant ALP is shown by the discovered reduced seizures and/or restored plasma/urine cystathionine concentration after treatment. Vitamin B6 alone or combination therapy is also tested for any potential synergetic effect. Different time lengths for co-therapy are tested to optimize the co-therapy process followed by ALP supplement therapy alone.

A new subpopulation of patients not previously diagnosed as affected by HPP is also identified by genetic screening or other known methodologies to have defective alkaline phosphatase protein levels and/or function. One characteristic symptom such patient subpopulation has is seizures, either vitamin B6-responsive or not. Patients in such subpopulation are then treated with recombinant ALP constructs disclosed herein, with or without B6 supplement. If B6 supplement is co-administered, it will be discontinued after a certain time (determined by the physician or drug administrator according to the individual situation of each patient) followed by ALP single therapy.

Example 6 Maximization of Seizure Treatment by Monitoring Biomarkers in Patients A specific subpopulation of patients having seizures is identified by their characteristic above-normal levels of alkaline phosphatase substrates (e.g., PPi, PEA, and PLP). Such abundant DNA, RNA, and/or protein levels of those substrates are detected by regular methodologies known in the art, including, e.g., quantitative PCR, Southern Blot, Northern Blot, PAGE, SDS-PAGE, Western Blot, etc. After identifying this specific patient subpopulation, recombinant ALP constructs disclosed herein will be administered to relieve seizure symptoms. Optionally, one or more other anti-seizure drugs, such as vitamin B6 vitamers, may be co-administered for at least a period of time. For such single or combinational therapy with ALP replacement, patients are closely monitored for their endogenous biomarkers prior to, during, and post-treatment. For example, when vitamin B6 is co-administered, physicians or other drug administers will monitor the levels of biomarkers in the recipient patients to determine, preferably based on the individual situation of each patient, the time point to co-administer vitamin B6, the dosage regimen for B6 and/or recombinant ALP, the length of period for co-administration, and the time point to discontinue vitamin B6 co-administration, etc.

Biomarkers suitable for monitoring herein include, at least, alkaline phosphatase substrates (PPi, PEA, and/or PLP), or other biomarkers affected by these alkaline phosphatase substrates (e.g., GABA, cystathionine, serine, dopamine, serotonin, histamine, D-serine and hydrogen sulfide, etc.). Such biomarkers may be tested using patient serum or urine or by other standard testing methodology known in the art.

Example 7 Failure of Vitamin B6 to Treat Seizure in $Akp2^{-/-}$ Mice

Figure 13:
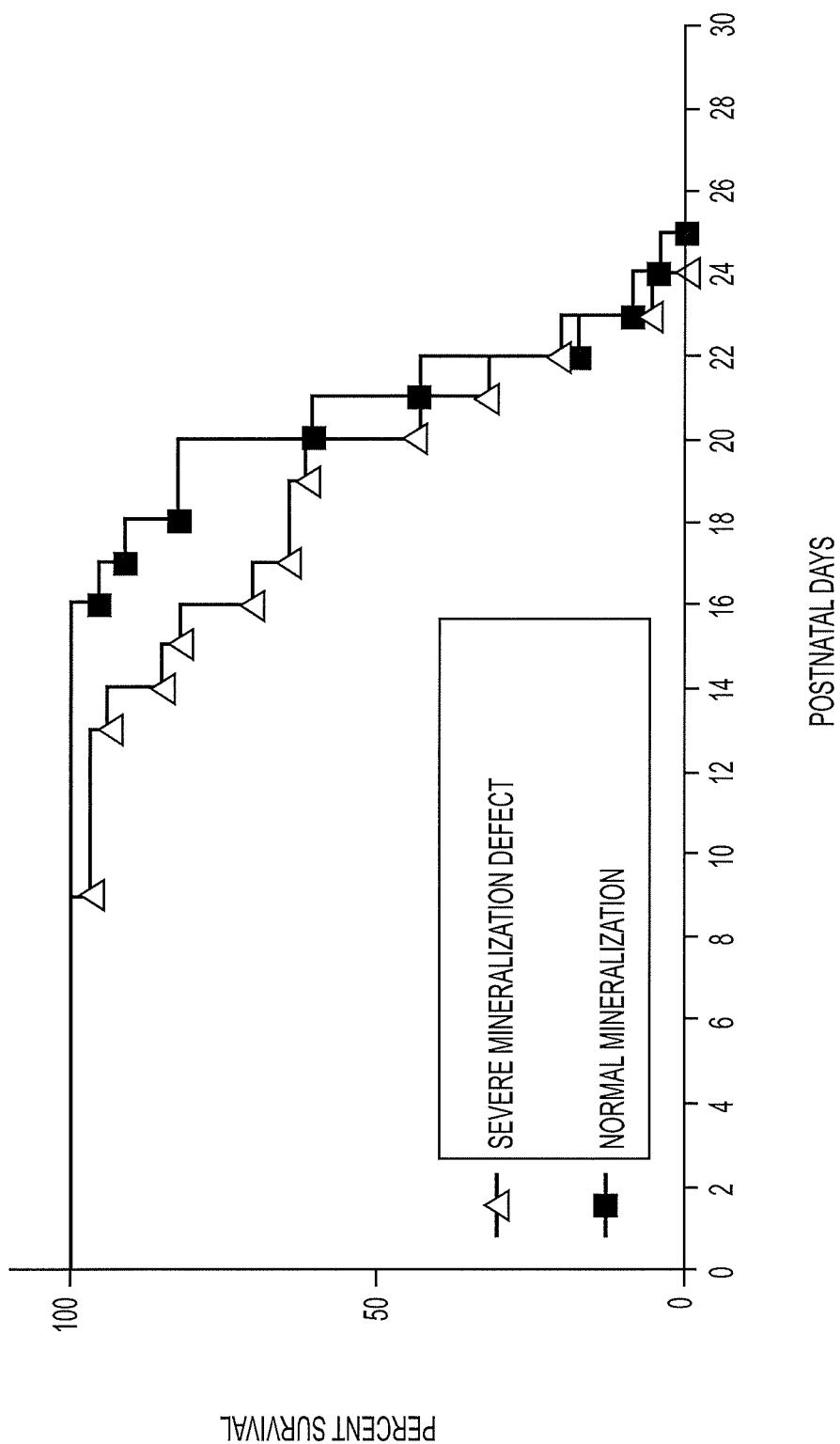
FIG. 13 compares life spans of Akp2$^{-/-}$ homozygous mice (having severe mineralization defect or normal mineralization) receiving 325 ppm dietary pyridoxine supplement.
Figure 14:
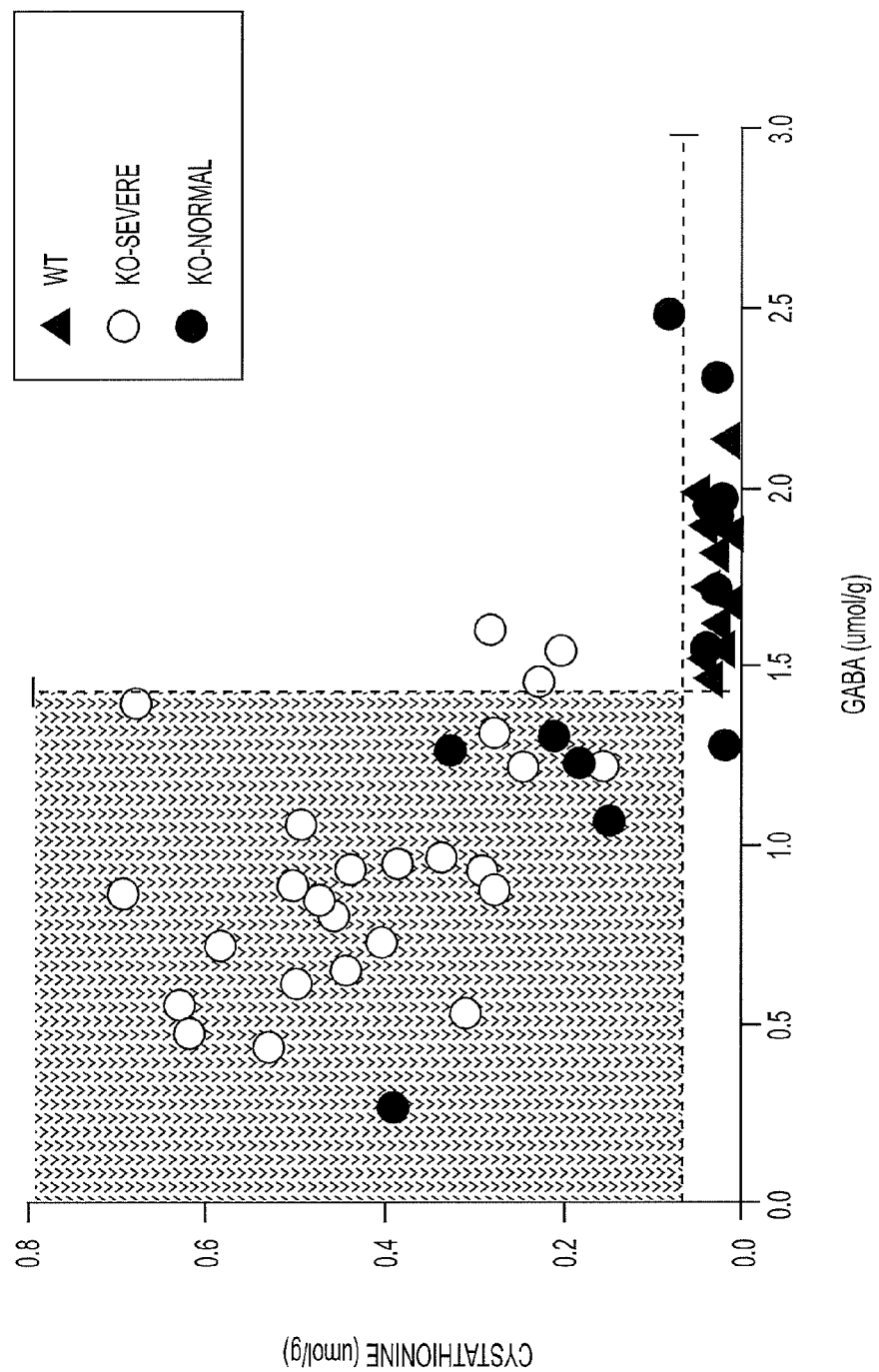
FIG. 14 compares the brain GABA and Cystathionine concentrations of wild-type (WT) or Akp2$^{-/-}$ homozygous mice having severe mineralization defect (KO-severe) or normal mineralization (KO-normal), all receiving 325 ppm dietary pyridoxine supplement. The shaded area refers to a profile where mice have comparatively low brain GABA concentration but comparatively high brain Cystathionine concentration.

Vitamin B6 treatment is a standard seizure treatment. However, many HPP patients and $Akp2^{-/-}$ mice have B6-resistant seizure, which is not correctable by vitamin B6 administration and can lead to death. A further study was carried out to confirm the lack of effect of vitamin B6 on Akp2$^{-/-}$ mice. In the study, Akp2$^{-/-}$ mice were treated with 325 ppm dietary vitamin B6 (pyridoxine) supplement. However, seizures were still observed in Akp2$^{-/-}$ mice with either normal bone mineralization or with severe mineralization defects. None of the knockout mice with either mineralization phenotype survived past 25 days (FIG. 13).

To confirm that the biomarker profiles cannot be corrected by pyridoxine supplement in Akp2$^{-/-}$ mice, brain amino acid concentrations were measured using the same method as disclosed in Example 3, except that S-(2-Aminoethyl)-L-cysteine (AEC) (Sigma Cat# A2636) (instead of L-norleucine (NORL)), was used as the internal standard (ISTD), and finally 15 µL, rather than 40 µL, of standard mix and deproteinized samples were analyzed. As shown in FIG. 14, 17-19 day old wild type mice receiving dietary pyridoxine supplement had comparatively high GABA concentration and low Cystathionine concentration in brain, while Akp2$^{-/-}$ mice with severe mineralization defects (i.e., the typical Vitamin B6-resistant HPP group, having biomarker profiles in the shaded area) had comparatively low GABA concentration and high Cystathionine concentration in brain (shown in the shaded area), despite 325 ppm dietary pyridoxine supplement. For Akp2$^{-/-}$ mice with normal bone mineralization, some had GABA and Cystathionine concentrations correctable by pyridoxine supplement, while there was also a subgroup having those biomarkers not correctable by pyridoxine supplement (shown in the shaded area).

In conclusion, a subgroup of Akp2$^{-/-}$ mice was confirmed to have normal bone mineralization but lethal, vitamin B6-resistant, seizures. Correspondingly, a similar subpopulation of patients also exists (whether diagnosed as HPP patients or not) with ALP defects and seizures but normal bone mineralization. A new diagnosis protocol (based on ALP functions, such as PLP/PPi/PEA levels or biomarkers as disclosed herein) is thus suggested to identify such subpopulation of patients in order to effectively treat their symptoms in a timely manner. In addition, ALP (such as asfotase alfa) supplementation (either alone or in combination with vitamin B6), rather than vitamin B6 alone, should be administered for a better therapy for this subpopulation of patients.

Many modifications and variations disclosed herein can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the invention being indicated by the following claims.

What is claimed is:

1. A method of treating seizure in a human subject having aberrant levels of at least one alkaline phosphatase substrate selected from pyridoxal 5'-phosphate (PLP), inorganic pyrophosphate (PPi), and phosphoethanolamine (PEA), comprising administering a therapeutically effective amount of a recombinant alkaline phosphatase to the subject, wherein the subject has been determined to be nonresponsive to vitamin B6 treatment for the seizure.

2. The method of claim 1, further comprising:
   (i) identifying a population of subjects with aberrant alkaline phosphatase activities who suffer, or are at risk to suffer, from seizure; or
   (ii) identifying a population of subjects with above-normal levels of at least one alkaline phosphatase substrate who suffer, or are at risk to suffer, from seizure.

3. The method of claim 1, wherein the human subject has been diagnosed with hypophosphatasia (HPP) and wherein the human subject has minor or non-detectable bone mineralization defects.

4. The method of claim 1, wherein the human subject has not been diagnosed with HPP.

5. The method of claim 1, wherein the human subject has:
   a) increased serum pyridoxal 5'-phosphate (PLP);
   b) reduced intracellular pyridoxal 5'-phosphate (PLP);
   c) at least one of reduced brain Gamma-Aminobutyric Acid (GABA) and reduced brain serine; or
   d) at least one of increased brain and urinary cystathionine.

6. The method of claim 1, wherein the recombinant alkaline phosphatase is administered to the human subject:
   a) daily for at least one week, one month, three months, six months, or one year;
   b) in conjunction with the at least one additional therapeutic agent; or
   c) in a dosage from about 0.1 mg/kg/day to about 20 mg/kg/day, or a comparable weekly dosage.

7. The method of claim 1, wherein administration of the recombinant alkaline phosphatase elevates brain GABA.

8. The method of claim 6, wherein the at least one additional therapeutic agent is an anti-seizure drug or at least one of vitamin B6 (pyridoxine) and a vitamin B6 vitamer.

9. The method of claim 6, further comprising:
   i) maintaining co-administration of the at least one additional therapeutic agent with the recombinant alkaline phosphatase for a pre-determined time; and
   ii) withdrawing administration of the at least one additional therapeutic agent while maintaining administration of the recombinant alkaline phosphatase to the human subject.

10. The method of claim 8, wherein the anti-seizure drug and the recombinant alkaline phosphatase are co-administered to the human subject for at least one month, at least six months, or at least one year.

11. The method of claim 1, wherein the recombinant alkaline phosphatase:
   a) comprises at least one of a tissue nonspecific alkaline phosphatase (TNALP), a placental alkaline phosphatase (PALP), a germ cell alkaline phosphatase (GCALP), or an intestinal alkaline phosphatase (IALP);
   b) comprises an amino acid sequence of SEQ ID NO: 2;
   c) is a fusion protein;
   d) is fused to an immunoglobulin molecule or a negatively charged peptide; or
   e) comprises sALP-Fc-D10, wherein the sALP is a soluble form of the recombinant alkaline phosphatase, the Fc is a fragment crystallizable region (Fc), and the D10 comprises ten polyaspartate residues.

12. The method of claim 11, wherein the immunoglobulin molecule is a fragment crystallizable region (Fc).

13. The method of claim 12, wherein the Fc comprises an amino acid sequence of SEQ ID NO: 3.

14. The method of claim 11, wherein the negatively charged peptide is at least one of D10, D16, E10, and E16.

15. The method of claim 11, wherein the recombinant alkaline phosphatase comprises an amino acid sequence of SEQ ID NO: 1 or SEQ ID NO: 4.

16. The method of claim 6, wherein the recombinant alkaline phosphatase is administered in a dosage from about 0.5 mg/kg/day to about 5 mg/kg/day, or a comparable weekly dosage.

17. The method of claim 6, wherein the recombinant alkaline phosphatase is administered in a dosage from about 0.1 mg/kg/day to about 1 mg/kg/day, or a comparable weekly dosage.

18. The method of claim 1, wherein the recombinant alkaline phosphatase is administered by at least one of intravenous, intramuscular, subcutaneous, sublingual, intrathecal, and intradermal route.

19. The method of claim 18, wherein the recombinant alkaline phosphatase is administered intravenously.

20. The method of claim 19, wherein the recombinant alkaline phosphatase is administered intravenously and then subcutaneously.

* * * * *